US007396505B2

(12) United States Patent
Pope et al.

(10) Patent No.: US 7,396,505 B2
(45) Date of Patent: Jul. 8, 2008

(54) USE OF COCRMO TO AUGMENT BIOCOMPATIBILITY IN POLYCRYSTALLINE DIAMOND COMPACTS

(75) Inventors: Bill J. Pope, Springville, UT (US); Richard H. Dixon, Provo, UT (US); Jeffery K. Taylor, Loomis, CA (US); Clayton F. Gardinier, American Fork, UT (US); Troy Medford, Pleasant Grove, UT (US); Dean C. Blackburn, Springville, UT (US); Michael A. Vail, Genola, UT (US); Louis M. Pope, Provo, UT (US); Kenneth M. Jensen, Springville, UT (US)

(73) Assignee: Diamicron, Inc., Orem, UT (US)

( * ) Notice: Subject to any disclaimer, the term of this patent is extended or adjusted under 35 U.S.C. 154(b) by 523 days.

(21) Appl. No.: 10/929,114

(22) Filed: Aug. 27, 2004

(65) Prior Publication Data

US 2005/0158200 A1 Jul. 21, 2005

Related U.S. Application Data

(63) Continuation-in-part of application No. 10/259,187, filed on Sep. 28, 2002, now abandoned, which is a continuation-in-part of application No. 10/229,907, filed on Aug. 28, 2002, which is a continuation-in-part of application No. 09/494,276, filed on Jan. 30, 2000, now Pat. No. 6,793,681, which is a continuation-in-part of application No. 09/457,226, filed on Dec. 8, 1999, now abandoned, which is a continuation-in-part of application No. 08/844,395, filed on Apr. 18, 1997, now Pat. No. 6,010,633, which is a continuation of application No. 08/631,877, filed on Apr. 16, 1996, now Pat. No. 5,645,601, which is a continuation of application No. 08/289,696, filed on Aug. 12, 1994, now abandoned.

(60) Provisional application No. 60/325,832, filed on Sep. 28, 2001, provisional application No. 60/499,026, filed on Aug. 29, 2003, provisional application No. 60/498,768, filed on Aug. 29, 2003, provisional application No. 60/498,968, filed on Aug. 29, 2003, provisional application No. 60/498,709, filed on Aug. 28, 2003, provisional application No. 60/498,896, filed on Aug. 29, 2003, provisional application No. 60/498,708, filed on Aug. 28, 2003.

(51) Int. Cl.
*B22F 7/04* (2006.01)
(52) U.S. Cl. .............................. 419/9; 419/11
(58) Field of Classification Search .................. 419/11, 419/9; 228/121, 121.1
See application file for complete search history.

(56) References Cited

U.S. PATENT DOCUMENTS

| | | | |
|---|---|---|---|
| 2,947,608 A | 8/1960 | Hall | |
| 2,947,609 A | 8/1960 | Strong | |
| 2,947,610 A | 8/1960 | Hall et al. | |
| 2,947,611 A | 8/1960 | Bundy | |
| 2,992,900 A | 7/1961 | Bovenkerk | |
| 3,031,269 A | 4/1962 | Bovenkerk | |
| 3,097,929 A | 7/1963 | Ragan | |
| 3,102,536 A | 9/1963 | Rose et al. | |
| 3,150,413 A | 9/1964 | Zeitlin et al. | |
| 3,201,828 A | 8/1965 | Fryklung | |
| 3,292,997 A | 12/1966 | Strong | |
| 3,297,407 A | 1/1967 | Wentorf, Jr. | |
| 3,407,445 A | 10/1968 | Strong | |
| 3,423,177 A | 1/1969 | Bovenkerk | |
| 3,488,153 A | 1/1970 | Bundy | |
| 3,544,315 A * | 12/1970 | Asgar | 420/436 |
| 3,574,580 A | 4/1971 | Stromberg et al. | |
| 3,584,318 A | 6/1971 | Scales et al. | |
| 3,597,158 A | 8/1971 | Horton | |
| 3,658,056 A | 4/1972 | Huggler et al. | |
| 3,683,421 A | 8/1972 | Martinie | |
| 3,702,573 A | 11/1972 | Nemeth | |
| 3,723,995 A | 4/1973 | Baumann | |
| 3,778,586 A | 12/1973 | Breton et al. | |
| 3,816,085 A | 6/1974 | Hall | |
| 3,819,814 A | 6/1974 | Pope | |
| 3,852,045 A | 12/1974 | Wheeler et al. | |
| 3,864,409 A | 2/1975 | Pope | |
| 3,864,758 A | 2/1975 | Yakich | |
| 3,865,585 A * | 2/1975 | Rademacher | 420/436 |
| 3,871,031 A | 3/1975 | Boutin | |
| 3,894,297 A | 7/1975 | Mittelmeier | |
| 3,977,026 A | 8/1976 | Battault | |
| 4,005,495 A | 2/1977 | Locke et al. | |
| 4,031,570 A | 6/1977 | Frey | |
| 4,055,862 A | 11/1977 | Farling | |
| 4,058,856 A | 11/1977 | Doerre et al. | |
| 4,089,933 A | 5/1978 | Vereschagin et al. | |
| 4,104,344 A | 8/1978 | Pope et al. | |
| 4,104,441 A | 8/1978 | Fedoseev et al. | |
| 4,115,875 A | 9/1978 | Rambert et al. | |
| 4,126,924 A | 11/1978 | Akins et al. | |
| 4,163,769 A | 8/1979 | Pope et al. | |
| 4,164,794 A | 8/1979 | Spector et al. | |

(Continued)

FOREIGN PATENT DOCUMENTS

GB 2 283 772 5/1995

(Continued)

*Primary Examiner*—Roy King
*Assistant Examiner*—Ngoclan T Mai
(74) *Attorney, Agent, or Firm*—Bateman IP Law Group

(57) ABSTRACT

CoCrMo can be used to enhance biocompatibility of a sintered polycrystalline diamond compact.

9 Claims, 62 Drawing Sheets

U.S. PATENT DOCUMENTS

| | | |
|---|---|---|
| 4,166,292 A | 9/1979 | Bokros |
| 4,196,181 A | 4/1980 | Vereschagin et al. |
| 4,206,517 A | 6/1980 | Pappas et al. |
| 4,214,322 A | 7/1980 | Kraus |
| 4,231,762 A | 11/1980 | Hara et al. |
| 4,259,072 A | 3/1981 | Hirabayashi et al. |
| 4,260,397 A | 4/1981 | Bovenkerk |
| 4,268,276 A | 5/1981 | Bovenkerk |
| 4,289,123 A | 9/1981 | Dunn |
| 4,311,490 A | 1/1982 | Bovenkerk et al. |
| D265,204 S | 6/1982 | Turchan et al. |
| 4,332,037 A | 6/1982 | Esformes et al. |
| 4,349,922 A | 9/1982 | Agee |
| 4,380,471 A | 4/1983 | Lee et al. |
| 4,454,612 A | 6/1984 | McDaniel et al. |
| 4,470,158 A | 9/1984 | Pappas et al. |
| 4,518,659 A | 5/1985 | Gigl et al. |
| 4,525,179 A | 6/1985 | Gigl |
| 4,534,934 A | 8/1985 | Cho |
| 4,535,486 A | 8/1985 | Roberts et al. |
| 4,547,910 A | 10/1985 | Roberts et al. |
| 4,592,422 A | 6/1986 | Hipp |
| 4,592,433 A | 6/1986 | Dennis |
| 4,604,106 A | 8/1986 | Hall |
| 4,610,699 A | 9/1986 | Yazu et al. |
| 4,618,269 A | 10/1986 | Badrak et al. |
| 4,651,374 A | 3/1987 | Turchan |
| 4,662,348 A | 5/1987 | Hall et al. |
| 4,687,487 A | 8/1987 | Hintermann |
| 4,693,722 A | 9/1987 | Wall |
| 4,694,918 A | 9/1987 | Hall |
| 4,708,496 A | 11/1987 | McPherson |
| 4,714,473 A | 12/1987 | Bloebaum |
| 4,729,440 A | 3/1988 | Hall |
| 4,731,088 A | 3/1988 | Collier |
| 4,738,322 A | 4/1988 | Hall et al. |
| 4,756,631 A | 7/1988 | Jones |
| 4,759,350 A | 7/1988 | Dunn et al. |
| 4,761,844 A | 8/1988 | Turchan |
| 4,766,040 A | 8/1988 | Hillert et al. |
| 4,778,486 A | 10/1988 | Csillag et al. |
| 4,784,023 A | 11/1988 | Dennis |
| 4,784,662 A | 11/1988 | Muller |
| 4,789,251 A | 12/1988 | McPherson et al. |
| 4,797,009 A | 1/1989 | Yamazaki |
| 4,797,241 A | 1/1989 | Peterson et al. |
| 4,797,326 A | 1/1989 | Csillag |
| 4,808,185 A | 2/1989 | Penenberg et al. |
| 4,813,959 A | 3/1989 | Cremascoli |
| 4,822,355 A | 4/1989 | Bhuvaneshwar |
| 4,822,368 A | 4/1989 | Collier |
| 4,824,442 A | 4/1989 | Cerceau |
| 4,830,824 A * | 5/1989 | Lindigkeit .................. 420/436 |
| 4,840,631 A | 6/1989 | Mathys |
| 4,842,605 A | 6/1989 | Sonnerat et al. |
| 4,846,839 A | 7/1989 | Noiles |
| 4,861,350 A | 8/1989 | Phaal et al. |
| 4,865,603 A | 9/1989 | Noiles |
| 4,865,606 A | 9/1989 | Rehder |
| 4,866,885 A | 9/1989 | Dodsworth |
| 4,878,917 A | 11/1989 | Kranz et al. |
| 4,892,547 A | 1/1990 | Brown |
| 4,922,298 A | 5/1990 | Folkins et al. |
| 4,922,898 A | 5/1990 | Dunn |
| 4,925,701 A | 5/1990 | Jansen et al. |
| 4,931,068 A | 6/1990 | Dismukes et al. |
| 4,934,040 A | 6/1990 | Turchan |
| 4,935,200 A | 6/1990 | LaSalle et al. |
| 4,940,404 A | 7/1990 | Ammon et al. |
| 4,944,756 A | 7/1990 | Kenna |
| 4,957,510 A | 9/1990 | Cremascoli |
| 4,959,066 A | 9/1990 | Dunn et al. |
| 4,959,071 A | 9/1990 | Brown et al. |
| 4,961,383 A | 10/1990 | Fishman et al. |
| 4,964,766 A | 10/1990 | Turchan et al. |
| 4,964,868 A | 10/1990 | Bloebaum |
| 4,966,750 A | 10/1990 | LaSalle et al. |
| 4,969,910 A | 11/1990 | Frey et al. |
| 4,979,957 A | 12/1990 | Hodorek |
| 5,002,578 A | 3/1991 | Luman |
| 5,002,579 A | 3/1991 | Copf et al. |
| 5,002,580 A | 3/1991 | Noble et al. |
| 5,002,581 A | 3/1991 | Paxson et al. |
| 5,009,673 A | 4/1991 | Cho |
| 5,011,515 A | 4/1991 | Frushour |
| 5,019,103 A | 5/1991 | Van Zile et al. |
| 5,022,894 A | 6/1991 | Vagarali et al. |
| 5,030,233 A | 7/1991 | Ducheyne |
| 5,037,423 A | 8/1991 | Kenna |
| 5,037,439 A | 8/1991 | Albrektsson et al. |
| 5,037,451 A | 8/1991 | Burnand et al. |
| 5,047,060 A | 9/1991 | Henssge et al. |
| 5,047,062 A | 9/1991 | Pappas et al. |
| 5,052,339 A | 10/1991 | Vakeris et al. |
| 5,054,246 A | 10/1991 | Phaal et al. |
| 5,054,682 A | 10/1991 | Mistry |
| 5,055,318 A | 10/1991 | Deutchman et al. |
| 5,067,826 A | 11/1991 | Lemelson |
| RE33,767 E | 12/1991 | Christini et al. |
| 5,080,685 A | 1/1992 | Bolesky et al. |
| 5,080,752 A | 1/1992 | Kabacoff et al. |
| 5,082,359 A | 1/1992 | Kirkpatrick |
| 5,092,687 A | 3/1992 | Hall |
| 5,092,895 A | 3/1992 | Albrektsson et al. |
| 5,092,898 A | 3/1992 | Bekki et al. |
| 5,108,432 A | 4/1992 | Gustavson |
| 5,108,451 A | 4/1992 | Forte |
| 5,108,452 A | 4/1992 | DeMane et al. |
| 5,116,380 A | 5/1992 | Hewka et al. |
| 5,120,327 A | 6/1992 | Dennis |
| 5,127,923 A | 7/1992 | Bunting et al. |
| 5,128,146 A | 7/1992 | Hirayama et al. |
| 5,133,757 A | 7/1992 | Sioshansi et al. |
| 5,133,758 A | 7/1992 | Hollister |
| 5,133,763 A | 7/1992 | Mullers |
| 5,152,794 A | 10/1992 | Davidson |
| 5,152,795 A | 10/1992 | Soishansi et al. |
| 5,154,023 A | 10/1992 | Sioshansi |
| 5,154,245 A * | 10/1992 | Waldenstrom et al. ... 175/420.2 |
| 5,156,624 A | 10/1992 | Barnes |
| 5,163,963 A | 11/1992 | Hewka et al. |
| 5,171,282 A | 12/1992 | Pequignot |
| 5,171,283 A | 12/1992 | Pappas et al. |
| 5,181,926 A | 1/1993 | Koch et al. |
| 5,181,928 A | 1/1993 | Bolesky et al. |
| 5,192,323 A | 3/1993 | Shetty et al. |
| 5,194,066 A | 3/1993 | Van Zile |
| 5,197,987 A | 3/1993 | Koch et al. |
| 5,211,726 A | 5/1993 | Slutz et al. |
| 5,217,081 A | 6/1993 | Waldenstrom et al. |
| 5,248,317 A | 9/1993 | Tank et al. |
| 5,258,022 A | 11/1993 | Davidson |
| 5,258,033 A | 11/1993 | Lawes et al. |
| 5,264,283 A | 11/1993 | Waldenstrom et al. |
| 5,284,483 A | 2/1994 | Johnson et al. |
| 5,304,192 A | 4/1994 | Crouse |
| 5,308,412 A * | 5/1994 | Shetty et al. ................. 148/238 |
| 5,310,408 A | 5/1994 | Schryver et al. |
| 5,322,735 A | 6/1994 | Fridez et al. |
| 5,326,361 A | 7/1994 | Hollister |
| 5,326,362 A | 7/1994 | Shetty et al. |
| 5,330,481 A | 7/1994 | Hood et al. |
| 5,330,532 A | 7/1994 | Ranawat |
| 5,330,826 A | 7/1994 | Taylor et al. |

| | | | | | |
|---|---|---|---|---|---|
| 5,333,954 A | 8/1994 | Noguchi et al. | 5,571,195 A | 11/1996 | Johnson |
| 5,335,738 A | 8/1994 | Waldenstrom et al. | 5,571,203 A | 11/1996 | Masini |
| 5,348,108 A | 9/1994 | Scott et al. | 5,571,616 A | 11/1996 | Phillips et al. |
| 5,351,772 A | 10/1994 | Smith | 5,590,727 A | 1/1997 | Tank et al. |
| 5,355,750 A | 10/1994 | Scott et al. | 5,590,728 A | 1/1997 | Matthias et al. |
| 5,355,969 A | 10/1994 | Hardy et al. | 5,590,729 A | 1/1997 | Cooley et al. |
| 5,358,525 A | 10/1994 | Fox et al. | 5,591,233 A | 1/1997 | Kelman et al. |
| 5,358,529 A | 10/1994 | Davidson | 5,593,234 A | 1/1997 | Liston |
| 5,358,532 A | 10/1994 | Evans et al. | 5,593,719 A | 1/1997 | Dearnaley et al. |
| 5,360,341 A | 11/1994 | Abramowitz | 5,601,477 A | 2/1997 | Bunting et al. |
| 5,364,192 A | 11/1994 | Damm et al. | 5,605,198 A | 2/1997 | Tibbitts et al. |
| 5,368,398 A | 11/1994 | Damm et al. | 5,605,199 A | 2/1997 | Newton |
| 5,370,694 A | 12/1994 | Davidson | 5,605,714 A | 2/1997 | Dearnaley et al. |
| 5,370,700 A | 12/1994 | Sarkisian et al. | 5,605,938 A | 2/1997 | Roufa et al. |
| 5,370,717 A | 12/1994 | Lloyd et al. | 5,611,649 A | 3/1997 | Matthias |
| 5,372,660 A | 12/1994 | Davidson et al. | 5,617,928 A | 4/1997 | Matthias et al. |
| 5,376,444 A | 12/1994 | Grotenpass et al. | 5,620,285 A | 4/1997 | Turchan |
| 5,379,853 A | 1/1995 | Lockwood et al. | 5,620,754 A | 4/1997 | Turchan et al. |
| 5,379,854 A | 1/1995 | Dennis | 5,621,965 A | 4/1997 | Turchan |
| 5,380,547 A | 1/1995 | Higgins | 5,622,233 A | 4/1997 | Griffin |
| 5,383,934 A | 1/1995 | Armini et al. | 5,624,068 A | 4/1997 | Waldenstrom et al. |
| 5,387,247 A | 2/1995 | Vallana et al. | 5,630,479 A | 5/1997 | Dennis |
| 5,391,407 A | 2/1995 | Dearnaley | 5,633,087 A | 5/1997 | Simpson |
| 5,391,408 A | 2/1995 | Piera | 5,635,243 A | 6/1997 | Turchan et al. |
| 5,391,422 A | 2/1995 | Omori et al. | 5,641,323 A | 6/1997 | Caldarise |
| 5,401,269 A | 3/1995 | Buttner-Janz et al. | 5,641,324 A | 6/1997 | Bokros et al. |
| 5,405,394 A | 4/1995 | Davidson | 5,641,921 A | 6/1997 | Dennis et al. |
| 5,411,555 A | 5/1995 | Nieder | 5,643,641 A | 7/1997 | Turchan et al. |
| 5,413,438 A | 5/1995 | Turchan | 5,645,601 A * | 7/1997 | Pope et al. ............... 623/23.39 |
| 5,413,814 A | 5/1995 | Bowen et al. | 5,645,605 A | 7/1997 | Klawitter |
| 5,414,049 A | 5/1995 | Sun et al. | 5,647,449 A | 7/1997 | Dennis |
| 5,415,704 A | 5/1995 | Davidson | 5,647,704 A | 7/1997 | Turchan |
| 5,421,425 A | 6/1995 | Griffin | 5,648,127 A | 7/1997 | Turchan et al. |
| 5,429,459 A | 7/1995 | Palm | 5,660,075 A | 8/1997 | Johnson et al. |
| 5,429,883 A | 7/1995 | Sasaki et al. | 5,667,028 A | 9/1997 | Truax et al. |
| 5,435,403 A | 7/1995 | Tibbitts | 5,669,271 A | 9/1997 | Griffin et al. |
| 5,441,488 A | 8/1995 | Shimura et al. | 5,669,913 A | 9/1997 | Zobel |
| 5,449,048 A | 9/1995 | Thigpen et al. | 5,676,632 A | 10/1997 | Davidson |
| 5,451,365 A | 9/1995 | Barsoum | 5,676,704 A | 10/1997 | Ries et al. |
| 5,458,827 A | 10/1995 | Holly | 5,677,061 A | 10/1997 | Ely et al. |
| 5,469,927 A | 11/1995 | Griffin | 5,683,442 A | 11/1997 | Davidson |
| 5,478,906 A | 12/1995 | Howard, Jr. | 5,685,306 A | 11/1997 | Davidson |
| 5,485,496 A | 1/1996 | Lee et al. | 5,685,671 A | 11/1997 | Packer et al. |
| 5,486,137 A | 1/1996 | Flood et al. | 5,690,670 A | 11/1997 | Davidson |
| 5,492,188 A | 2/1996 | Smith et al. | 5,693,090 A | 12/1997 | Unsworth et al. |
| 5,494,477 A | 2/1996 | Flood et al. | 5,702,448 A | 12/1997 | Buechel et al. |
| 5,496,318 A | 3/1996 | Howland et al. | 5,702,473 A | 12/1997 | Albrektsson et al. |
| 5,498,081 A | 3/1996 | Dennis et al. | 5,702,487 A | 12/1997 | Averill et al. |
| 5,498,302 A | 3/1996 | Davidson | 5,706,906 A | 1/1998 | Jurewicz et al. |
| 5,499,688 A | 3/1996 | Dennis | 5,713,947 A | 2/1998 | Davidson |
| 5,507,804 A | 4/1996 | Llanos | 5,716,400 A | 2/1998 | Davidson |
| 5,507,814 A | 4/1996 | Gilbert et al. | 5,725,573 A | 3/1998 | Dearnaley et al. |
| 5,507,824 A | 4/1996 | Lennox | 5,725,582 A | 3/1998 | Bevan et al. |
| 5,507,830 A | 4/1996 | DeMane et al. | 5,728,161 A | 3/1998 | Camino et al. |
| 5,508,368 A | 4/1996 | Knapp et al. | 5,755,800 A | 5/1998 | O'Neil et al. |
| 5,512,235 A | 4/1996 | Cerutti et al. | 5,766,255 A | 6/1998 | Slamin et al. |
| RE35,255 E | 5/1996 | Turchan | 5,766,394 A | 6/1998 | Anderson et al. |
| 5,514,182 A | 5/1996 | Shea | 5,769,891 A | 6/1998 | Clayton |
| 5,514,184 A | 5/1996 | Doi et al. | 5,773,140 A | 6/1998 | Cerutti et al. |
| 5,514,193 A | 5/1996 | Schaal et al. | 5,782,910 A | 7/1998 | Davidson |
| 5,516,500 A | 5/1996 | Liu et al. | 5,787,022 A | 7/1998 | Tibbitts et al. |
| 5,518,969 A | 5/1996 | Ragan | 5,800,560 A | 9/1998 | Draenert |
| 5,525,537 A | 6/1996 | Zachai et al. | 5,824,062 A | 10/1998 | Patke et al. |
| 5,530,072 A | 6/1996 | Shirodkar | 5,824,101 A | 10/1998 | Pappas |
| 5,544,713 A | 8/1996 | Dennis | 5,824,651 A | 10/1998 | Nanci et al. |
| 5,549,190 A | 8/1996 | Turchan | 5,830,539 A | 11/1998 | Yan et al. |
| 5,549,690 A | 8/1996 | Hollister et al. | 5,855,601 A | 1/1999 | Bessler et al. |
| 5,549,700 A | 8/1996 | Graham et al. | 5,855,996 A | 1/1999 | Corrigan et al. |
| 5,554,415 A | 9/1996 | Turchan et al. | 5,861,042 A | 1/1999 | Buechel et al. |
| 5,556,464 A | 9/1996 | Tanabe et al. | 5,868,796 A | 2/1999 | Buechel et al. |
| 5,560,716 A | 10/1996 | Tank et al. | 5,868,885 A | 2/1999 | Crockett et al. |
| 5,564,511 A | 10/1996 | Frushour | 5,875,862 A | 3/1999 | Jurewicz et al. |
| 5,566,779 A | 10/1996 | Dennis | 5,876,459 A | 3/1999 | Powell |

| | | |
|---|---|---|
| 5,879,397 A | 3/1999 | Kalberer et al. |
| 5,879,404 A | 3/1999 | Bateman et al. |
| 5,879,405 A | 3/1999 | Ries et al. |
| 5,879,407 A | 3/1999 | Waggener |
| 5,888,208 A | 3/1999 | Ro |
| 5,895,388 A | 4/1999 | Zobel |
| 5,898,388 A | 4/1999 | Hofmann et al. |
| 5,906,644 A | 5/1999 | Powell |
| 5,924,501 A | 7/1999 | Tibbitts |
| 5,928,131 A | 7/1999 | Prem |
| 5,944,129 A | 8/1999 | Jensen |
| 5,950,747 A | 9/1999 | Tibbitts et al. |
| 5,979,579 A | 11/1999 | Jurewicz |
| 5,981,827 A | 11/1999 | Devlin et al. |
| 6,000,483 A | 12/1999 | Jurewicz et al. |
| 6,006,846 A | 12/1999 | Tibbitts et al. |
| 6,007,577 A | 12/1999 | Vanney et al. |
| 6,021,859 A | 2/2000 | Tibbitts et al. |
| 6,045,497 A | 4/2000 | Schweich, Jr. et al. |
| 6,045,877 A | 4/2000 | Gleason et al. |
| 6,053,729 A * | 4/2000 | Brehm et al. .................. 433/9 |
| 6,068,071 A | 5/2000 | Jurewicz |
| 6,077,148 A | 6/2000 | Klein et al. |
| 6,082,223 A | 7/2000 | Tibbitts |
| 6,132,675 A * | 10/2000 | Corrigan et al. ............... 419/11 |
| 6,319,460 B1 * | 11/2001 | Fang .......................... 419/32 |
| 6,773,520 B1 * | 8/2004 | Fehring et al. .............. 148/425 |

FOREIGN PATENT DOCUMENTS

| | | |
|---|---|---|
| GB | 2 290 326 | 12/1995 |
| GB | 2 290 327 | 12/1995 |
| GB | 2 290 328 | 12/1995 |

* cited by examiner

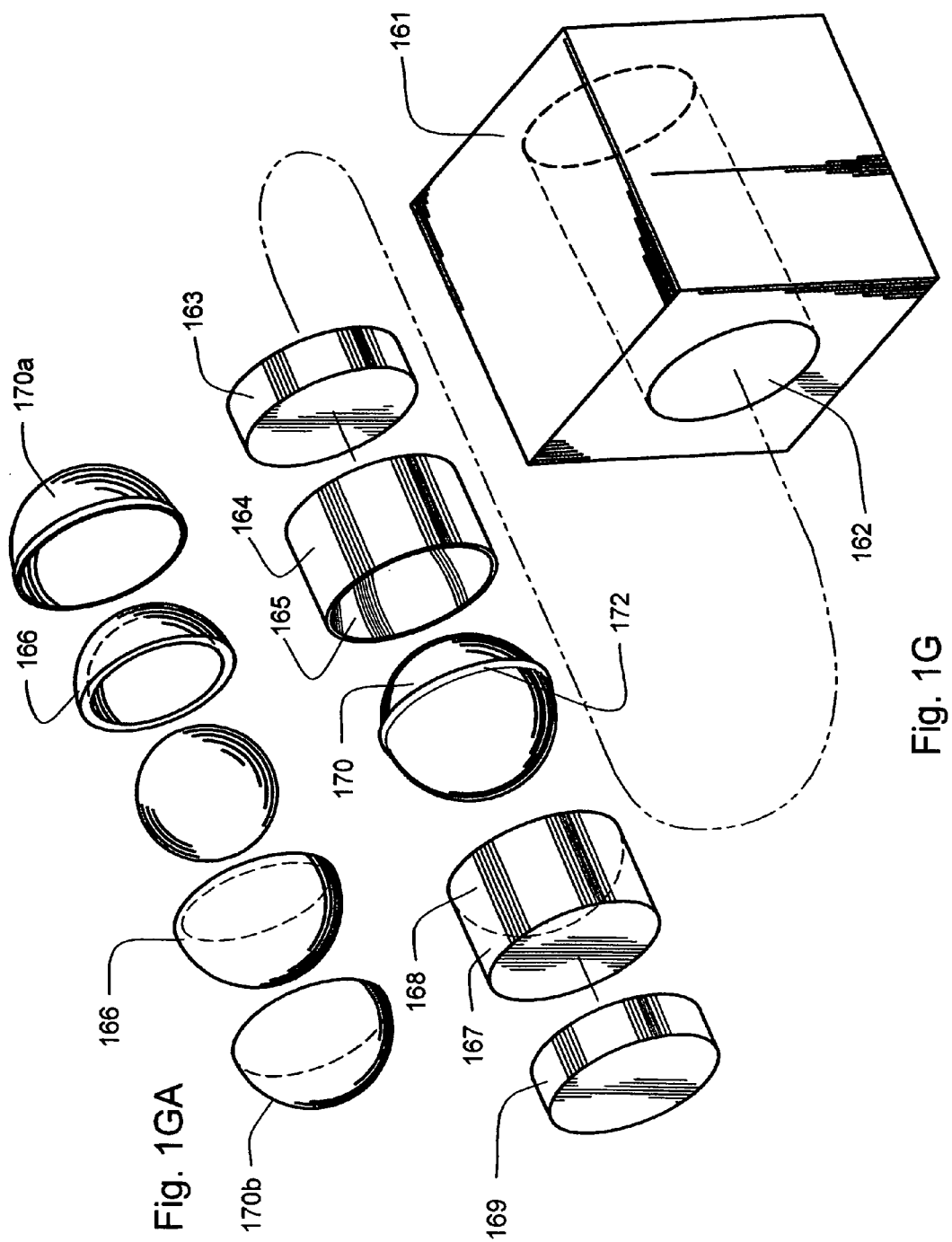

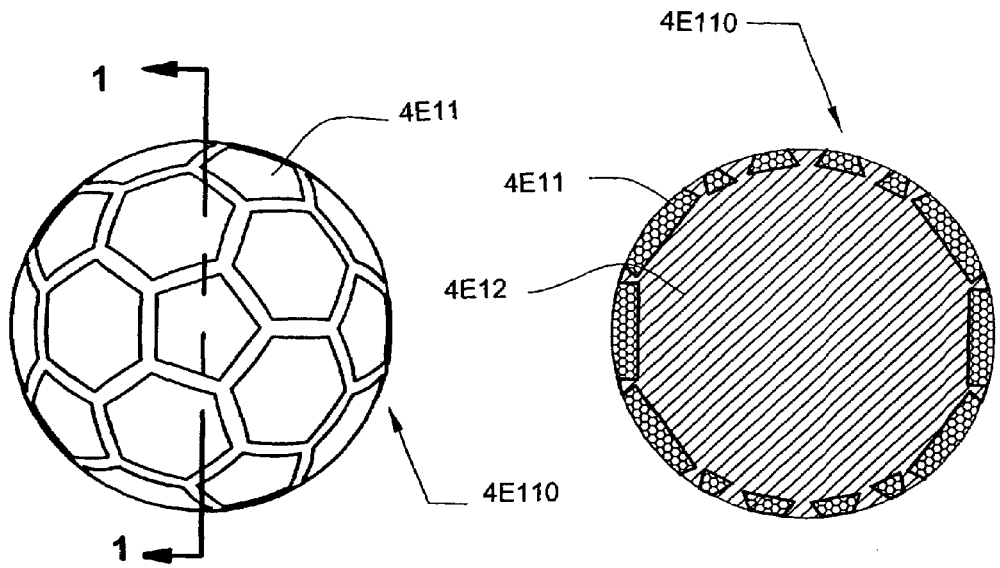
FIG. 4F-1    FIG. 4F
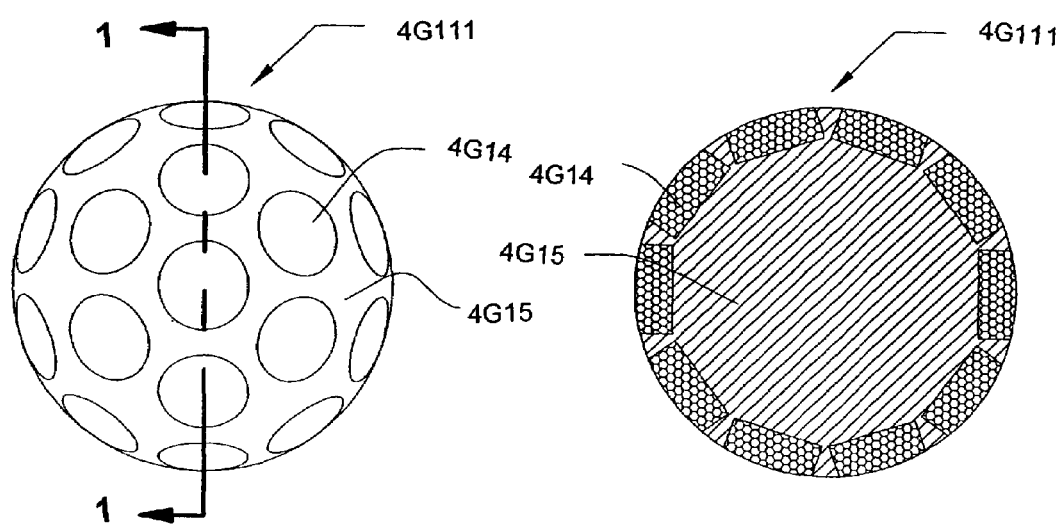
FIG. 4G    FIG. 4G-1

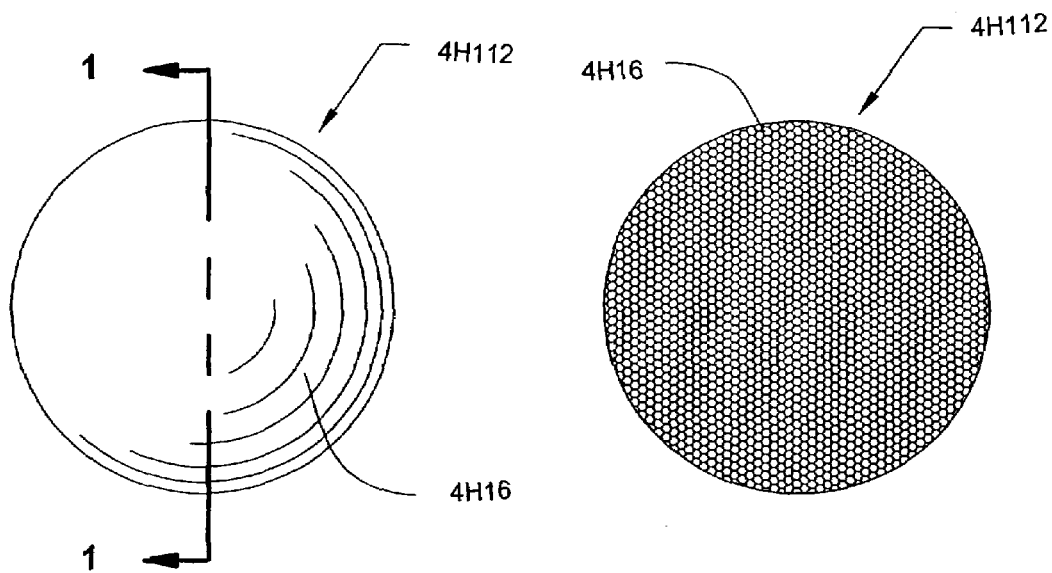
FIG. 4H          FIG. 4H1
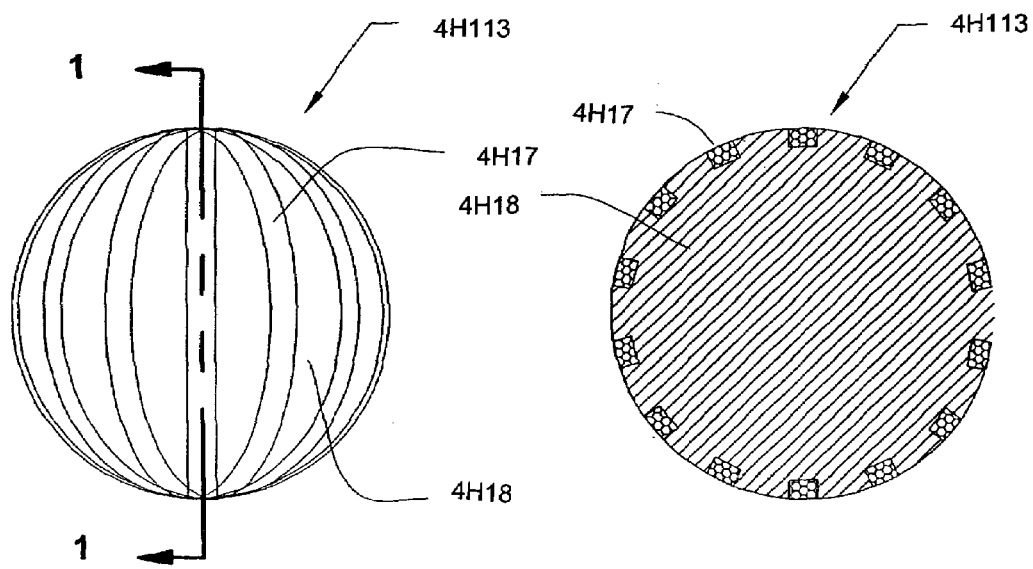
FIG. 4I          FIG. 4I1

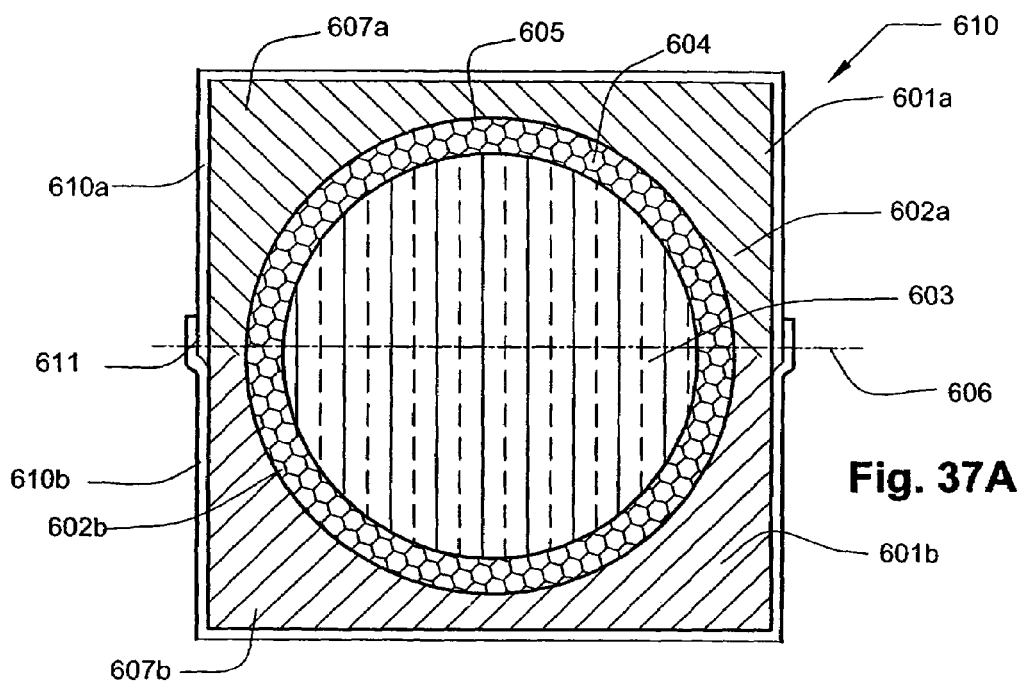
Fig. 37A
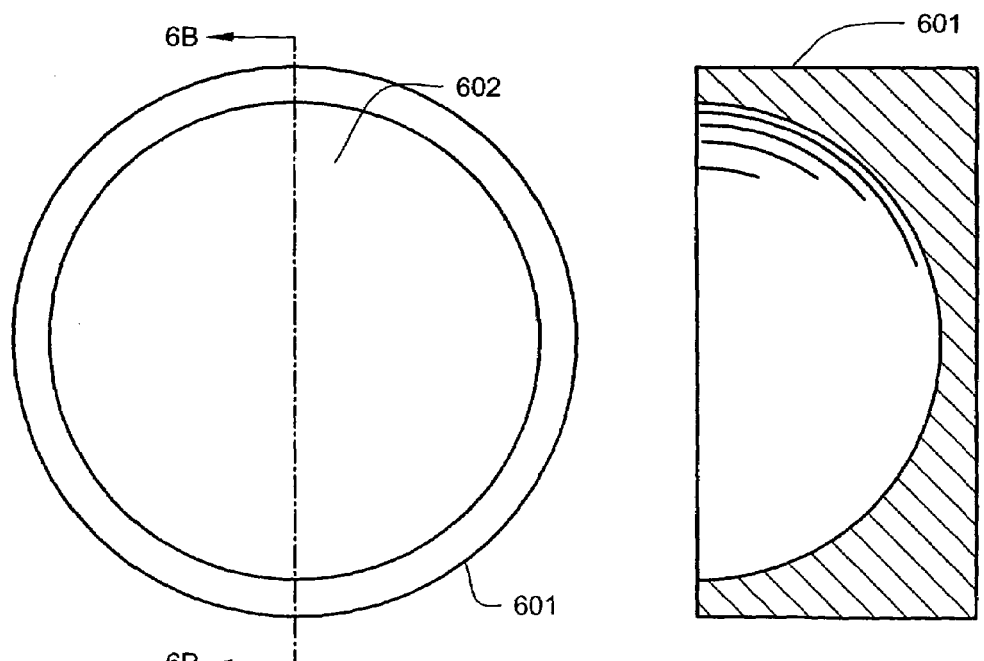
Fig. 37B
Fig. 37C

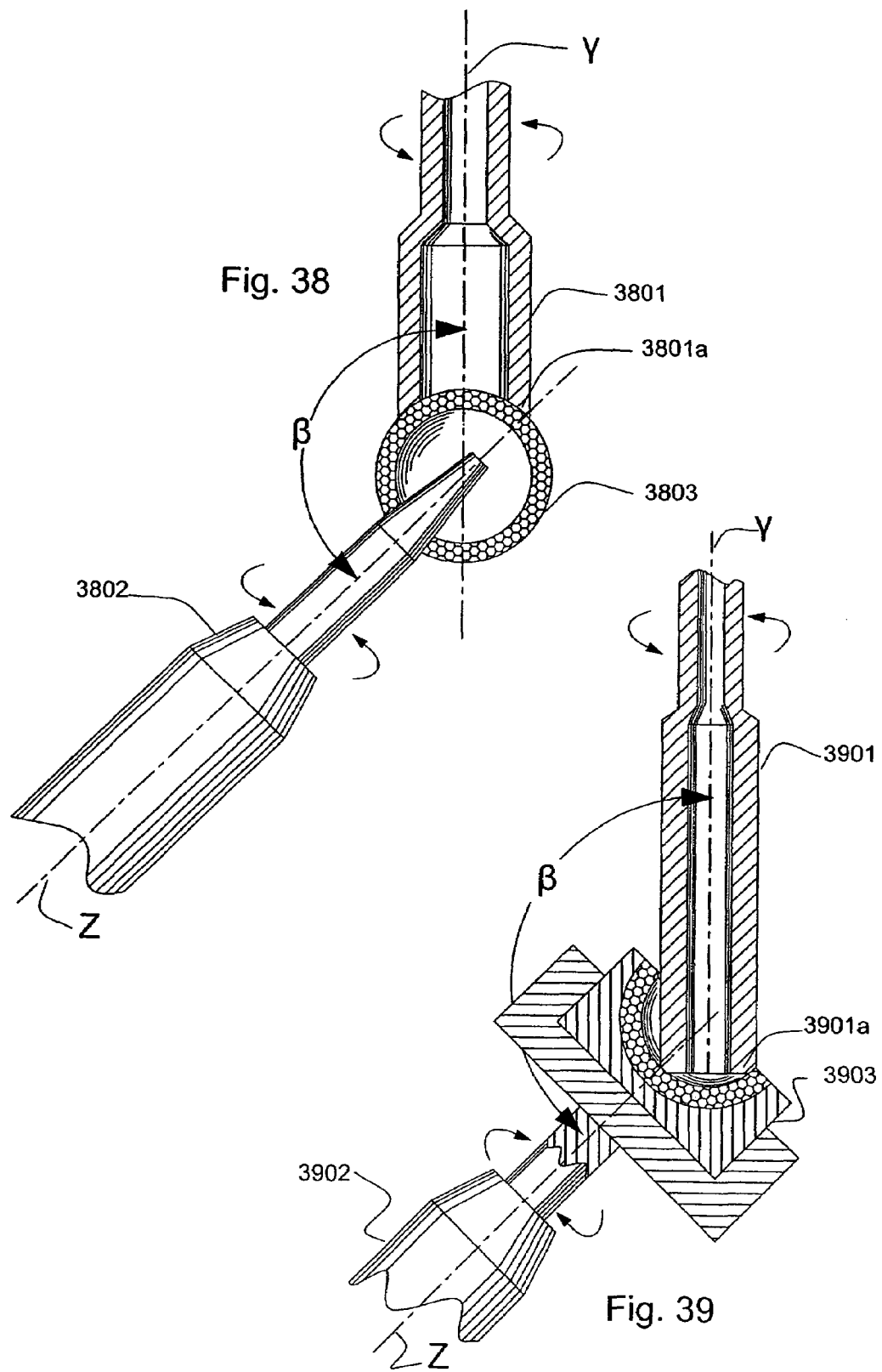

USE OF COCRMO TO AUGMENT BIOCOMPATIBILITY IN POLYCRYSTALLINE DIAMOND COMPACTS

CROSS REFERENCE TO RELATED APPLICATIONS

This patent application is a continuation-in-part of U.S. patent application Ser. No. 10/259,187 filed on Sep. 28, 2002, now abandoned which is a continuation-in-part of U.S. patent application Ser. No. 10/229,907 filed on Aug. 28, 2002 (which claims priority U.S. Provisional Patent Application Ser. No. 60/325,832 filed on Sep. 28, 2001), which is a continuation-in-part of U.S. patent application Ser. No. 09/494,276 filed on Jan. 30, 2000, now U.S. Pat. No. 6,488,715, which is a continuation-in-part of U.S. patent application Ser. No. 09/457,226 filed on Dec. 8, 1999, now abandoned, which is a continuation-in-part of U.S. patent application Ser. No. 08/844,395 filed on Apr. 18, 1997, now U.S. Pat. No. 6,010,633, which is a continuation of U.S. patent application Ser. No. 08/631,877 filed on Apr. 16, 1996, now U.S. Pat. No. 5,645,601, which is a continuation of U.S. patent application Ser. No. 08/289,696 filed on Aug. 12, 1994, now abandoned, and priority is claimed to all of the foregoing.

This patent application claims priority to U.S. Provisional Patent Application Ser. 60/499,026 filed on Aug. 29, 2003; to U.S. Provisional Patent Application Ser. No. 60/498,768 filed on Aug. 29, 2003; to U.S. Provisional Patent Application Ser. No. 60/498,968 filed on Aug. 29, 2003, to U.S. Provisional Patent Application Ser. No. 60/498,709 filed on Aug. 28, 2003, to U.S. Provisional Patent Application Ser. No. 60/498,896 filed on Aug. 29, 2003 and to U.S. Provisional Patent Application Ser. No. 60/498,708 filed on Aug. 28, 2003. Each of the foregoing is hereby incorporated by reference.

BACKGROUND

This disclosure relates to methods, materials and apparatuses for making superhard (i.e., polycrystalline diamond and polycrystalline cubic boron nitride) components, and other hard components.

SUMMARY

Various methods, materials and apparatuses for making superhard components and other hard components are disclosed.

BRIEF DESCRIPTION OF DRAWINGS

FIG. 1BB depicts a sintered PDC in which there is a continuous gradient transition from substrate metal through the diamond table.

FIGS. 1G and 1GA depict a precompaction assembly, which may be used to reduce free space in diamond feedstock prior to sintering.

FIGS. 4A-4I1 depict some example superhard constructs.

FIGS. 5-12 depict preparation of superhard materials for use in making an articulating diamond-surfaced spinal implant component.

FIGS. 37a-37c depict sintering of arcuate superhard surfaces.

FIGS. 38-50 depict machining and finishing superhard articulating diamond-surfaced spinal implant components.

DETAILED DESCRIPTION

Figure 1A:
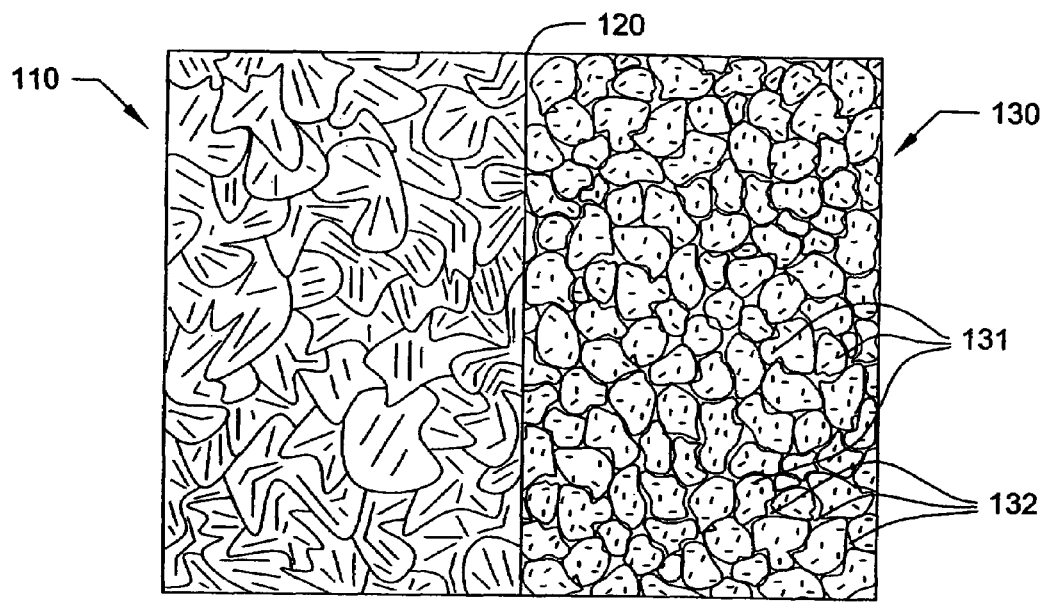
FIG. 1A depicts a quantity of diamond feedstock adjacent to a metal alloy substrate prior to sintering of the diamond feedstock and the substrate to create a PDC.

Reference will now be made to the drawings in which the various elements of the embodiments will be discussed. Persons skilled in the design of prosthetic joints and other bearing surfaces will understand the application of the various embodiments and their principles to sintering and hipping of superhard and hard components, including those used in prosthetic joints of all types, and components of prosthetic joints, anywhere hard, durable or biocompatabile products are desired, and for devices other than those exemplified herein.

Various embodiments of the manufacturing systems, devices, processes and materials disclosed herein relate to superhard and hard surfaces and components. More specifically, some relate to diamond and sintered polycrystalline diamond surfaces (PCD). Some embodiments make or utilize a polycrystalline diamond compact (PDC) to provide a very strong, low friction, long-wearing, biocompatible part or surface. Any surface or devices that experiences wear and requires strength and durability will benefit from the advances made here.

The table below provides a comparison of sintered PCD to some other materials.

TABLE 1

COMPARISON OF SINTERED PCD TO OTHER MATERIALS

| Material | Specific Gravity | Hardness (Knoop) | Thermal Conductivity (W/m K) | Coefficient of Thermal Expansion ("CTE") ($\times 10^{-6}$) |
|---|---|---|---|---|
| Sintered Polycrystalline Diamond Compact (PDC) | 3.5-4.0 | 9000 | 900 | 1.50-4.8 |
| Cubic Boron Nitride | 3.48 | 4500 | 800 | 1.0-4.0 |
| Silicon Carbide | 3.00 | 2500 | 84 | 4.7-5.3 |
| Aluminum Oxide | 3.50 | 2000 | | 7.8-8.8 |
| Tungsten Carbide (10% Co) | 14.6 | 2200 | 112 | 4-6 |
| Cobalt Chrome | 8.2 | 43 RC | | 16.9 |
| Ti6Al4V | 4.43 | | 6.6-17.5 | 11 |
| Silicon Nitride | 3.2 | 14.2 | 15-7 | 1.8-3.7 |

In view of the superior hardness of sintered PCD, it is expected that sintered PCD will provide improved wear and durability characteristics.

In a PDC, the diamond table is chemically bonded and mechanically fixed to the substrate in a manufacturing process that typically uses a combination of high pressure and high temperature to form the sintered PCD (see, infra). The chemical bonds between the diamond table and the substrate are established during the sintering process by combinations of unsatisfied sp3 carbon bonds with unsatisfied substrate metal bonds. The mechanical fixation is a result of shape of the substrate and diamond table and differences in the physical properties of the substrate and the diamond table as well as the gradient interface between the substrate and the diamond table. The resulting sintered PDC forms a durable modular bearing inserts and joints.

The diamond table may be polished to a very smooth and glass-like finish to achieve a very low coefficient of friction. The high surface energy of sintered PDC causes it to work very well as a load-bearing and articulation surface when a lubricating fluid is present. Its inherent nature allows it to perform very well when a lubricant is absent as well.

While there is discussion herein concerning PDCs, the following materials could be considered for forming prosthetic joint components: polycrystalline diamond, monocrystal diamond, natural diamond, diamond created by physical vapor deposition, diamond created by chemical vapor deposition, diamond like carbon, carbonado, cubic boron nitride, hexagonal boron nitride, or a combination of these, cobalt, chromium, titanium, vanadium, stainless steel, niobium, aluminum, nickel, hafnium, silicon, tungsten, molybdenum, aluminum, zirconium, nitinol, cobalt chrome, cobalt chrome molybdenum, cobalt chrome tungsten, tungsten carbide, titanium carbide, tantalum carbide, zirconium carbide, hafnium carbide, Ti6/4, silicon carbide, chrome carbide, vanadium carbide, yttria stabilized zirconia, magnesia stabilized zirconia, zirconia toughened alumina, titanium molybdenum hafnium, alloys including one or more of the above metals, ceramics, quartz, garnet, sapphire, combinations of these materials, combinations of these and other materials, and other materials may also be used for a desired surface.

Sintered Polycrystalline Diamond Compacts

One useful material for manufacturing joint bearing surfaces is a sintered polycrystalline diamond compact. Diamond has the greatest hardness and the lowest coefficient of friction of any currently known material. Sintered PDCs are chemically inert, are impervious to all solvents, and have the highest thermal conductivity at room temperature of any known material.

In some embodiments, a PDC provides unique chemical bonding and mechanical grip between the diamond and the substrate material. A PDC, which utilizes a substrate material, will have a chemical bond between substrate material and the diamond crystals. The result of this structure is an extremely strong bond between the substrate and the diamond table.

Figure 1B:
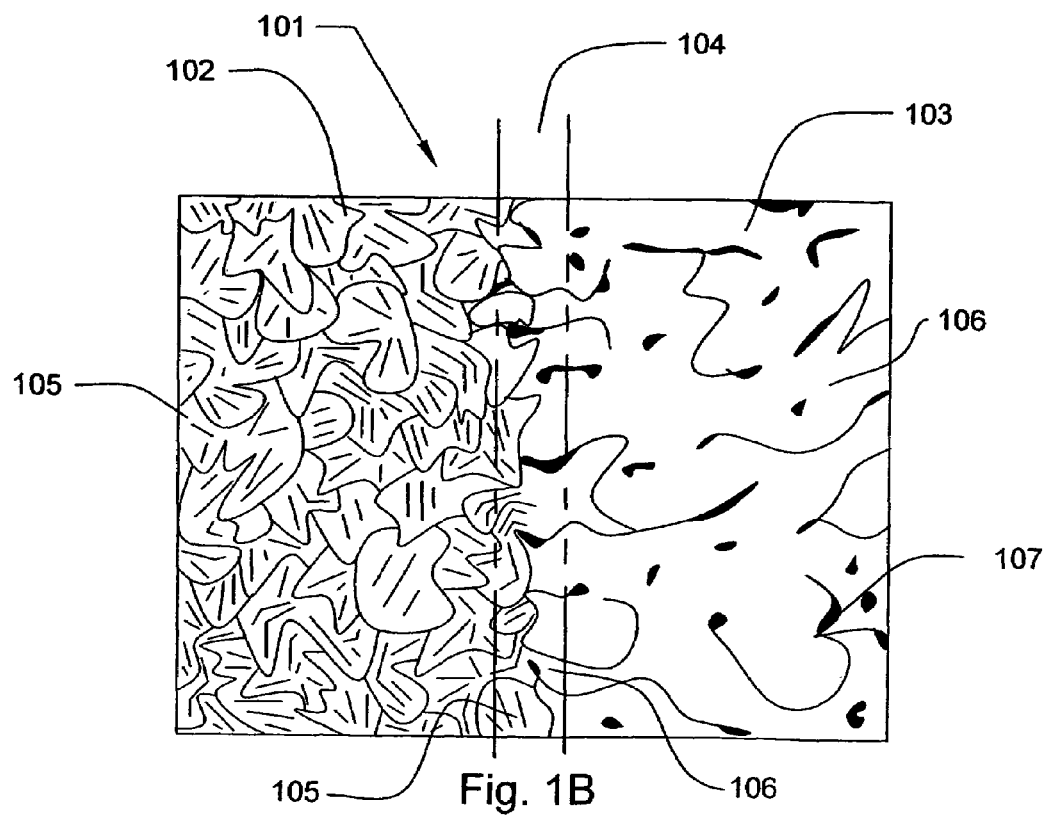
FIG. 1B depicts a sintered PDC in which the diamond table, the substrate, and the transition zone between the diamond table and the substrate are shown.
Figure 1B:
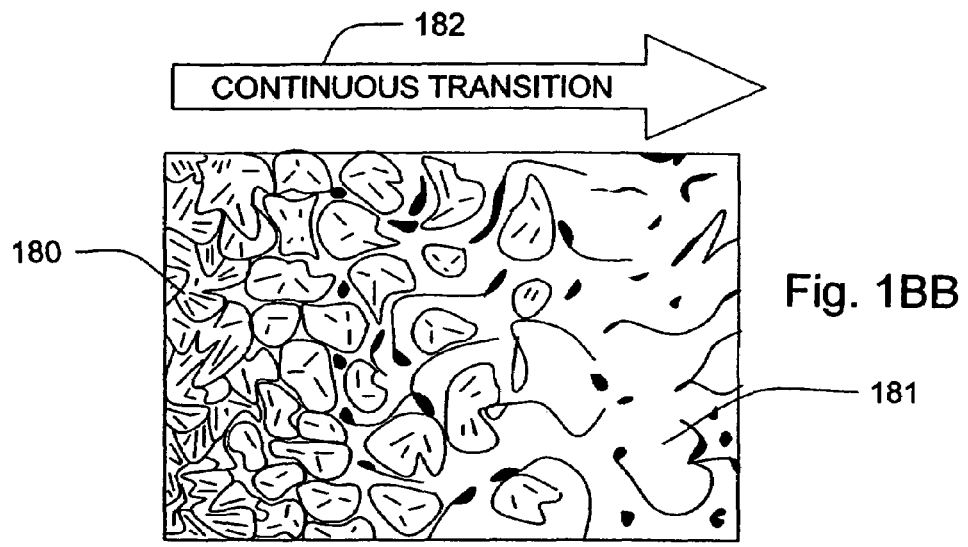

A method by which PDC may be manufactured is described later in this document. Briefly, it involves sintering diamond crystals to each other, and to a substrate under high pressure and high temperature. FIGS. 1A and 1B illustrate the physical and chemical processes involved manufacturing PDCs.

In FIG. 1A, a quantity of diamond feedstock 130 (such as diamond powder or crystals) is placed adjacent to a metal-containing substrate 110 prior to sintering. In the region of the diamond feedstock 130, individual diamond crystals 131 may be seen, and between the individual diamond crystals 131 there are interstitial spaces 132. If desired, a quantity of solvent-catalyst metal may be placed into the interstitial spaces 132. The substrate may also contain solvent-catalyst metal.

The substrate 110 may be a suitable pure metal or alloy, or a cemented carbide containing a suitable metal or alloy as a cementing agent such as cobalt-cemented tungsten carbide or other materials mentioned herein. The substrate 110 may be a metal with high tensile strength. In a cobalt-chrome substrate, the cobalt-chrome alloy will serve as a solvent-catalyst metal for solvating diamond crystals during the sintering process.

The illustration shows the individual diamond crystals and the contiguous metal crystals in the metal substrate. The interface 120 between diamond powder and substrate material is a region where bonding of the diamond table to the substrate must occur. In some embodiments, a boundary layer of a third material different than the diamond and the substrate is placed at the interface 120. This interface boundary layer material, when present, may serve several functions including, but not limited to, enhancing the bond of the diamond table to the substrate, and mitigation of the residual stress field at the diamond-substrate interface.

Once diamond powder or crystals and substrate are assembled as shown in FIG. 1A, the assembly is subjected to high pressure and high temperature as described later herein in order to cause bonding of diamond crystals to diamond crystals and to the substrate. The resulting structure of sintered polycrystalline diamond table bonded to a substrate is called a polycrystalline diamond compact or a PDC. A compact, as the term is used herein, is a composite structure of two different materials, such as diamond crystals, and a substrate metal. The analogous structure incorporating cubic boron nitride crystals in the sintering process instead of diamond crystals is called polycrystalline cubic boron nitride compact (PCBNC). Many of the processes described herein for the fabrication and finishing of PDC structures and parts work in a similar fashion for PCBNC. In some embodiments, PCBNC may be substituted for PDC. It should be noted that a PDC can also be made from free standing diamond without a separate substrate, as described elsewhere herein.

FIG. 1B depicts a PDC 101 after the high pressure and high temperature sintering of diamond feedstock to a substrate. Within the PDC structure, there is an identifiable volume of substrate 102, an identifiable volume of diamond table 103, and a transition zone 104 between diamond table and substrate containing diamond crystals and substrate material. Crystalline grains of substrate material 105 and sintered crystals of diamond 106 are depicted.

On casual examination, the finished compact of FIG. 1B will appear to consist of a solid table of diamond 103 attached to the substrate 102 with a discrete boundary. On very close examination, however, a transition zone 104 between diamond table 103 and substrate 102 can be characterized. This zone represents a gradient interface between diamond table and substrate with a gradual transition of ratios between diamond content and metal content. At the substrate side of the transition zone, there will be only a small percentage of diamond crystals and a high percentage of substrate metal, and on the diamond table side, there will be a high percentage of diamond crystals and a low percentage of substrate metal. Because of this gradual transition of ratios of polycrystalline diamond to substrate metal in the transition zone, the diamond table and the substrate have a gradient interface.

In the transition zone or gradient transition zone where diamond crystals and substrate metal are intermingled, chemical bonds are formed between the diamond and metal. From the transition zone 104 into the diamond table 103, the metal content diminishes and is limited to solvent-catalyst metal that fills the three-dimensional vein-like structure of interstitial voids, openings or asperities 107 within the sintered diamond table structure 103. The solvent-catalyst metal found in the voids or openings 107 may have been swept up from the substrate during sintering or may have been solvent-catalyst metal added to the diamond feedstock before sintering.

During the sintering process, there are three types of chemical bonds that are created: diamond-to-diamond bonds, diamond-to-metal bonds, and metal-to-metal bonds. In the diamond table, there are diamond-to-diamond bonds (sp3 carbon bonds) created when diamond particles partially solvate in the solvate-catalyst metal and then are bonded together. In the substrate and in the diamond table, there are metal-to-metal bonds created by the high pressure and high temperature sintering process. And in the gradient transition zone, diamond-to-metal bonds are created between diamond and solvent-catalyst metal.

The combination of these various chemical bonds and the mechanical grip exerted by solvent-catalyst metal in the diamond table such as in the interstitial spaces of the diamond structure diamond table provide extraordinarily high bond strength between the diamond table and the substrate. Interstitial spaces are present in the diamond structure and those spaces typically are filled with solvent-catalyst metal, forming veins of solvent-catalyst metal within the polycrystalline diamond structure. This bonding structure contributes to the extraordinary fracture toughness of the compact, and the veins of metal within the diamond table act as energy sinks halting propagation of incipient cracks within the diamond structure. The transition zone and metal vein structure provide the compact with a gradient of material properties between those of the diamond table and those of substrate material, further contributing to the extreme toughness of the compact. The transition zone can also be called an interface, a gradient transition zone, a composition gradient zone, or a composition gradient, depending on its characteristics. The transition zone distributes diamond/substrate stress over the thickness of the zone, reducing zone high stress of a distinct linear interface. The subject residual stress is created as pressure and temperature are reduced at the conclusion of the high pressure/high temperature sintering process due to the difference in pressure and thermal expansive properties of the diamond and substrate materials.

The diamond sintering process occurs under conditions of extremely high pressure and high temperature. According to the inventors' best experimental and theoretical understanding, the diamond sintering process progresses through the following sequence of events: At pressure, a cell containing feedstock of unbonded diamond powder or crystals (diamond feedstock) and a substrate is heated to a temperature above the melting point of the substrate metal 110 and molten metal flows or sweeps into the interstitial voids 107 between the adjacent diamond crystals 106. It is carried by the pressure gradient to fill the voids as well as being pulled in by the surface energy or capillary action of the large surface area of the diamond crystals 106. As the temperature continues to rise, carbon atoms from the surface of diamond crystals dissolve into this interstitial molten metal, forming a carbon solution.

At the proper threshold of temperature and pressure, diamond becomes the thermodynamically favored crystalline allotrope of carbon. As the solution becomes super saturated with respect to $C_d$ (carbon diamond), carbon from this solution begins to crystallize as diamond onto the surfaces of diamond crystals bonding adjacent diamond crystals together with diamond-diamond bonds into a sintered polycrystalline diamond structure 106. The interstitial metal fills the remaining void space forming the vein-like lattice structure 107 within the diamond table by capillary forces and pressure driving forces. Because of the crucial role that the interstitial metal plays in forming a solution of carbon atoms and stabilizing these reactive atoms during the diamond crystallization phase in which the polycrystalline diamond structure 106 is formed, the metal is referred to as a solvent-catalyst metal.

FIG. 1BB depicts a polycrystalline diamond compact having both substrate metal 180 and diamond 181, but in which there is a continuous gradient transition 182 from substrate metal to diamond. In such a compact, the gradient transition zone may be the entire compact, or a portion of the compact. The substrate side of the compact may contain nearly pure metal for easy machining and attachment to other components, while the diamond side may be extremely hard, smooth and durable for use in a hostile work environment.

In some embodiments, a quantity of solvent-catalyst metal may be combined with the diamond feedstock prior to sintering. This is found to be necessary when forming thick PCD tables, solid PDC structures, or when using multimodal fine diamond where there is little residual free space within the diamond powder. In each of these cases, there may not be sufficient ingress of solvent-catalyst metal via the sweep mechanism to adequately mediate the sintering process as a solvent-catalyst. The metal may be added by direct addition of powder, or by generation of metal powder in situ with an attritor mill or by the well-known method of chemical reduction of metal salts deposited on diamond crystals. Added metal may constitute any amount from less than 1% by mass, to greater than 35%. This added metal may consist of the same metal or alloy as is found in the substrate, or may be a different metal or alloy selected because of its material and mechanical properties. Example ratios of diamond feedstock to solvent-catalyst metal prior to sintering include mass ratios of 70:30, 85:15, 90:10, and 95:15. The metal in the diamond feedstock may be added powder metal, metal added by an attritor method, vapor deposition or chemical reduction of metal into powder.

When sintering diamond on a substrate with an interface boundary layer, it may be that no solvent-catalyst metal from the substrate is available to sweep into the diamond table and participate in the sintering process. In this case, the boundary layer material, if composed of a suitable material, metal or alloy that can function as a solvent-catalyst, may serve as the sweep material mediating the diamond sintering process. In other cases where the desired boundary material cannot serve as a solvent-catalyst, a suitable amount of solvent-catalyst metal powder as described herein is added to the diamond crystal feed stock as described above. This assembly is then taken through the sintering process. In the absence of a substrate metal source, the solvent-catalyst metal for the diamond sintering process must be supplied entirely from the added metal powder. The boundary material may bond chemically to the substrate material, and may bond chemically to the diamond table and/or the added solvent-catalyst metal in the diamond table. The remainder of the sintering and fabrication process may be the same as with the conventional solvent-catalyst sweep sintering and fabrication process.

For the sake of simplicity and clarity in this patent, the substrate, transition zone, and diamond table have been discussed as distinct layers. However, it is important to realize that the finished sintered object may be a composite structure characterized by a continuous gradient transition from substrate material to diamond table rather than as distinct layers with clear and discrete boundaries, hence the term "compact."

In addition to the sintering processes described above, diamond parts suitable for use as modular bearing inserts and joint components may also be fabricated as solid or free-standing polycrystalline diamond structures without a substrate. These may be formed by placing the diamond powder combined with a suitable amount of added solvent-catalyst metal powder as described above in a refractory metal can (typically Ta, Nb, Zr, or Mo) with a shape approximating the shape of the final part desired. This assembly is then taken through the sintering process. However, in the absence of a substrate metal source, the solvent-catalyst metal for the diamond sintering process must be supplied entirely from the added metal powder. With suitable finishing, objects thus formed may be used as is, or bonded to metal or other substrates.

Sintering is a method of creating a diamond table with a strong and durable constitution. Other methods of producing a diamond table that may or may not be bonded to a substrate are possible. At present, these typically are not as strong or durable as those fabricated with the sintering process. It is also possible to use these methods to form diamond structures directly onto substrates suitable for use as modular bearing inserts and joints. A table of polycrystalline diamond either with or without a substrate may be manufactured and later attached to a modular bearing inserts and joints in a location such that it will form a surface. The attachment could be performed with any suitable method, including welding, brazing, sintering, diffusion welding, diffusion bonding, inertial welding, adhesive bonding, or the use of fasteners such as screws, bolts, or rivets. In the case of attaching a diamond table without a substrate to another object, the use of such methods as brazing, diffusion welding/bonding or inertia welding may be most appropriate.

Although high pressure/high temperature sintering is a method for creating a diamond surface, other methods for producing a volume of diamond may be employed as well. For example, either chemical vapor deposition (CVD), or physical vapor deposition (PVD) processes may be used. CVD produces a diamond layer by thermally cracking an organic molecule and depositing carbon radicals on a substrate. PVD produces a diamond layer by electrically causing carbon radicals to be ejected from a source material and to deposit on a substrate where they build a diamond crystal structure.

The CVD and PVD processes have some advantages over sintering. Sintering is performed in large, expensive presses at high pressure (such as 45-68 kilobars) and at high temperatures (such as 1200 to 1500 degrees Celsius). It is difficult to achieve and maintain desired component shape using a sintering process because of flow of high pressure mediums used and possible deformation of substrate materials.

In contrast, CVD and PVD take place at atmospheric pressure or lower, so there no need for a pressure medium and there is no deformation of substrates.

Another disadvantage of sintering is that it is difficult to achieve some geometries in a sintered PDC. When CVD or PVD are used, however, the gas phase used for carbon radical deposition can completely conform to the shape of the object being coated, making it easy to achieve a desired non-planar shape.

Another potential disadvantage of sintering PDCs is that the finished component will tend to have large residual stresses caused by differences in the coefficient of thermal expansion and modulus between the diamond and the substrate. While residual stresses can be used to improve strength of a part, they can also be disadvantageous. When CVD or PVD is used, residual stresses can be minimized because CVD and PVD processes do not involve a significant pressure transition (such from 68 Kbar to atmospheric pressure in high pressure and high temperature sintering) during manufacturing.

Another potential disadvantage of sintering PDCs is that few substrates have been found that are suitable for sintering. Tungsten carbide is a common choice for substrate materials. Non-planar components have been made using other substrates. When CVD or PVD are used, however, synthetic diamond can be placed on many substrates, including titanium, most carbides, silicon, molybdenum and others. This is because the temperature and pressure of the CVD and PVD coating processes are low enough that differences in coefficient of thermal expansion and modulus between diamond and the substrate are not as critical as they are in a high temperature and high pressure sintering process.

A further difficulty in manufacturing sintered PDCs is that as the size of the part to be manufactured increases, the size of the press must increase as well. Sintering of diamond will only take place at certain pressures and temperatures, such as those described herein. In order to manufacture larger sintered polycrystalline diamond compacts, ram pressure of the press (tonnage) and size of tooling (such as dies and anvils) must be increased in order to achieve the necessary pressure for sintering to take place. But increasing the size and capacity of a press is more difficult than simply increasing the dimensions of its components. There may be practical physical size constraints on press size due to the manufacturing process used to produce press tooling.

Tooling for a press is typically made from cemented tungsten carbide. In order to make tooling, the cemented tungsten carbide is sintered in a vacuum furnace followed by pressing in a hot isosatic press ("HIP") apparatus. Hipping should be performed in a manner that maintains uniform temperature throughout the tungsten carbide in order to achieve uniform physical qualities and quality. These requirements impose a practical limit on the size tooling that can be produced for a press that is useful for sintering PDCs. The limit on the size tooling that can be produced also limits the size press that can be produced.

CVD and PVD manufacturing apparatuses may be scaled up in size with few limitations, allowing them to produce polycrystalline diamond compacts of almost any desired size.

CVD and PVD processes are also advantageous because they permit precise control of the thickness and uniformity of the diamond coating to be applied to a substrate. Temperature is adjusted within the range of 500 to 1000 degrees Celsius, and pressure is adjusted in a range of less than 1 atmosphere to achieve desired diamond coating thickness.

Another advantage of CVD and PVD processes is that they allow the manufacturing process to be monitored as it progresses. A CVD or PVD reactor can be opened before manufacture of a part is completed so that the thickness and quality of the diamond coating being applied to the part may be determined. From the thickness of the diamond coating that has already been applied, time to completion of manufacture can be calculated. Alternatively, if the coating is not of desired quality, the manufacturing processes may be aborted in order to save time and money.

In contrast, sintering of PDCs is performed as a batch process that cannot be interrupted, and progress of sintering cannot be monitored. The pressing process must be run to completion and the part may only be examined afterward.

Figure 2:
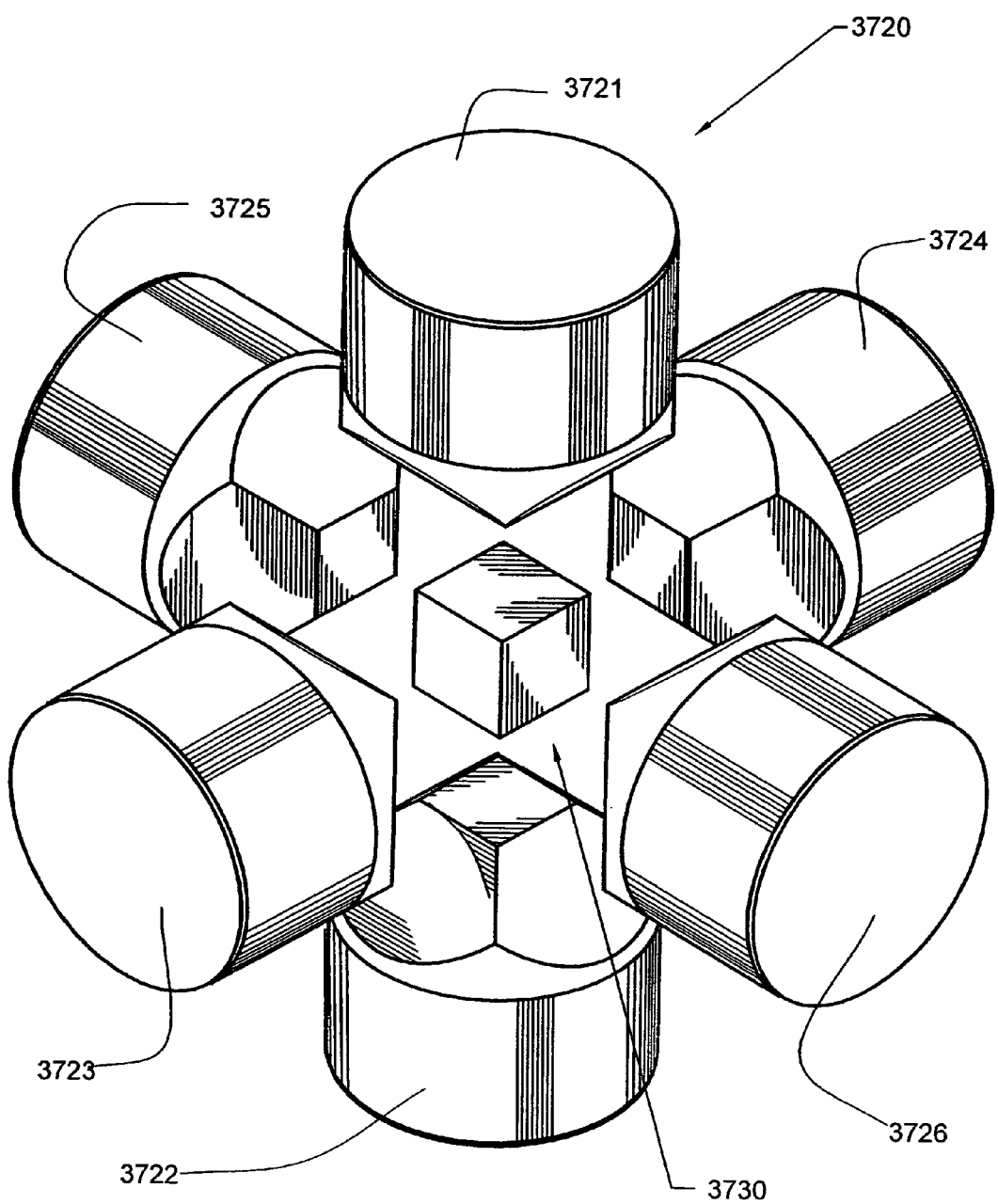
FIG. 2 depicts the anvils of a cubic press that can be used to provide a high temperature and high pressure sintering environment, or for hipping.

A cubic press (i.e., the press has six anvil faces) may be used for transmitting high pressure to an assembly to under sintering or hipping. For example, a cubic press applies pressure along 3 axes from six different directions. Alternatively, a belt press and a cylindrical cell can be used to obtain similar results. Other presses that may be used include a piston-cylinder press and a tetrahedral press. Referring to FIG. 2, a representation of the 6 anvils of a cubic press 3720 is provided. The anvils 3721, 3722, 3723, 3724, 3725 and 3726 are situated around a pressure assembly 3730 to carry out sintering or hipping by use of high temperature and high pressure. The exact sintering or hipping conditions depend on the materials used, size of the component being manufactured, and the material and strength properties desired in the finished product.

A cubic press usually relies on six carbide anvils attached to massive hydraulic cylinders converging simultaneously on a cube-shaped high-pressure capsule. This tri-axial system generates an essentially iso-static high-pressure condition, which is particularly suited to sintering products with complex 3-dimensional geometries. Such a press system will be integrated with computerized control systems to assure optimal and consistent pressure, time, and temperature sintering conditions.

A belt press uses two carbide punches converging upon a high-pressure capsule contained within a carbide die to generate the extreme pressure required to sinter polycrystalline products. Shrink-fitted steel belts pre-stress the inner carbide die, allowing it to withstand the immense internal pressure that occurs during sintering.

A piston-cylinder press is similar to a belt press, with a high-pressure capsule is contained within the cylindrical bore of a carbide die. Two free-floating carbide pistons engage within the bore, pressurizing the capsule when load is applied by conical carbide anvils. The carbide die is supported by radial hydraulic pressure rather than a series of steel belts. This allows simultaneous pressurization of both the inside and outside of the die. Since this press is essentially a gasketless system, there is very little material movement within the pressure volume during pressurization and heating.

CVD and PVD Diamond

CVD is performed in an apparatus called a reactor. A basic CVD reactor includes four components. The first component of the reactor is one or more gas inlets. Gas inlets may be chosen based on whether gases are premixed before introduction to the chamber or whether the gases are allowed to mix for the first time in the chamber. The second component of the reactor is one or more power sources for the generation of thermal energy. A power source is needed to heat the gases in the chamber. A second power source may be used to heat the substrate material uniformly in order to achieve a uniform coating of diamond on the substrate. The third component of the reactor is a stage or platform on which a substrate is placed. The substrate will be coated with diamond during the CVD process. Stages used include a fixed stage, a translating stage, a rotating stage and a vibratory stage. An appropriate stage must be chosen to achieve desired diamond coating quality and uniformity. The fourth component of the reactor is an exit port for removing exhaust gas from the chamber. After gas has reacted with the substrate, it must be removed from the chamber as quickly as possible so that it does not participate in other reactions, which would be deleterious to the diamond coating.

CVD reactors are classified according to the power source used. The power source is chosen to create the desired species necessary to carry out diamond thin film deposition. Some CVD reactor types include plasma-assisted microwave, hot filament, electron beam, single, double or multiple laser beam, arc jet and DC discharge. These reactors differ in the way they impart thermal energy to the gas species and in their efficiency in breaking gases down to the species necessary for deposition of diamond. It is possible to have an array of lasers to perform local heating inside a high pressure cell. Alternatively, an array of optical fibers could be used to deliver light into the cell.

The basic process by which CVD reactors work is as follows. A substrate is placed into the reactor chamber. Reactants are introduced to the chamber via one or more gas inlets. For diamond CVD, methane ($CH_4$) and hydrogen ($H_2$) gases may be brought into the chamber in premixed form. Instead of methane, any carbon-bearing gas in which the carbon has sp3 bonding may be used. Other gases may be added to the gas stream in order to control quality of the diamond film, deposition temperature, gain structure and growth rate. These include oxygen, carbon dioxide, argon, halogens and others.

The gas pressure in the chamber is maintained at about 100 torr. Flow rates for the gases through the chamber are about 10 standard cubic centimeters per minute for methane and about 100 standard cubic centimeters per minute for hydrogen. The composition of the gas phase in the chamber is in the range of 90-99.5% hydrogen and 0.5-10% methane.

When the gases are introduced into the chamber, they are heated. Heating may be accomplished by many methods. In a plasma-assisted process, the gases are heated by passing them through a plasma. Otherwise, the gases may be passed over a series of wires such as those found in a hot filament reactor.

Heating the methane and hydrogen will break them down into various free radicals. Through a complicated mixture of reactions, carbon is deposited on the substrate and joins with other carbon to form crystalline diamond by sp3 bonding. The atomic hydrogen in the chamber reacts with and removes hydrogen atoms from methyl radicals attached to the substrate surface in order to create molecular hydrogen, leaving a clear solid surface for further deposition of free radicals.

If the substrate surface promotes the formation of sp2 carbon bonds, or if the gas composition, flow rates, substrate temperature or other variables are incorrect, then graphite rather than diamond will grow on the substrate.

There are many similarities between CVD reactors and processes and PVD reactors and processes. PVD reactors differ from CVD reactors in the way that they generate the deposition species and in the physical characteristics of the deposition species. In a PVD reactor, a plate of source material is used as a thermal source, rather than having a separate thermal source as in CVD reactors. A PVD reactor generates electrical bias across a plate of source material in order to generate and eject carbon radicals from the source material. The reactor bombards the source material with high energy ions. When the high energy ions collide with source material, they cause ejection of the desired carbon radicals from the source material. The carbon radicals are ejected radially from the source material into the chamber. The carbon radicals then deposit themselves onto whatever is in their path, including the stage, the reactor itself, and the substrate.

Figure 1C:
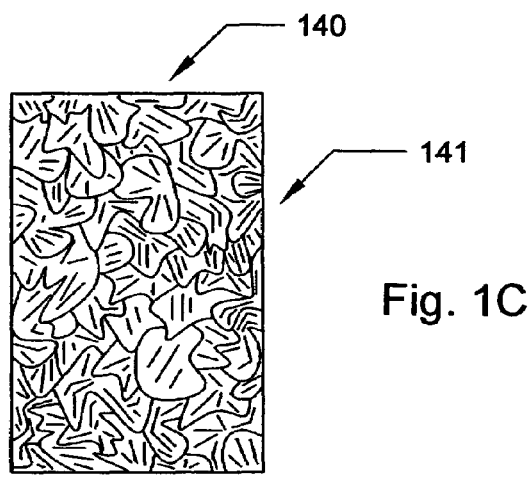
FIG. 1C depicts a substrate prior to use of a CVD or PVD process to form a volume of diamond on the substrate.
Figure 1D:
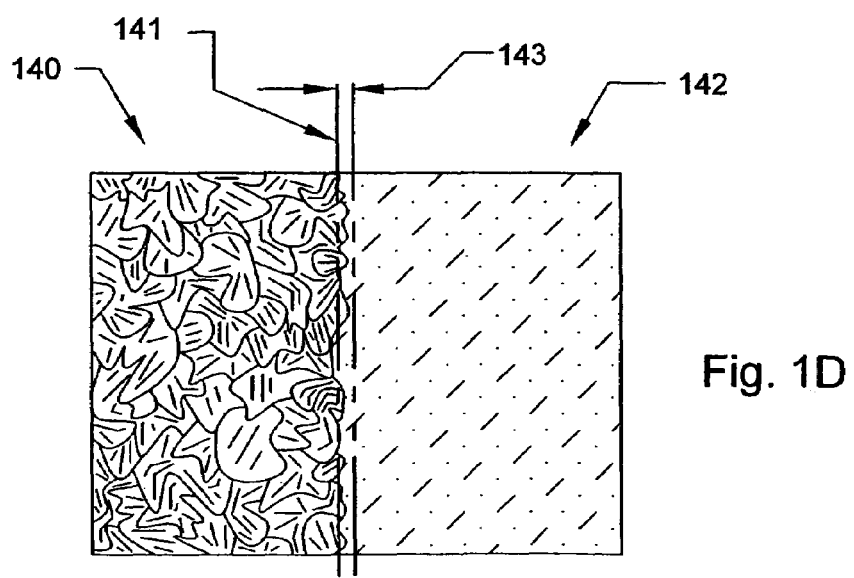
FIG. 1D depicts a diamond compact formed by a CVD or PVD process.

Referring to FIG. 1C, a substrate 140 of appropriate material is depicted having a deposition face 141 on which diamond may be deposited by a CVD or PVD process. FIG. 1D depicts the substrate 140 and the deposition face 141 on which a volume of diamond 142 has been deposited by CVD or PVD processes. A small transition zone 143 is present in which both diamond and substrate are located. In comparison to FIG. 1B, it can be seen that the CVD or PVD diamond deposited on a substrate lacks the more extensive gradient transition zone of sintered polycrystalline diamond compacts because there is no sweep of solvent-catalyst metal through the diamond table in a CVD or PVD process.

Both CVD and PVD processes achieve diamond deposition by line of sight. Means (such as vibration and rotation) are provided for exposing all desired surfaces for diamond deposition. If a vibratory stage is to be used, the surface will vibrate up and down with the stage and thereby present all surfaces to the free radical source.

There are several methods, which may be implemented in order to coat cylindrical objects with diamond using CVD or PVD processes. If a plasma assisted microwave process is to be used to achieve diamond deposition, then the object to receive the diamond must be directly under the plasma in order to achieve the highest quality and most uniform coating of diamond. A rotating or translational stage may be used to present every aspect of the surface to the plasma for diamond coating. As the stage rotates or translates, all portions of the surface may be brought directly under the plasma for coating in such a way to achieve sufficiently uniform coating.

If a hot filament CVD process is used, then the surface should be placed on a stationary stage. Wires or filaments (typically tungsten) are strung over the stage so that their coverage includes the surface to be coated. The distance between the filaments and the surface and the distance between the filaments themselves may be chosen to achieve a uniform coating of diamond directly under the filaments.

Diamond surfaces can be manufactured by CVD and PVD process either by coating a substrate with diamond or by creating a free-standing volume of diamond, which is later mounted for use. A free-standing volume of diamond may be created by CVD and PVD processes in a two-step operation. First, a thick film of diamond is deposited on a suitable substrate, such as silicon, molybdenum, tungsten or others. Second, the diamond film is released from the substrate.

As desired, segments of diamond film may be cut away, such as by use of a Q-switched YAG laser. Although diamond is transparent to a YAG laser, there is usually a sufficient amount of sp2 bonded carbon (as found in graphite) to allow cutting to take place. If not, then a line may be drawn on the diamond film using a carbon-based ink. The line should be sufficient to permit cutting to start, and once started, cutting will proceed slowly.

After an appropriately-sized piece of diamond has been cut from a diamond film, it can be attached to a desired object in order to serve as a surface. For example, the diamond may be attached to a substrate by welding, diffusion bonding, adhesion bonding, mechanical fixation or high pressure and high temperature bonding in a press.

Although CVD and PVD diamond on a substrate do not exhibit a gradient transition zone that is found in sintered polycrystalline diamond compacts, CVD and PVD process can be conducted in order to incorporate metal into the diamond table. As mentioned elsewhere herein, incorporation of metal into the diamond table enhances adhesion of the diamond table to its substrate and can strengthen the polycrystalline diamond compact. Incorporation of diamond into the diamond table can be used to achieve a diamond table with a coefficient of thermal expansion and compressibility different from that of pure diamond, and consequently increasing fracture toughness of the diamond table as compared to pure diamond. Diamond has a low coefficient of thermal expansion and a low compressibility compared to metals. Therefore the presence of metal with diamond in the diamond table achieves a higher and more metal-like coefficient of thermal expansion and the average compressibility for the diamond table than for pure diamond. Consequently, residual stresses at the interface of the diamond table and the substrate are reduced, and delamination of the diamond table from the substrate is less likely.

A pure diamond crystal also has low fracture toughness. Therefore, in pure diamond, when a small crack is formed, the entire diamond component fails catastrophically. In comparison, metals have a high fracture toughness and can accommodate large cracks without catastrophic failure. Incorporation of metal into the diamond table achieves a greater fracture toughness than pure diamond. In a diamond table having interstitial spaces and metal within those interstitial spaces, if a crack forms in the diamond and propagates to an interstitial space containing metal, the crack will terminate at the metal and catastrophic failure will be avoided. Because of this characteristic, a diamond table with metal in its interstitial spaces is able to sustain much higher forces and workloads without catastrophic failure compared to pure diamond.

Diamond-diamond bonding tends to decrease as metal content in the diamond table increases. CVD and PVD processes can be conducted so that a transition zone is established. However, the surface may be essentially pure PCD for low wear properties.

Generally CVD and PVD diamond is formed without large interstitial spaces filled with metal. Consequently, most PVD and CVD diamond is more brittle or has a lower fracture toughness than sintered PDCs. CVD and PVD diamond may also exhibit the maximum residual stresses possible between the diamond table and the substrate. It is possible, however, to form CVD and PVD diamond film that has metal incorporated into it with either a uniform or a functionally gradient composition.

One method for incorporating metal into a CVD or PVD diamond film is to use two different source materials in order to simultaneously deposit the two materials on a substrate in a CVD of PVD diamond production process. This method may be used regardless of whether diamond is being produced by CVD, PVD or a combination of the two.

Another method for incorporating metal into a CVD diamond film chemical vapor infiltration. This process would first create a porous layer of material, and then fill the pores by chemical vapor infiltration. The porous layer thickness should be approximately equal to the desired thickness for either the uniform or gradient layer. The size and distribution of the pores can be used to control ultimate composition of the layer. Deposition in vapor infiltration occurs first at the interface between the porous layer and the substrate. As deposition continues, the interface along which the material is deposited moves outward from the substrate to fill pores in the porous layer. As the growth interface moves outward, the deposition temperature along the interface is maintained by moving the sample relative to a heater or by moving the heater relative to the growth interface. It is imperative that the porous region between the outside of the sample and the growth interface be maintained at a temperature that does not promote deposition of material (either the pore-filling material or undesired reaction products). Deposition in this region would close the pores prematurely and prevent infiltration and deposition of the desired material in inner pores. The result would be a substrate with open porosity and poor physical properties.

Laser Deposition of Diamond

Another alternative manufacturing process that may be used to produce surfaces and components involves use of energy beams, such as laser energy, to vaporize constituents in a substrate and redeposit those constituents on the substrate in a new form, such as in the form of a diamond coating. As an example, a metal, polymeric or other substrate may be obtained or produced containing carbon, carbides or other desired constituent elements. Appropriate energy, such as laser energy, may be directed at the substrate to cause constituent elements to move from within the substrate to the surface of the substrate adjacent the area of application of energy to the substrate. Continued application of energy to the concentrated constituent elements on the surface of the substrate can be used to cause vaporization of some of those constituent elements. The vaporized constituents may then be reacted with another element to change the properties and structure of the vaporized constituent elements.

Next, the vaporized and reacted constituent elements (which may be diamond) may be diffused into the surface of the substrate. A separate fabricated coating may be produced on the surface of the substrate having the same or a different chemical composition than that of the vaporized and reacted constituent elements. Alternatively, some of the changed constituent elements that were diffused into the substrate may be vaporized and reacted again and deposited as a coating on the substrate. By this process and variations of it, appropriate coatings such as diamond, cubic boron nitride, diamond like carbon, $B_4C$, SiC, TiC, TiN, TiB, cCN, $Cr_3C_2$, and $Si_3N_4$ may be formed on a substrate.

In other manufacturing environments, high temperature laser application, electroplating, sputtering, energetic laser excited plasma deposition or other methods may be used to place a volume of diamond, diamond-like material, a hard material or a superhard material in a location that will serve as a surface.

In light of the disclosure herein, those of ordinary skill in the art will comprehend the apparatuses, materials and process conditions necessary for the formation and use of high quality diamond on a substrate using any of the manufacturing methods described herein in order to create a diamond surface.

Material Property Considerations

In areas outside of modular bearing inserts and joints, in particular in the field of rock drilling cutters, polycrystalline diamond compacts have been used for some time. Historically those cutters have been cylindrical in shape with a planar diamond table at one end. The diamond surface of a cutter is much smaller than the surface needed in most modular bearing inserts and joints s. Thus, polycrystalline diamond cutter geometry and manufacturing methods are not directly applicable to modular bearing inserts and joints.

There is a particular problem posed by the manufacture of a non-planar diamond surface. The non-planar component design requires that pressures be applied radially in making the part. During the high pressure sintering process, described in detail below, all displacements must be along a radian emanating from the center of the sphere that will be produced to achieve the non-planar geometry. To achieve this in high temperature/high pressure pressing, an isostatic pressure field must be created. During the manufacture of such non-planar parts, if there is any deviatoric stress component, it will result in distortion of the part and may render the manufactured part useless.

Special considerations that must be taken into account in making non-planar polycrystalline diamond compacts are discussed below.

Modulus

Most polycrystalline diamond compacts include both a diamond table and a substrate. The material properties of the diamond and the substrate may be compatible, but the high pressure and high temperature sintering process in the formation of a polycrystalline diamond compact may result in a component with excessively high residual stresses. For example, for a polycrystalline diamond compact using tungsten carbide as the substrate, the sintered diamond has a Young's modulus of approximately 120 million p.s.i., and cobalt cemented tungsten carbide has a modulus of approximately 90 million p.s.i. Modulus refers to the slope of the curve of the stress plotted against the stress for a material. Modulus indicates the stiffness of the material. Bulk modulus refers to the ratio of isostatic strain to isostatic stress, or the unit volume reduction of a material versus the applied pressure or stress.

Because diamond and most substrate materials have such a high modulus, a very small stress or displacement of the polycrystalline diamond compact can induce very large stresses. If the stresses exceed the yield strength of either the diamond or the substrate, the component will fail. The strongest polycrystalline diamond compact is not necessarily stress free. In a polycrystalline diamond compact with optimal distribution of residual stress, more energy is required to induce a fracture than in a stress free component. Thus, the difference in modulus between the substrate and the diamond must be noted and used to design a component that will have the best strength for its application with sufficient abrasion resistance and fracture toughness.

Coefficient of Thermal Expansion ("CTE")

The extent to which diamond and its substrate differ in how they deform relative to changes in temperature also affects their mechanical compatibility. Coefficient of thermal expansion ("CTE") is a measure of the unit change of a dimension with unit change in temperature or the propensity of a material to expand under heat or to contract when cooled. As a material experiences a phase change, calculations based on CTE in the initial phase will not be applicable. It is notable that when compacts of materials with different CTEs and moduluses are used, they will stress differently at the same stress.

PCD has a CTE on the order of 24 micro inches per inch ($10^{-6}$ inches) of material per degree ($\mu in/in\ ^\circ C.$). In contrast, carbide has a CTE on the order of 6-8 $\mu in/in\ ^\circ C$. Although these values appear to be close numerically, the influence of the high modulus creates very high residual stress fields when a temperature gradient of a few hundred degrees is imposed upon the combination of substrate and diamond. The difference in coefficient of thermal expansion is less of a problem in simple planar PDCs than in the manufacture of non-planar or complex shapes. When a non-planar PDC is manufactured, differences in the CTE between the diamond and the substrate can cause high residual stress with subsequent cracking and failure of the diamond table, the substrate or both at any time during or after high pressure/high temperature sintering.

Dilatoric and Deviatoric Stresses

The diamond and substrate assembly will experience a reduction of free volume during the sintering process. The sintering process, described in detail below, involves subjecting the substrate and diamond assembly to pressure ordinarily in the range of about 40 to about 68 kilobar. The pressure will cause volume reduction of the substrate. Some geometrical distortion of the diamond and/or the substrate may also occur. The stress that causes geometrical distortion is called deviatoric stress, and the stress that causes a change in volume is called dilatoric stress. In an isostatic system, the deviatoric stresses sum to zero and only the dilatoric stress component remains. Failure to consider all of these stress factors in designing and sintering a polycrystalline diamond component with complex geometry (such as concave and convex non-planar polycrystalline diamond compacts) will likely result in failure of the process.

Free Volume Reduction of Diamond Feedstock

As a consequence of the physical nature of the feedstock diamond, large amounts of free volume are present unless special preparation of the feedstock is undertaken prior to sintering. It is necessary to eliminate as much of the free volume in the diamond as possible, and if the free volume present in the diamond feedstock is too great, then sintering may not occur. It is also possible to eliminate the free volume during sintering if a press with sufficient ram displacement is employed. It is important to maintain a desired uniform geometry of the diamond and substrate during any process that reduces free volume in the feedstock, or a distorted or faulty component may result.

Selection of Solvent-Catalyst Metal

Formation of synthetic diamond in a high temperature and high pressure press without the use of a solvent-catalyst metal is not a viable method at this time, although it may become viable in the future. A solvent-catalyst metal is required to achieve desired crystal formation in synthetic diamond. The solvent-catalyst metal first solvates carbon preferentially from the sharp contact points of the diamond feedstock crystals. It then recrystallizes the carbon as diamond in the interstices of the diamond matrix with diamond-diamond bonding sufficient to achieve a solid with 95 to 97% of theoretical density with solvent metal 5-3% by volume. That solid distributed over the substrate surface is referred to herein as a polycrystalline diamond table. The solvent-catalyst metal also enhances the formation of chemical bonds with substrate atoms.

A method for adding the solvent-catalyst metal to diamond feedstock is by causing it to sweep from the substrate that contains solvent-catalyst metal during high pressure and high temperature sintering. Powdered solvent-catalyst metal may also be added to the diamond feedstock before sintering, particularly if thicker diamond tables are desired. An attritor method may also be used to add the solvent-catalyst metal to diamond feedstock before sintering. If too much or too little solvent-catalyst metal is used, then the resulting part may lack the desired mechanical properties, so it is important to select an amount of solvent-catalyst metal and a method for adding it to diamond feedstock that is appropriate for the particular part to be manufactured.

Diamond Feedstock Particle Size and Distribution

The durability of the finished diamond product is integrally linked to the size of the feedstock diamond and also to the particle distribution. Selection of the proper size(s) of diamond feedstock and particle distribution depends upon the service requirement of the specimen and also its working environment. The durability of polycrystalline diamond is enhanced if smaller diamond feedstock crystals are used and a highly diamond-diamond bonded diamond table is achieved.

Although polycrystalline diamond may be made from single modal diamond feedstock, use of multi-modal feedstock increases both impact strength and wear resistance. The use of a combination of large crystal sizes and small crystal sizes of diamond feedstock together provides a part with high impact strength and wear resistance, in part because the interstitial spaces between the large diamond crystals may be filled with small diamond crystals. During sintering, the small crystals will solvate and reprecipitate in a manner that binds all of the diamond crystals into a strong and tightly bonded compact.

Diamond Feedstock Loading Methodology

Contamination of the diamond feedstock before or during loading will cause failure of the sintering process. Great care must be taken to ensure the cleanliness of diamond feedstock and any added solvent-catalyst metal or binder before sintering.

In order to prepare for sintering, clean diamond feedstock, substrate, and container components are prepared for loading. The diamond feedstock and the substrate are placed into a refractory metal container called a "can" which will seal its contents from outside contamination. The diamond feedstock and the substrate will remain in the can while undergoing high pressure and high temperature sintering in order to form a polycrystalline diamond compact. The can may be sealed by electron beam welding at high temperature and in a vacuum.

Enough diamond aggregate (powder or grit) is loaded to account for linear shrinkage during high pressure and high temperature sintering. The method used for loading diamond feedstock into a can for sintering affects the general shape and tolerances of the final part. In particular, the packing density of the feedstock diamond throughout the can should be as uniform as possible in order to produce a good quality sintered polycrystalline diamond compact structure. In loading, bridging of diamond can be avoided by staged addition and packing.

The degree of uniformity in the density of the feedstock material after loading will affect geometry of the PDC. Loading of the feedstock diamond in a dry form versus loading diamond combined with a binder and the subsequent process applied for the removal of the binder will also affect the characteristics of the finished PDC. In order to properly pre-compact diamond for sintering, the pre-compaction pressures should be applied under isostatic conditions.

Selection of Substrate Material

The unique material properties of diamond and its relative differences in modulus and CTE compared to most potential substrate materials diamond make selection of an appropriate polycrystalline diamond substrate a formidable task. A great disparity in material properties between the diamond and the substrate creates challenges for successful manufacture of a PDC with the requisite strength and durability. Even very hard substrates appear to be soft compared to PCD. The substrate and the diamond must be able to withstand not only the pressure and temperature of sintering, but must be able to return to room temperature and atmospheric pressure without delaminating, cracking or otherwise failing.

Selection of substrate material also requires consideration of the intended application for the part, impact resistance and strengths required, and the amount of solvent-catalyst metal that will be incorporated into the diamond table during sintering. Substrate materials must be selected with material properties that are compatible with those of the diamond table to be formed.

Substrate Geometry

Further, it is important to consider whether to use a substrate that has a smooth surface or a surface with topographical features. Substrate surfaces may be formed with a variety of topographical features so that the diamond table is fixed to the substrate with both a chemical bond and a mechanical grip. Use of topographical features on the substrate provides a greater surface area for chemical bonds and with the mechanical grip provided by the topographical features, can result in a stronger and more durable component.

Example Materials and Manufacturing Steps

The inventors have discovered and determined materials and manufacturing processes for constructing PDCs for use in a modular bearing inserts and joints. It is also possible to manufacture the invented surfaces by methods and using materials other than those listed below.

The steps described below, such as selection of substrate material and geometry, selection of diamond feedstock, loading and sintering methods, will affect each other, so although they are listed as separate steps that must be taken to manufacture a PDC or a compact of polycrystalline cubic boron nitride, no step is completely independent of the others, and all steps must be standardized to ensure success of the manufacturing process.

Select Substrate Material and/or Solvent-Catalyst Metal

In order to manufacture any polycrystalline component, an appropriate substrate should be selected (unless the component is to be free standing without a substrate).

TABLE 2

SOME SUBSTRATES FOR PROSTHETIC JOINT APPLICATIONS

| SUBSTRATE | ALLOY NAME | REMARKS |
|---|---|---|
| Titanium | Ti6/4 (TiAlVa) ASTM F-1313 (TiNbZr) ASTM F-620 ASTM F-1580 TiMbHf Nitinol (TiNi + other) | A thin tantalum barrier may be placed on the titanium substrate before loading diamond feedstock. |
| Cobalt chrome | ASTM F-799 | Contains cobalt, chromium and molybdenum. Wrought product |
| Cobalt chrome | ASTM F-90 | Contains cobalt, chromium, tungsten and nickel. |
| Cobalt chrome | ASTM F-75 | Contains cobalt, chromium and molybdenum. Cast product. |
| Cobalt chrome | ASTM F-562 | Contains cobalt, chromium, molybdenum and nickel. |
| Cobalt chrome | ASTM F-563 | Contains cobalt, chromium, molybdenum, tungsten, iron and nickel. |
| Tantalum | ASTM F-560 (unalloyed) | Refractory metal. |
| Platinum | various | |
| Niobium | ASTM F-67 (unalloyed) | Refractory metal. |
| Maganese | Various | May include Cr, Ni, Mg, molybdenum. |
| Cobalt cemented tungsten carbide | WC | Commonly used in synthetic diamond production |
| Cobalt chrome cemented tungsten carbide | CoCr cemented WC | |
| Cobalt chrome cemented chrome carbide | CoCr cemented CrC | |
| Cobalt chrome cemented silicon carbide | CoCr cemented SiC | |
| Fused silicon carbide | SiC | |
| Cobalt chrome molybdenum | CoCrMo | A thin tungsten or tungsten/cobalt layer may be placed on the substrate before loading diamond feedstock. |
| Stainless steel | Various | |

The CoCr used as a substrate or solvent-catalyst metal may be CoCrMo or CoCrW or another suitable CoCr. Alternatively, an Fe-based alloy, a Ni-based alloy (such as Co—Cr—W—Ni) or another alloy may be used. Co and Ni alloys tend to provide a corrosion-resistant component. The preceding substrates and solvent-catalyst metals are examples only. In addition to these substrates, other materials may be appropriate for use as substrates for construction of modular bearing inserts and joints and other surfaces.

When titanium is used as the substrate, it is possible to place a thin tantalum barrier layer on the titanium substrate. The tantalum barrier prevents mixing of the titanium alloys with cobalt alloys used in the diamond feedstock. If the titanium alloys and the cobalt alloys mix, it is possible that a detrimentally low melting point eutectic inter-metallic compound will be formed during the high pressure and high temperature sintering process. The tantalum barrier bonds to both the titanium and cobalt alloys, and to the PCD that contains cobalt solvent-catalyst metals. Thus, a PDC made using a titanium substrate with a tantalum barrier layer and diamond feedstock that has cobalt solvent-catalyst metals can be very strong and well formed. Alternatively, the titanium substrate may be provided with an alpha case oxide coating (an oxidation layer) forming a barrier that prevents formation of a eutectic metal.

If a cobalt chrome molybdenum substrate is used, a thin tungsten layer or a thin tungsten and cobalt layer can be placed on the substrate before loading of the diamond feedstock in order to control formation of chrome carbide (CrC) during sintering.

In addition to those listed, other appropriate substrates may be used for forming PDC surfaces. Further, it is possible within the scope of the claims to form a diamond surface for use without a substrate. It is also possible to form a surface from any of the superhard materials and other materials listed herein, in which case a substrate may not be needed. Additionally, if it is desired to use a type of diamond or carbon other than PCD, substrate selection may differ. For example, if a diamond surface is to be created by use of chemical vapor deposition or physical vapor deposition, then use of a substrate appropriate for those manufacturing environments and for the compositions used will be necessary.

Determination of Substrate Geometry

A substrate geometry appropriate for the compact to be manufactured and appropriate for the materials being used should be selected. In order to manufacture a concave non-planar acetabular cup, a convex non-planar femoral head, or a non-planar surface, it is necessary to select a substrate geometry that will facilitate the manufacture of those parts. In order to ensure proper diamond formation and avoid compact distortion, forces acting on the diamond and the substrate during sintering must be strictly radial. Therefore the substrate geometry at the contact surface with diamond feedstock for manufacturing an acetabular cup, a femoral head, or any other non-planar component is generally non-planar.

As mentioned previously, there is a great disparity in the material characteristics of synthetic diamond and most available substrate materials. In particular, modulus and CTE are of concern. But when applied in combination with each other, some substrates can form a stable and strong PDC. The table below lists physical properties of some substrate materials.

TABLE 3A

MATERIAL PROPERTIES OF SOME SUBSTRATES

| SUBSTRATE MATERIAL | MODULUS | CTE |
| --- | --- | --- |
| Ti 6/4 | 16.5 million psi | 5.4 |
| CoCrMo | 35.5 million psi | 16.9 |
| CoCrW | 35.3 million psi | 16.3 |

Use of either titanium or cobalt chrome substrates alone for the manufacture of non-planar PDCs may result in cracking of the diamond table or separation of the substrate from the diamond table. In particular, it appears that the dominant property of titanium during high pressure and high temperature sintering is compressibility while the dominant property of cobalt chrome during sintering is CTE. In some embodiments, a substrate of two or more layers may be used to achieve dimensional stability during and after manufacturing.

In various embodiments, a single layer substrate may be utilized. In other embodiments, a two-layer substrate may be utilized, as discussed. Depending on the properties of the components being used, however, it may be desired to utilize a substrate that includes three, four or more layers. Such multi-layer substrates are intended to be comprehended within the scope of the claims.

Substrate Surface Topography

Depending on the application, it may be advantageous to include substrate surface topographical features on a substrate that is to be formed into a PDC. Regardless whether a one-piece, a two-piece of a multi-piece substrate is used, it may be desirable to modify the surface of the substrate or provide topographical features on the substrate to increase the total surface area of diamond to enhance substrate to diamond contact and to provide a mechanical grip of the diamond table.

The placement of topographical features on a substrate serves to modify the substrate surface geometry or contours from what the substrate surface geometry or contours would be if formed as a simple planar or non-planar figure. Substrate surface topographical features may include one or more different types of topographical features that result in protruding, indented or contoured features that serve to increase surface, mechanically interlock the diamond table to the substrate, prevent crack formation, or prevent crack propagation.

Substrate surface topographical features or substrate surface modifications serve a variety of useful functions. Use of substrate topographical features increases total substrate surface area of contact between the substrate and the diamond table. This increased surface area of contact between diamond table and substrate results in a greater total number of chemical bonds between diamond table and substrate than if the substrate surface topographical features were absent, thus achieving a stronger PDC.

Substrate surface topographical features also serve to create a mechanical interlock between the substrate and the diamond table. The mechanical interlock is achieved by the nature of the substrate topographical features and also enhances strength of the PDC.

Substrate surface topographical features may also be used to distribute the residual stress field of the PDC over a larger surface area and over a larger volume of diamond and substrate material. This greater distribution can be used to keep stresses below the threshold for crack initiation and/or crack propagation at the diamond table/substrate interface, within the diamond itself and within the substrate itself.

Substrate surface topographical features increase the depth of the gradient interface or transition zone between diamond table and substrate, in order to distribute the residual stress field through a longer segment of the composite compact structure and to achieve a stronger part.

Substrate surface modifications can be used to created a sintered PDC that has residual stresses that fortify the strength of the diamond layer and yield a more robust PDC with greater resistance to breakage than if no surface topographical features were used. This is because in order to break the diamond layer, it is necessary to first overcome the residual stresses in the part and then overcome the strength of the diamond table.

Substrate surface topographical features redistribute forces received by the diamond table. Substrate surface topographical features cause a force transmitted through the diamond layer to be re-transmitted from single force vector along multiple force vectors. This redistribution of forces traveling to the substrate avoids conditions that would deform the substrate material at a more rapid rate than the diamond table, as such differences in deformation can cause cracking and failure of the diamond table.

Substrate surface topographical features may be used to mitigate the intensity of the stress field between the diamond and the substrate in order to achieve a stronger part.

Substrate surface topographical features may be used to distribute the residual stress field throughout the PDC structure in order to reduce the stress per unit volume of structure.

Substrate surface topographical features may be used to mechanically interlock the diamond table to the substrate by causing the substrate to compress over an edge of the diamond table during manufacturing. Dovetailed, non-planar and lentate modifications act to provide force vectors that tend to compress and enhance the interface of diamond table and substrate during cooling as the substrate dilitates radially.

Substrate surface topographical features may also be used to achieve a manufacturable form. As mentioned herein, differences in coefficient of thermal expansion and modulus between diamond and the chosen substrate may result in failure of the PDC during manufacturing. For certain parts, the stronger interface between substrate and diamond table that may be achieved when substrate topographical features are used can achieve a polycrystalline diamond compact that can be successfully manufactured. But if a similar part of the same dimensions is to be made using a substrate with a simple substrate surface rather than specialized substrate surface topographical features, the diamond table may crack or separate from the substrate due to differences in coefficient of thermal expansion or modulus of the diamond and the substrate.

Examples of useful substrate surface topographical features include waves, grooves, ridges, other longitudinal surface features (any of which may be arranged longitudinally, lattitudinally, crossing each other at a desired angle, in random patterns, and in geometric patterns), three dimensional textures, non-planar segment depressions, non-planar segment protrusions, triangular depressions, triangular protrusions, arcuate depressions, arcuate protrusions, partially non-planar depressions, partially non-planar protrusions, cylindrical depressions, cylindrical protrusions, rectangular depressions, rectangular protrusions, depressions of n-sided polygonal shapes where n is an integer, protrusions of n-sided polygonal shapes, a waffle pattern of ridges, a waffle iron pattern of protruding structures, dimples, nipples, protrusions, ribs, fenestrations, grooves, troughs or ridges that have a cross-sectional shape that is rounded, triangular, arcuate, square, polygonal, curved, or otherwise, or other shapes. Machining, pressing, extrusion, punching, injection molding and other manufacturing techniques for creating such forms may be used to achieve desired substrate topography. Illustration of example substrate topographical features is found in U.S. Pat. No. 6,709,463 which is hereby incorporated by reference in its entirety.

Although many substrate topographies have been depicted in convex non-planar substrates, those surface topographies may be applied to convex non-planar substrate surfaces, other non-planar substrate surfaces, and flat substrate surfaces. Substrate surface topographies which are variations or modifications of those shown, and other substrate topographies which increase component strength or durability may also be used.

Diamond Feedstock Selection

It is anticipated that typically the diamond particles used will be in the range of less than 1 micron to more than 100 microns. In some embodiments, however, diamond particles as small as 1 nanometer may be used. Smaller diamond particles are preferred for smoother surfaces. Commonly, diamond particle sizes will be in the range of 0.5 to 2.0 microns or 0.1 to 10 microns.

An example diamond feedstock is shown in the table below.

TABLE 3B

EXAMPLE BIMODAL DIAMOND FEEDSTOCK

| MATERIAL | AMOUNT |
|---|---|
| 4 to 8 micron diamond | about 90% |
| 0.5 to 1.0 micron diamond | about 9% |
| Titanium carbonitride powder | about 1% |

This formulation mixes some smaller and some larger diamond crystals so that during sintering, the small crystals may dissolve and then recrystallize in order to form a lattice structure with the larger diamond crystals. Titanium carbonitride powder may optionally be included in the diamond feedstock to prevent excessive diamond grain growth during sintering in order to produce a finished product that has smaller diamond crystals.

Another diamond feedstock example is provided in the table below.

TABLE 4

EXAMPLE TRIMODAL DIAMOND FEEDSTOCK

| MATERIAL | AMOUNT |
|---|---|
| Size x diamond crystals | about 90% |
| Size 0.1x diamond crystals | about 9% |
| Size 0.01x diamond crystals | about 1% |

The trimodal diamond feedstock described above can be used with any suitable diamond feedstock having a first size or diameter "x", a second size 0.1X and a third size 0.01x. This ratio of diamond crystals allows packing of the feedstock to about 89% theoretical density, closing most interstitial spaces and providing the densest diamond table in the finished polycrystalline diamond compact.

Another diamond feedstock example is provided in the table below.

TABLE 5

EXAMPLE TRIMODAL DIAMOND FEEDSTOCK

| MATERIAL | AMOUNT |
|---|---|
| Size x diamond crystals | about 88-92% |
| Size 0.1x diamond crystals | about 8-12% |
| Size 0.01x diamond crystals | about 0.8-1.2% |

Another diamond feedstock example is provided in the table below.

TABLE 6

EXAMPLE TRIMODAL DIAMOND FEEDSTOCK

| MATERIAL | AMOUNT |
|---|---|
| Size x diamond crystals | about 85-95% |
| Size 0.1x diamond crystals | about 5-15% |
| Size 0.01x diamond crystals | about 0.5-1.5% |

Another diamond feedstock example is provided in the table below.

TABLE 7

EXAMPLE TRIMODAL DIAMOND FEEDSTOCK

| MATERIAL | AMOUNT |
|---|---|
| Size x diamond crystals | about 80-90% |
| Size 0.1x diamond crystals | about 10-20% |
| Size 0.01x diamond crystals | about 0-2% |

In some embodiments, the diamond feedstock used will be diamond powder having a greatest dimension of about 100 nanometers or less. In some embodiments some solvent-catalyst metal is included with the diamond feedstock to aid in the sintering process, although in many applications there will be a significant solvent-catalyst metal sweep from the substrate during sintering as well.

Solvent Metal Selection

It has already been mentioned that solvent metal will sweep from the substrate through the diamond feedstock during sintering to solvate some diamond crystals so that they may later recrystallize and form a diamond-diamond bonded lattice network that characterizes PCD. In the event of making a freestanding compact of PCD without a substrate, solvent metal may be mixed with diamond crystals before sintering to achieve the same result. Even if a substrate is being used, It is possible to include some solvent-catalyst metal in the diamond feedstock when desired to supplement the sweep of solvent-catalyst metal from the substrate.

Traditionally, cobalt, nickel and iron have been used as solvent metals for making PCD. Platinum and other materials could also be used for a binder.

CoCr may be used as a solvent-catalyst metal for sintering PCD to achieve a more wear resistant PDC. Infiltrating diamond particles with Cobalt (Co) metal produces standard PDC. As the cobalt infiltrates the diamond, carbon is dissolved (mainly from the smaller diamond grains) and reprecipitates onto the larger diamond grains causing the grains to grow together. This is known as liquid phase sintering. The remaining pore spaces between the diamond grains are filled with cobalt metal.

In one example, the alloy Cobalt Chrome (CoCr) may be used as the solvent metal which acts similarly to Co metal. However, it differs in that the CoCr reacts with some of the dissolved carbon resulting in the precipitation of CoCr carbides. These carbides, like most carbides, are harder (abrasion resistant) than cobalt metal and results in a more wear or abrasion resistant PDC.

Other metals can be added to Co to form metal carbides as precipitates within the pore spaces between the diamond grains. These metals include the following, but not limited to, Ti, W, Mo, V, Ta, Nb, Zr, Si, and combinations thereof.

It is important not just to add the solvent metal to diamond feedstock, but also to include solvent metal in an appropriate proportion and to mix it evenly with the feedstock. The use of about 86% diamond feedstock and 15% solvent metal by mass (weight) has provided good result, other ratios of diamond feedstock to solvent metal may include 5:95, 10:90, 20:80, 30:70, 40:60, 50:50, 60:40, 65:35, 75:25, 80:20, 90:10, 95:5, 97:3, 98:2, 99:1, 99.5:0.5, 99.7:0.3, 99.8:0.2, 99.9:0.1 and others.

In order to mix the diamond feedstock with solvent-catalyst metal, first the amounts of feedstock and solvent metal to be mixed may be placed together in a mixing bowl, such as a mixing bowl made of the desired solvent-catalyst metal. Then the combination of feedstock and solvent metal may be mixed at an appropriate speed (such as 200 rpm) with dry methanol and attritor balls for an appropriate time period, such as 30 minutes. The attritor balls, the mixing fixture and the mixing bowl may be made from the solvent-catalyst metal. The methanol may then be decanted and the diamond feedstock separated from the attritor balls. The feedstock may then be dried and cleaned by firing in a molecular hydrogen furnace at about 1000 degrees Celsius for about 1 hour. The feedstock is then ready for loading and sintering. Alternatively, it may be stored in conditions that will preserve its cleanliness. Appropriate furnaces that may be used for firing also include hydrogen plasma furnaces and vacuum furnaces.

Loading Diamond Feedstock

Figure 1E:
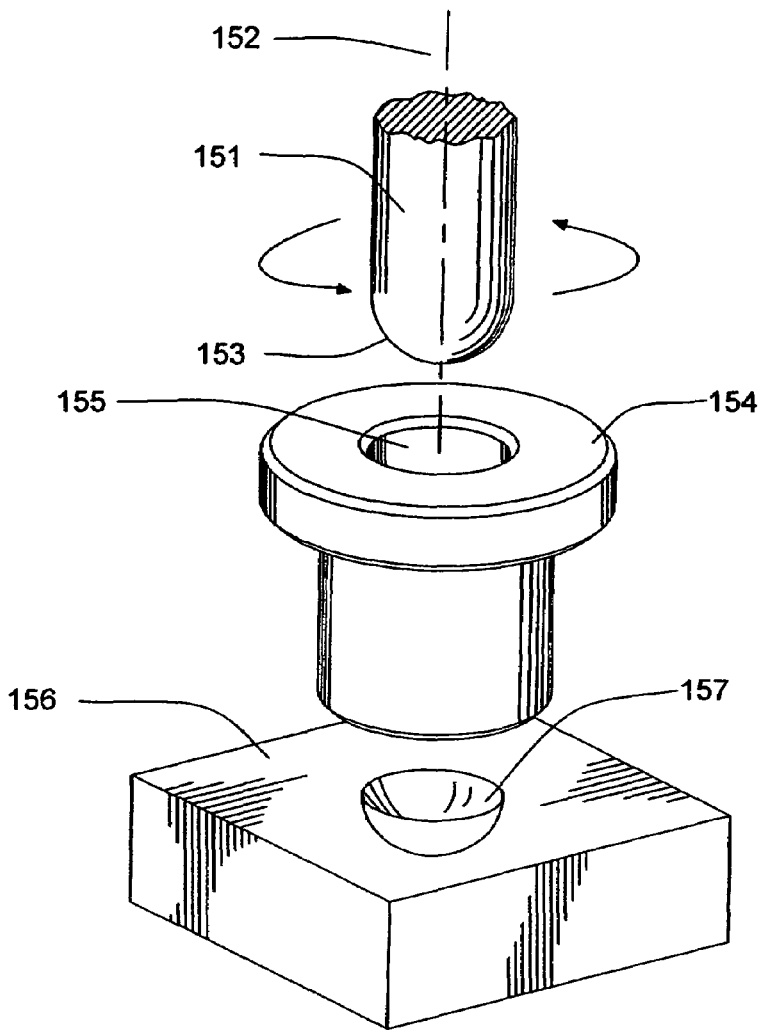
FIG. 1E depicts a device, which may be used for loading diamond feedstock prior to sintering.

Referring to FIG. 1E, an apparatus for carrying out a loading technique is depicted. The apparatus includes a spinning rod 151 with a longitudinal axis 152, the spinning rod being capable of spinning about its longitudinal axis. The spinning rod 151 has an end 153 matched to the size and shape of the part to be manufactured. For example, if the part to be manufactured is non-planar, the spinning rod end 153 may be non-planar.

A compression ring 154 is provided with a bore 155 through which the spinning rod 151 may project. A die 156 or can is provided with a cavity 157 also matched to the size and shape of the part to be made.

In order to load diamond feedstock, the spinning rod is placed into a drill chuck and the spinning rod is aligned with the center point of the die. The depth to which the spinning rod stops in relation to the cavity of the die is controlled with a set screw and monitored with a dial indicator.

The die is charged with a known amount of diamond feedstock material. The spinning rod is then spun about its longitudinal axis and lowered into the die cavity to a predetermined depth. The spinning rod contacts and rearranges the diamond feedstock during this operation. Then the spinning of the spinning rod is stopped and the spinning rod is locked in place.

The compression ring is then lowered around the outside of the spinning rod to a point where the compression ring contacts diamond feedstock in the cavity of the die. The part of the compression ring that contacts the diamond is annular. The compression ring is tamped up and down to compact the diamond. This type of compaction is used to distribute diamond material throughout the cavity to the same density and may be done in stages to prevent bridging. Packing the diamond with the compaction ring causes the density of the diamond around the equator of the sample to be very uniform and the same as that of the polar region in the cavity. In this configuration, the diamond sinters in a truly non-planar fashion and the resulting part maintains its sphericity to close tolerances.

Controlling Large Volumes of Powder Feedstocks, Such As Diamond

The following information provides further instruction on control and pre-processing of diamond feedstock before sintering. PDC and Polycrystalline Cubic Boron Nitride (PCBN) powders reduce in volume during the sintering process. The amount of shrinkage experienced is dependent on a number of factors such as:

1. The amount of metal mixed with the diamond.
2. The loading density of the powders.
3. The bulk density of diamond metal mix.
4. The volume of powder loaded.
5. Particle size distribution (PSD) of the powders.

Figures 1, 3A:
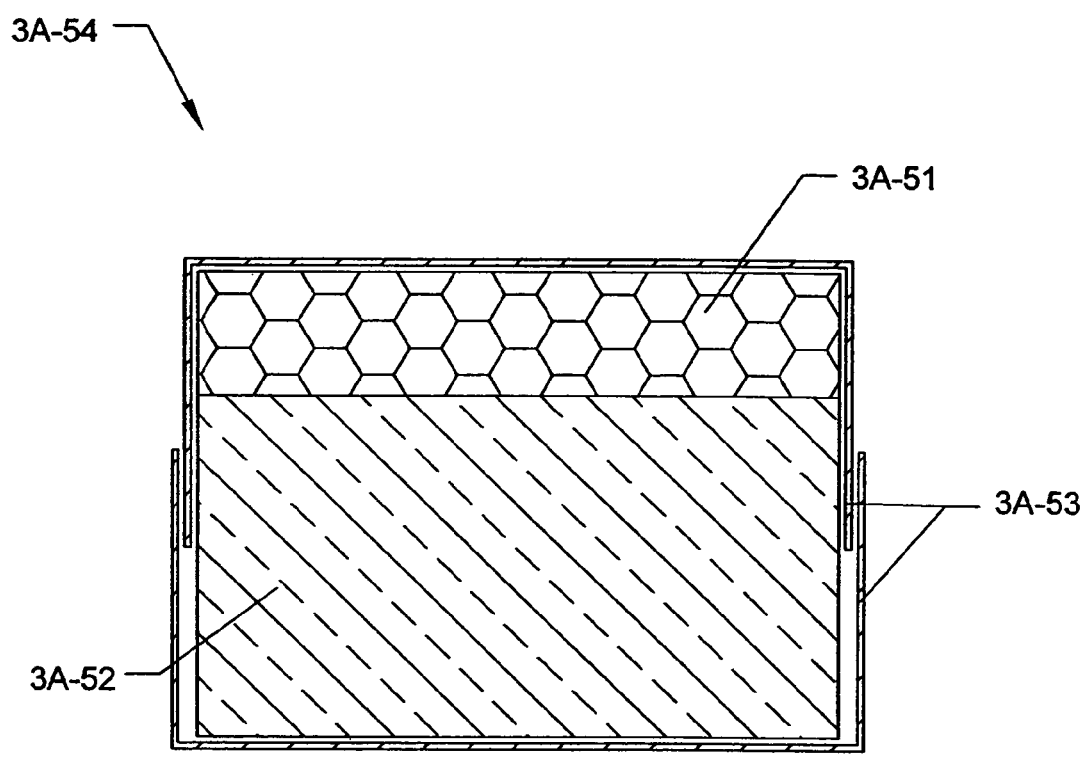
FIGS. 3A-1 through 3A-11 depict controlling large volumes of powder feedstocks, such as diamond.
Figures 2, 3A:
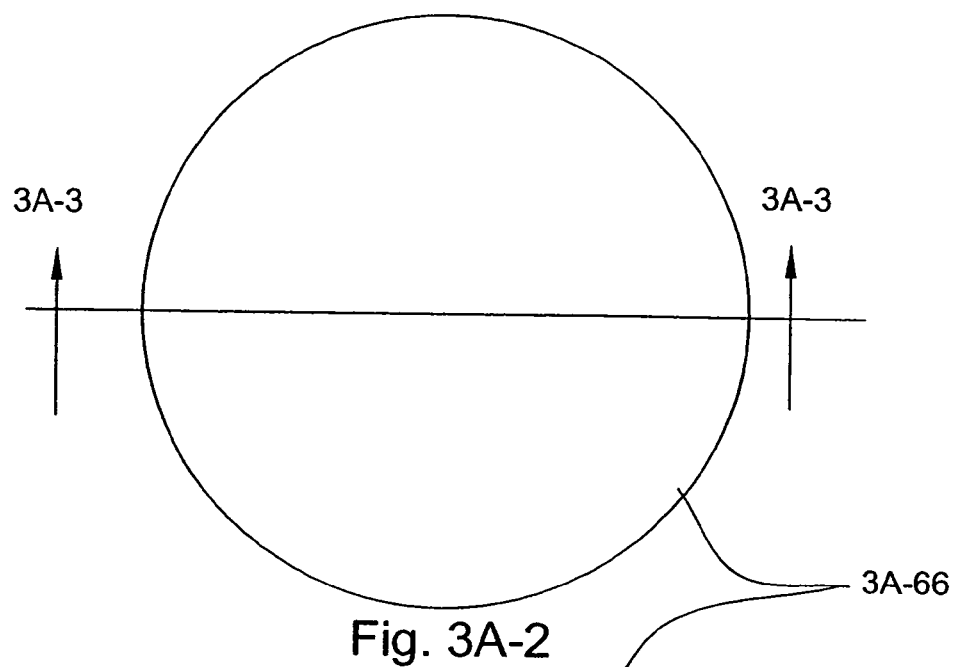
Figures 3, 3A:
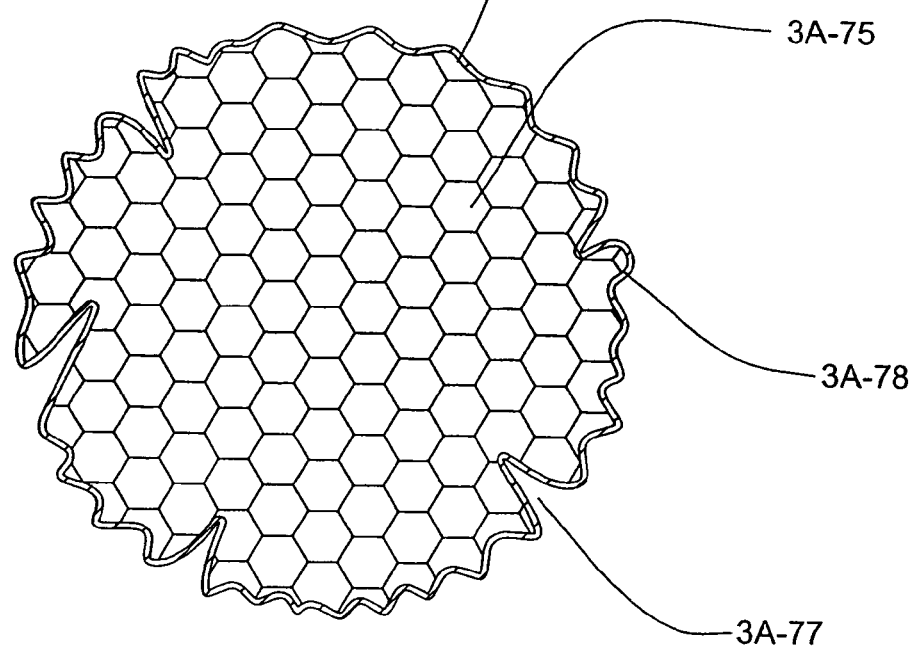

In most PDC and PCBN sintering applications, the volume of powder used is small enough that shrinkage is easily managed, as shown in FIG. 3A-1. FIG. 3A-1 illustrates a can 3A-54 in which can halves 3A-53 contain a substrate 3A-52 and a diamond table 3A-51. However, when sintering large volumes of diamond powders in spherical configurations, shrinkage is great enough to cause buckling of the containment cans 3A-66 as shown in FIG. 3A-2 and the cross section of FIG. 3A-3. The diamond has sintered 3A-75 but the can has buckles 3A-77 and wrinkles 3A-78, resulting in a non-uniform and damaged part. The following method is an improved loading, pre-compression, densification, and refractory can sealing method for spherical and non-planar parts loaded with large volumes of diamond and/or metal powders. The processing steps are described below.

Figures 3, 3A, 4:
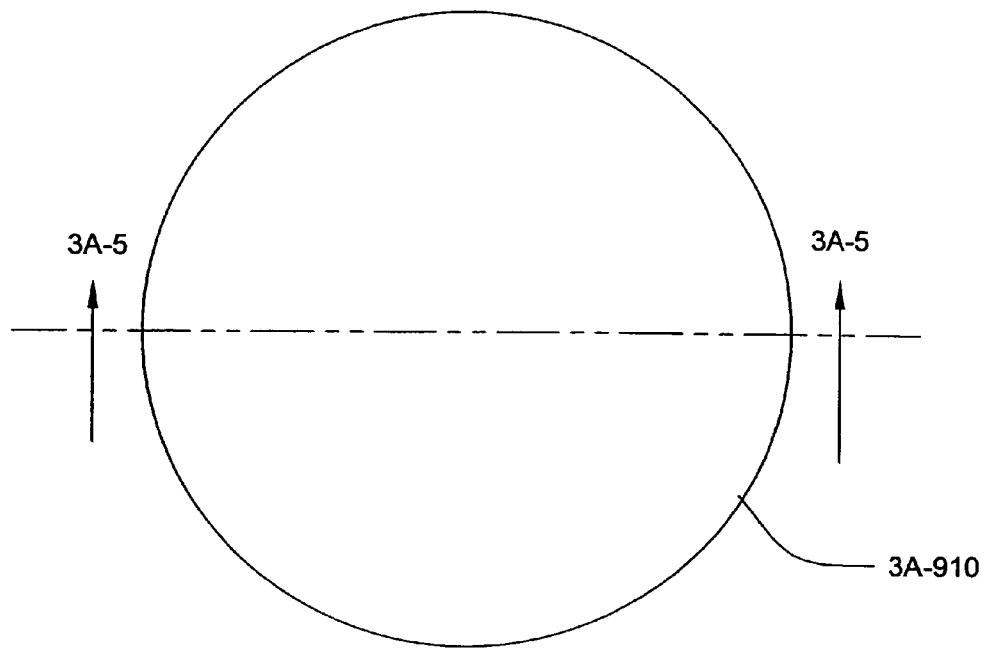

Referring to FIG. 3A4 and its cross section at FIG. 3A-5, PDC or PCBN powders 3A-911 are loaded against a substrate 3A-99 and into a refractory metal containment can assembly 3A-913 having can half skins 3A-910 and a seal 3A-912. Extra powder may be loaded normal to the seam in the can to accommodate shrinkage.

Referring to FIG. 3A-6, a can assembly 3A-913 is placed into a compaction fixture 3A-1014, which may be a cylindrical holder or slide 3A-1015 with two hemispherical punches 3A-1016 and 3A-1017. The fixture is designed to support the containment cans and allow the can half skins 3A-910 to slip at the seam during the pressing operation.

Referring to FIG. 3A-7-1, the relationship of the can half skins 3A-910 with the junction 3A-912 and the punch 3A-1016 is seen.

Referring to FIG. 3A-7, illustrates a compaction fixture 3A-1014 with a can 3A-913 placed into a press 3A-1218 and the upper 3A-1016 and lower 3A-1017 punches compress the can assembly 3A-913. The containment can halves 3A-910 slip past each other preventing buckling while the powdered feedstock is compressed.

Referring to FIG. 3A-8, the upper punch 3A-24 and upper press fitting 3A-25 are retracted and a crimping die 3A-20 is attached to the cylinder of the compaction fixture 3A-21. The can assembly 3A-913 rests against the lower punch 3A-22 that is attached to the lower press fitting 3A-23.

Referring to FIGS. 3A-9 and 3A-9-1, the lower punch 3A-22 is raised toward the upper punch 3A-24 driving excess can material 3A-27 into the hemispherical portion of the crimping die 3A-19 folding the excess around the upper can 3A-26.

Referring to FIG. 3A-10, the lower punch is raised expelling the can assembly 3A-13 from the cylinder 3A-28 of the compaction fixture 3A-21.

Referring to FIG. 3A-11, the can assembly 3A-913 emerges from pressing operation spherical with high loading density. The part may then be sintered in a cubic or other press without buckling or breaking the containment cans as the can half skins 3A-910 are overlapped.

Binding Diamond Feedstock Generally

Another method that may be employed to maintain a uniform density of the feedstock diamond is the use of a binder. A binder is added to the correct volume of feedstock diamond, and then the combination is pressed into a can. Some binders that may be used include polyvinyl butyryl, polymethyl methacrylate, polyvinyl formol, polyvinyl chloride acetate, polyethylene, ethyl cellulose, methylabietate, paraffin wax, polypropylene carbonate and polyethyl methacrylate.

In one embodiment, the process of binding diamond feedstock includes four steps. First, a binder solution is prepared. A binder solution may be prepared by adding about 5 to 25% plasticizer to pellets of poly (propylene carbonate), and dissolving this mixture in solvent such as 2-butanone to make about a 20% solution by weight.

Plasticizers that may be used include nonaqueous binders generally, glycol, dibutyl phthalate, benzyl butyl phthalate, alkyl benzyl phthalate, diethylhexyl phthalate, diisoecyl phthalate, diisononyl phthalate, dimethyl phthalate, dipropylene glycol dibenzoate, mixed glycols dibenzoate, 2-ethylhexyl diphenyl dibenzoate, mixed glycols dibenzoate, 2-ethylhexyl diphenyl phosphate, isodecyl diphenyl phosphate, isodecyl diphenl phosphate, tricrestyl phosphate, tributoxy ethyl phosphate, dihexyl adipate, triisooctyl trimellitate, dioctyl phthalate, epoxidized linseed oil, epoxidized soybean oil, acetyl triethyl citrate, propylene carbonate, various phthalate esters, butyl stearate, glycerin, polyalkyl glycol derivatives, diethyl oxalate, paraffin wax and triethylene glycol. Other appropriate plasticizers may be used as well.

Solvents that may be used include 2-butanone, methylene chloride, chloroform, 1,2-dichloroethne, trichlorethylene, methyl acetate, ethyl acetate, vinyl acetate, propylene carbonate, n-propyl acetate, acetonitrile, dimethylformamide, propionitrile, n-mehyl-2-pyrrolidene, glacial acetic acid, dimethyl sulfoxide, acetone, methyl ethyl ketone, cyclohexanone, oxysolve 80a, caprotactone, butyrolactone, tetrahydrofuran, 1,4 dioxane, propylene oxide, cellosolve acetate, 2-methoxy ethyl ether, benzene, styrene, xylene, ethanol, methanol, toluene, cyclohexane, chlorinated hydrocarbons, esters, ketones, ethers, ethyl benzene and various hydrocarbons. Other appropriate solvents may be used as well.

Second, diamond is mixed with the binder solution. Diamond may be added to the binder solution to achieve about a 2-25% binder solution (the percentage is calculated without regard to the 2-butanone).

Third, the mixture of diamond and binder solution is dried. This may be accomplished by placing the diamond and binder solution mixture in a vacuum oven for about 24 hours at about 50 degrees Celsius to drive out all of the solvent 2-butanone.

Fourth, the diamond and binder may be pressed into shape. When the diamond and binder is removed from the oven, it will be in a clump that may be broken into pieces that are then pressed into the desired shape with a compaction press. A pressing spindle of the desired geometry may be contacted with the bound diamond to form it into a desired shape. When the diamond and binder have been pressed, the spindle is retracted. The final density of diamond and binder after pressing may be at least about 2.6 grams per cubic centimeter.

Figure 1F:
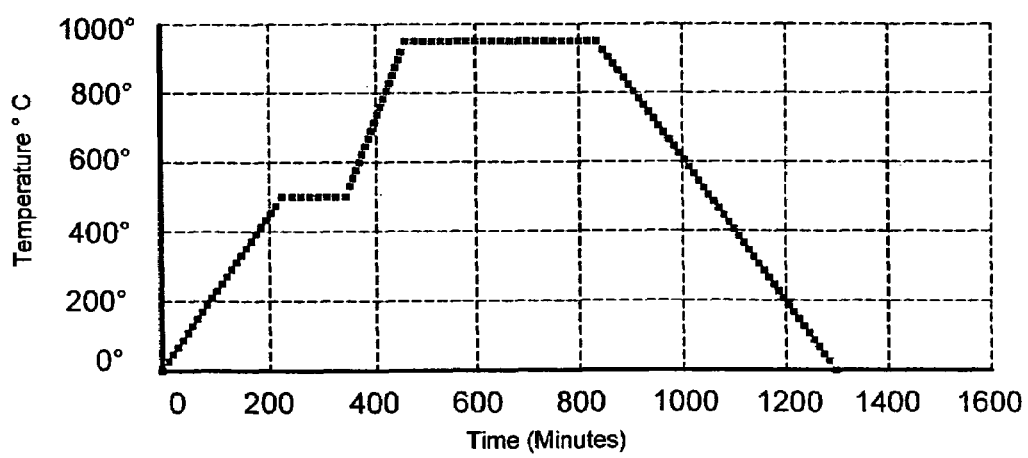
FIG. 1F depicts a furnace cycle for removal of a binder material from diamond feedstock prior to sintering.

If a volatile binder is used, it should be removed from the shaped diamond prior to sintering. The shaped diamond is placed into a furnace and the binding agent is either gasified or pyrolized for a sufficient length of time such that there is no binder remaining. PDC quality is reduced by foreign contamination of the diamond or substrate, and great care must be taken to ensure that contaminants and binder are removed during the furnace cycle. Ramp up and the time and temperature combination are critical for effective pyrolization of the binder. For the binder example given above, the debinding process may be used to remove the binder is as follows. (Referring to FIG. 1F while reading this description may be helpful.)

First, the shaped diamond and binder are heated from ambient temperature to about 500 degrees Celsius. The temperature may be increased by about 2 degrees Celsius per minute until about 500 degrees Celsius is reached. Second, the temperature of the bound and shaped diamond is maintained at about 500 degrees Celsius for about 2 hours. Third, the temperature of the diamond is increased again. The temperature may be increased from about 500 degrees Celsius by about 4 degrees per minute until a temperature of about 950 degrees Celsius is reached. Fourth, the diamond is maintained at about 950 degrees Celsius for about 6 hours. Fifth, the diamond is then permitted to return to ambient temperature at a temperature decrease of about 2 degrees per minute.

In some embodiments, it may be desirable to preform bound diamond feedstock by an appropriate process, such as injection molding. The diamond feedstock may include diamond crystals of one or more sizes, solvent-catalyst metal, and other ingredients to control diamond recrystallization and solvent-catalyst metal distribution. Handling the diamond feedstock is not difficult when the desired final curvature of the part is flat, convex dome or conical. However, when the desired final curvature of the part has complex contours, such as illustrated herein, providing uniform thickness and accuracy of contours of the PDC is more difficult when using powder diamond feedstock. In such cases it may be desirable to preform the diamond feedstock before sintering.

If it is desired to preform diamond feedstock prior to loading into a can for sintering, rather than placing powder diamond feedstock into the can, the steps described herein and variations of them may be followed. First, as already described, a suitable binder is added to the diamond feedstock. Optionally, powdered solvent-catalyst metal and other components may be added to the feedstock as well. The binder will typically be a polymer chosen for certain characteristics, such as melting point, solubility in various solvents, and CTE. One or more polymers may be included in the binder. The binder may also include an elastomer and/or solvents as desired in order to achieve desired binding, fluid flow and injection molding characteristics. The working volume of the binder to be added to a feedstock may be equal to or slightly more than the measured volume of empty space in a quantity of lightly compressed powder. Since binders typically consist of materials such as organic polymers with relatively high CTEs, the working volume should be calculated for the injection molding temperatures expected. The binder and feedstock should be mixed thoroughly to assure uniformity of composition. When heated, the binder and feedstock will have sufficient fluid character to flow in high pressure injection molding. The heated feedstock and binder mixture is then injected under pressure into molds of desired shape. The molded part then cools in the mold until set, and the mold can then be opened and the part removed. Depending on the final PDC geometry desired, one or more molded diamond feedstock components can be created and placed into a can for PDC sintering. Further, use of this method permits diamond feedstock to be molded into a desired form and then stored for long periods of time prior to use in the sintering process, thereby simplifying manufacturing and resulting in more efficient production.

As desired, the binder may be removed from the injection molded diamond feedstock form. A variety of methods are available to achieve this. For example, by simple vacuum or hydrogen furnace treatment, the binder may be removed from the diamond feedstock form. In such a method, the form would be brought up to a desired temperature in a vacuum or in a very low pressure hydrogen (reducing) environment. The binder will then volatilize with increasing temperature and will be removed from the form. The form may then be removed from the furnace. When hydrogen is used, it helps to maintain extremely clean and chemically active surfaces on the diamond crystals of the diamond feedstock form.

An alternative method for removing the binder from the form involves utilizing two or polymer (such as polyethylene) binders with different molecular weights. After initial injection molding, the diamond feedstock form is placed in a solvent bath that removes the lower molecular weight polymer, leaving the higher molecular weight polymer to maintain the shape of the diamond feedstock form. Then the diamond feedstock form is placed in a furnace for vacuum or very low pressure hydrogen treatment for removal of the higher molecular weight polymer.

Partial or complete binder removal from the diamond feedstock form may be performed prior to assembly of the form in a pressure assembly for PDC sintering. Alternatively, the pressure assembly including the diamond feedstock form may be placed into a furnace for vacuum or very low pressure hydrogen furnace treatment and binder removal.

Dilute Binder

In some embodiments, dilute binder may be added to PCD, PCBN or ceramic powders to hold form. This technique may be used to provide an improved method of forming PDC, PCBN, ceramic, or cermet powders into layers of various geometries. A PDC, PCBN, ceramic or cermet powder may be mixed with a temporary organic binder. This mixture may be mixed and cast or calendared into a sheet (tape) of the desired thickness. The sheet may be dried to remove water or organic solvents. The dried tape may be then cut into shapes needed to conform to the geometry of a corresponding substrate. The tape/substrate assembly may be then heated in a vacuum furnace to drive off the binder material. The temperature may then be raised to a level where the ceramic or cermet powder fuses to itself and/or to the substrate, thereby producing a uniform continuous ceramic or cermet coating bonded to the substrate.

Figures 3, 3A, 4, 5:
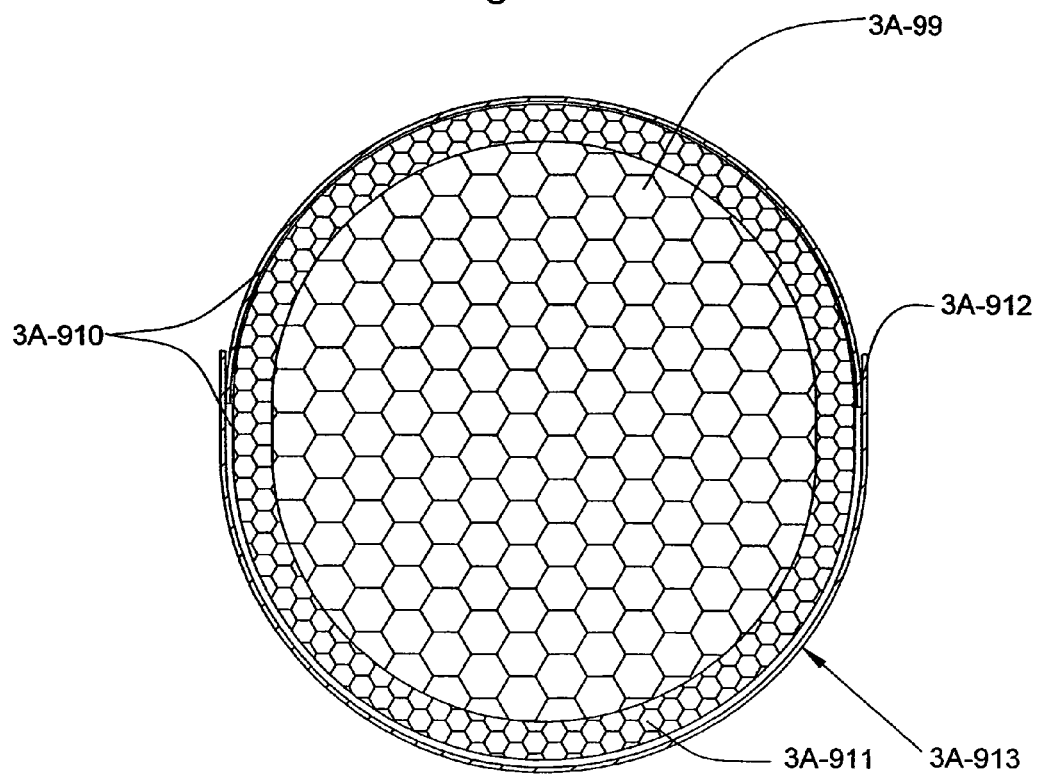
Figures 3, 3A, 4, 5, 6:
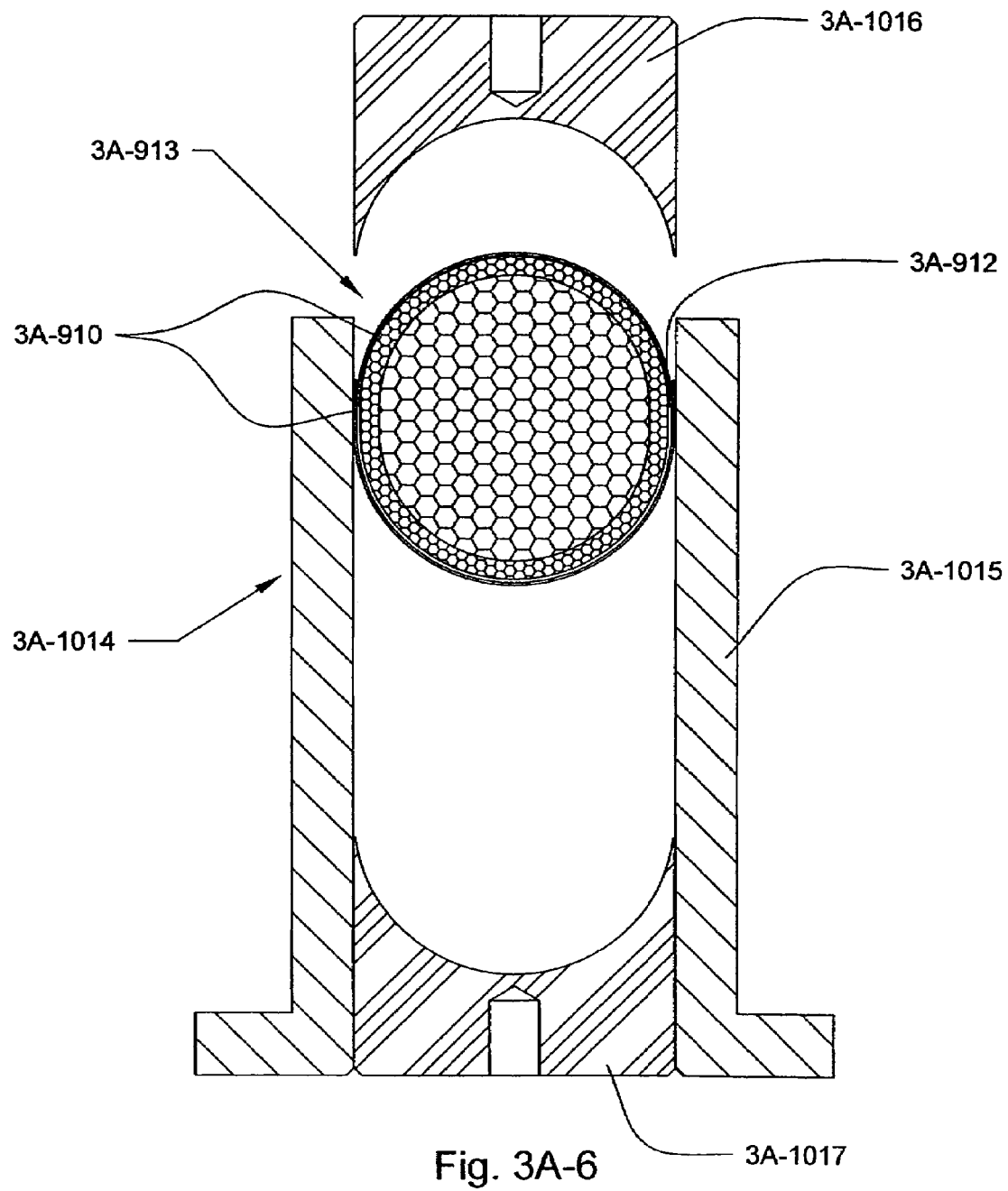

Referring to FIG. 5, a die 55 with a cup/can in it 54 and diamond feedstock 52 against it are depicted. A punch 53 is used to form the diamond feedstock 52 into a desired shape. Binder liquid 51 is not added to the powder until after the diamond, PCBN, ceramic or cermet powder 52 is in the desired geometry. Dry powder 52 is spin formed using a rotating formed punch 53 in a refractory containment can 54 supported in a holding die 55. In another method shown in FIG. 6, feedstock powder 62 is added to a mold 66. A punch forms the feedstock to shape. A vibrator 67 may be used help the powder 62 take on the shape of the mold 66. After the powder feedstock is in the desired geometry, a dilute solution of an organic binder with a solvent is allowed to percolate through the powder granules.

Figures 1, 3, 3A, 4, 5, 6, 7:
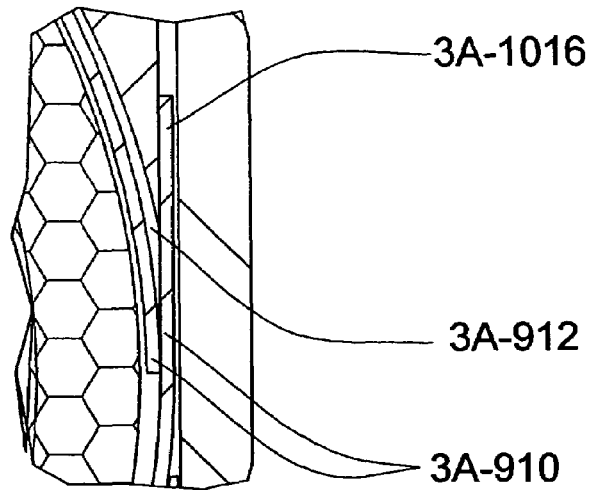
Figures 3, 3A, 4, 5, 6, 7:
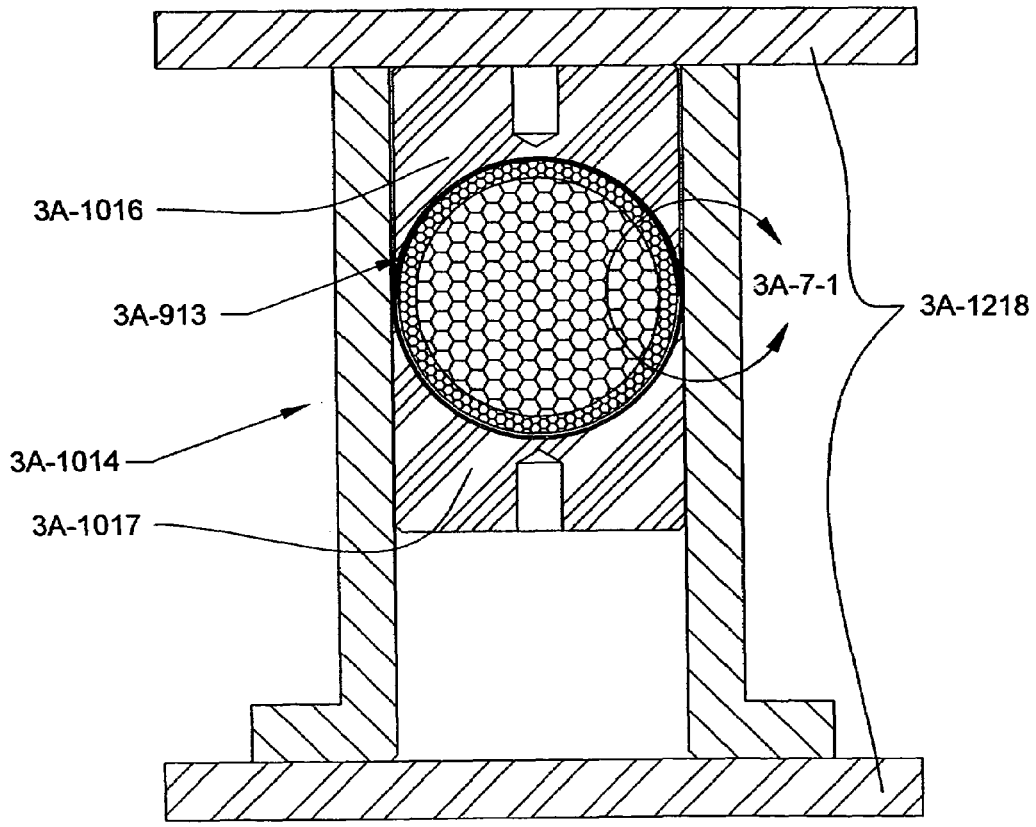
Figures 3, 3A, 4, 5, 6, 7, 8:
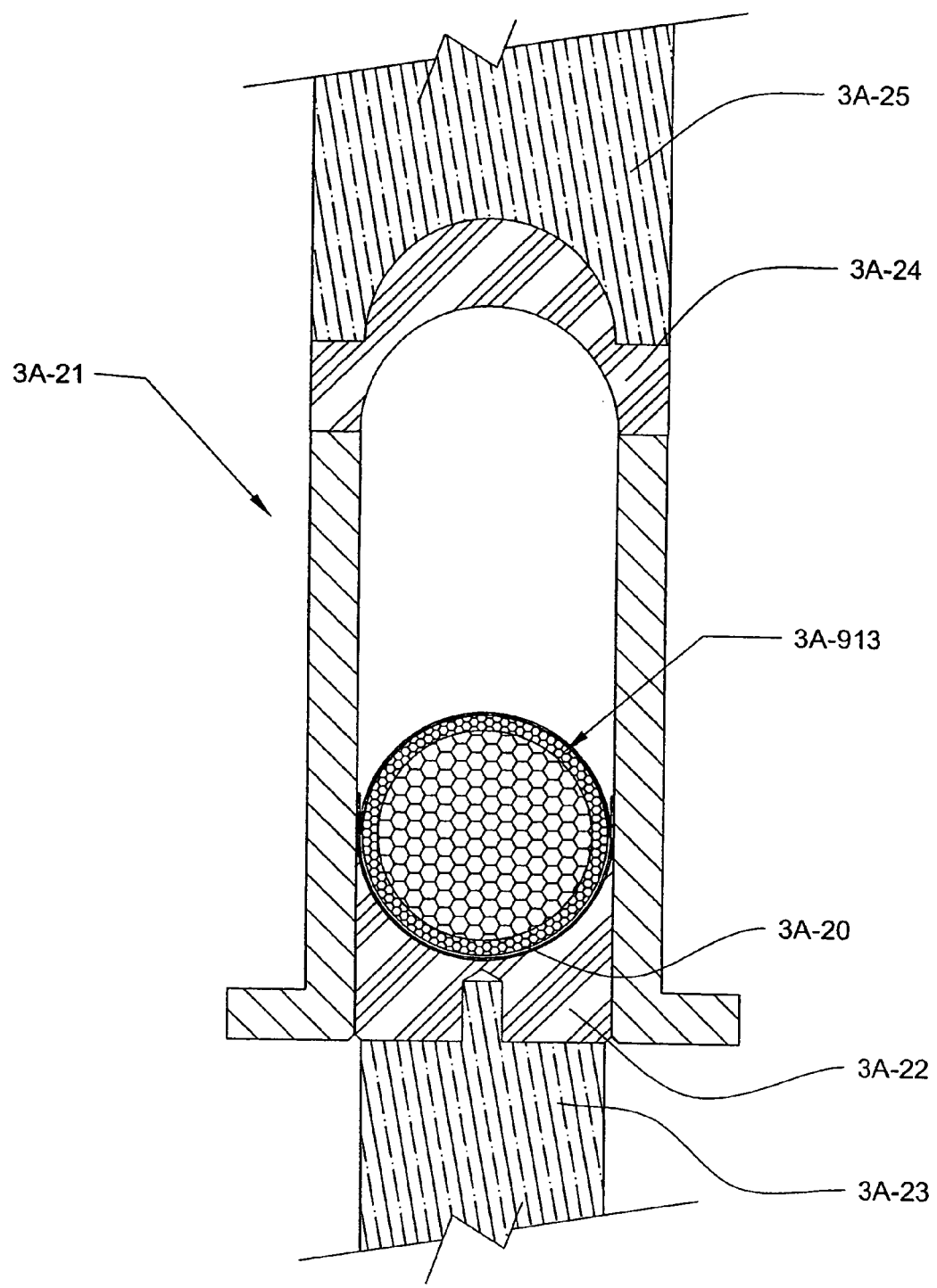

As shown in FIGS. 7 and 8, one powder layer 88 can be loaded, and after a few minutes, when the binder is cured sufficiently at room temperature, another layer 89 can be loaded on top of the first layer 88. This method is particularly useful in producing PDC or PCBN with multiple layers of varying powder particle size and metal content. The process can be repeated to produce as many layers as desired. FIG. 7 shows a section view of a spherical, multi-layered powder load using a first layer 88, second layer 89, third layer 810, and final layer 811. The binder content should be kept to a minimum to produce good loading density and to limit the amount of gas produced during the binder removal phase to reduce the tendency of the containment cans 84 being displaced from a build up of internal pressure.

Figures 1, 3, 3A, 4, 5, 6, 7, 8, 9:
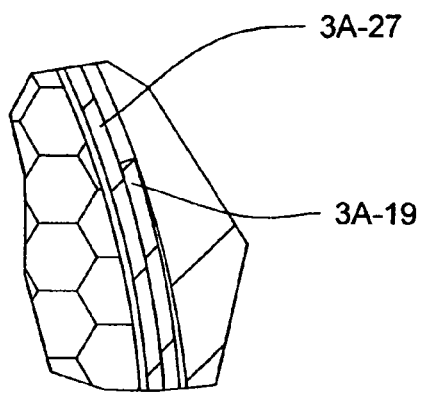
Figures 3, 3A, 4, 5, 6, 7, 8, 9:
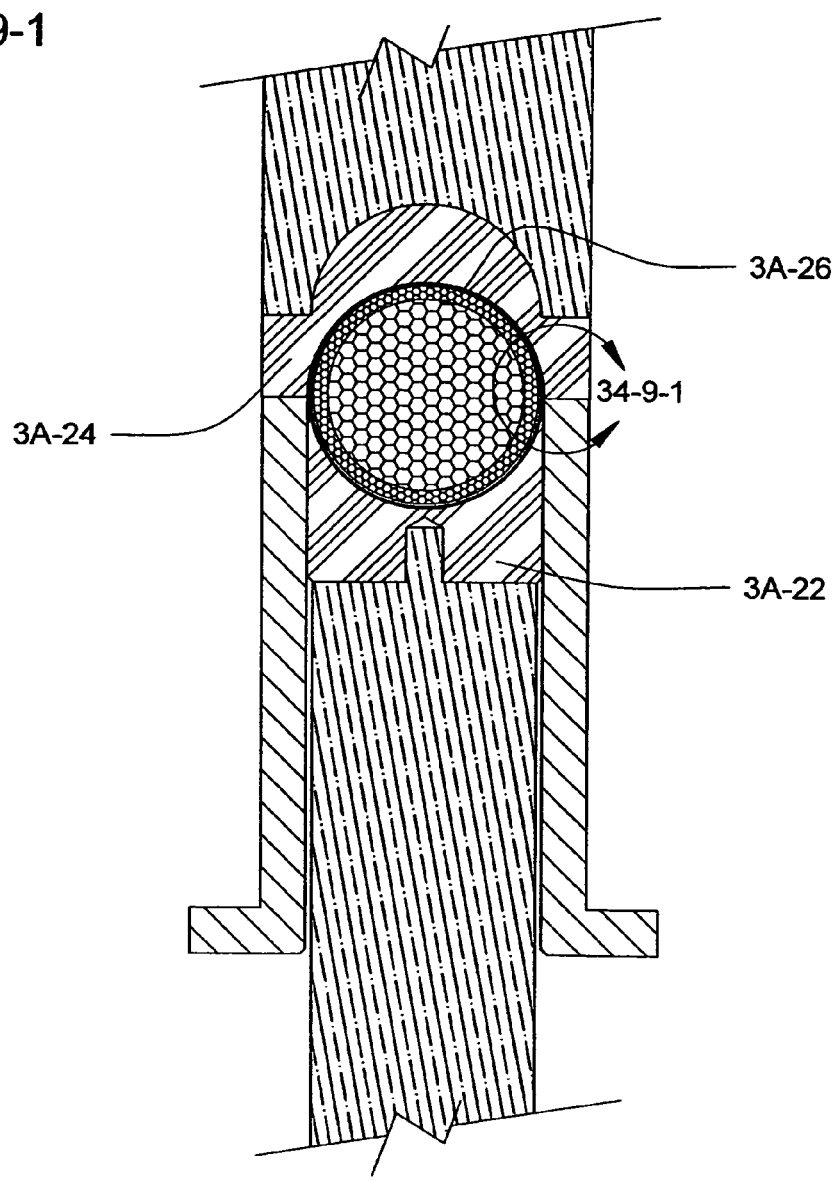

Once all of the powder layers are loaded the binder may be burned-out in a vacuum oven at a vacuum of about 200 Militorrs or less and at the time and desired temperature profile, such as that shown in FIG. 9. An acceptable binder is 0.5 to 5% propylene carbonate in methyl ethyl keytone. An example binder burn out cycle that may be used to remove binder is as follows:

| Time (minutes) | Temperature (degrees Centigrade) |
| --- | --- |
| 0 | 21 |
| 4 | 100 |
| 8 | 250 |
| 60 | 250 |
| 140 | 800 |
| 170 | 800 |
| 290 | 21 |

Gradients

Diamond feedstock may be selected and loaded in order to create different types of gradients in the diamond table. These include an interface gradient diamond table, an incremental gradient diamond table, and a continuous gradient diamond table.

If a single type or mix of diamond feedstock is loaded adjacent a substrate, as discussed elsewhere herein, sweep of solvent-catalyst metal through the diamond will create an interface gradient in the gradient transition zone of the diamond table.

An incremental gradient diamond table may be created by loading diamond feedstocks of differing characteristics (diamond particle size, diamond particle distribution, metal content, etc.) in different strata or layers before sintering. For example, a substrate is selected, and a first diamond feedstock containing 60% solvent-catalyst metal by weight is loaded in a first strata adjacent the substrate. Then a second diamond feedstock containing 40% solvent-catalyst metal by weight is loaded in a second strata adjacent the first strata. Optionally, additional strata of diamond feedstock may be used. For example, a third strata of diamond feedstock containing 20% solvent-catalyst metal by weight may be loaded adjacent the second strata.

A continuous gradient diamond table may be created by loading diamond feedstock in a manner that one or more of its characteristics continuously vary from one depth in the diamond table to another. For example, diamond particle size may vary from large near a substrate (to create large interstitial spaces in the diamond for solvent-catalyst metal to sweep into) to small near the diamond surface to create a part that is strongly bonded to the substrate but that has a very low friction surface.

The diamond feedstocks of the different strata may be of the same or different diamond particle size and distribution. Solvent-catalyst metal may be included in the diamond feedstock of the different strata in weight percentages of from about 0% to more than about 80%. In some embodiments, diamond feedstock will be loaded with no solvent-catalyst metal in it, relying on sweep of solvent-catalyst metal from the substrate to achieve sintering. Use of a plurality of diamond feedstock strata, the strata having different diamond particle size and distribution, different solvent-catalyst metal by weight, or both, allows a diamond table to be made that has different physical characteristics at the interface with the substrate than at the surface. This allows a PDC to be manufactured that has a diamond table very firmly bonded to its substrate.

Bisquing Processes to Hold Shapes

If desired, a bisquing process may be used to hold shapes for subsequent processing of PDCs, PCBN, and ceramic or cermet products. This involves an interim processing step in High Temperature High Pressure (HTHP) sintering of PDC, PCBN, ceramic, or cermet powders called "bisquing." Bisquing may provide the following enhancements to the processing of the above products:

A. Pre-sintered shapes can be controlled that are at a certain density and size.

B. Product consistency is improved dramatically.

C. Shapes can be handled easily in the bisque form.

D. In layered constructs, bisquing keeps the different layers from contaminating each other.

E. Bisquing different components or layers separately increases the separation of work elements increasing production efficiency and quality.

F. Bisquing molds are often easer to handle and manage prior to final assembly than the smaller final product forms.

Bisquing molds or containers can be fabricated from any high temperature material that has a melting point higher than the highest melting point of any mix component to be bisqued. Bisque mold/container materials that work well are Graphite, Quartz, Solid Hexagonal Boron Nitride (HBN), and ceramics. Some refractory type metals (high temperature stainless steels, Nb, W, Ta, Mo, etc) work well is some applications where bisquing temperatures are lower and sticking of the bisque powder mix is not a problem. Molds or containers can be shaped by pressing, forming, or machining, and may be polished at the interface between the bisque material and the mold/container itself. Some mold container materials require glazing and/or firing prior to use.

Figures 3, 3A, 4, 5, 6, 7, 8, 9, 10:
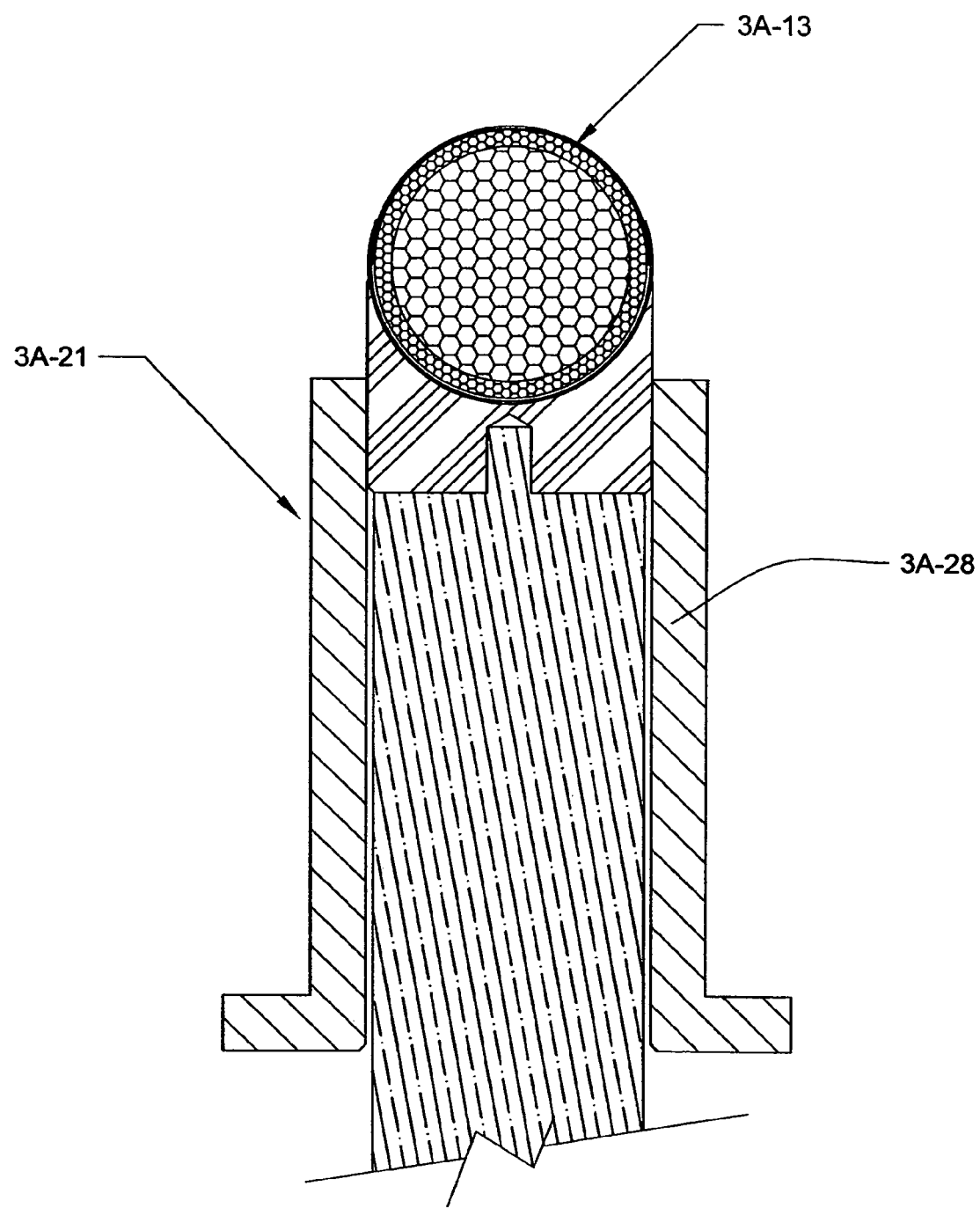
Figure 12:
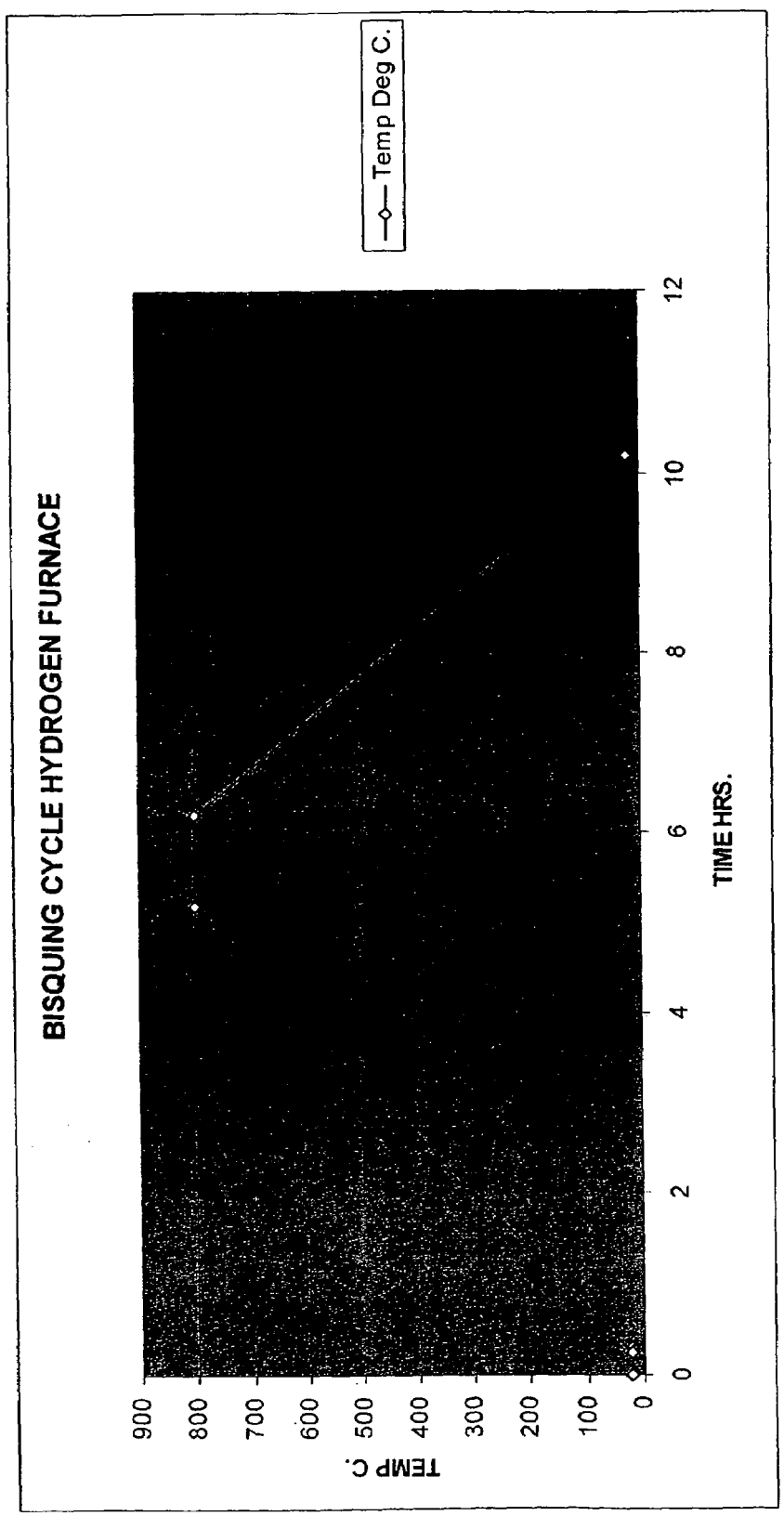

FIG. 10 shows an embodiment 1006 for making a cylinder with a concave relief or trough using the bisquing process. Pre-mixed powders of PDC, PCBN, ceramic, or cermet materials 1001 that contain enough metal to undergo solid phase sintering are loaded into the bisquing molds or containers 1002 and 1004. A release agent may be required between the mold/container to ensure that the final bisque form can be removed following furnace firing. Some release agents that may be used are HBN, Graphite, Mica, and Diamond Powder. A bisque mold/container lid with an integral support form 1005 is placed over the loaded powder material to ensure that the material holds form during the sintering process. The bisque mold/container assembly is then placed in a hydrogen atmosphere furnace, or alternately, in a vacuum furnace which is drawn to a vacuum ranging from 200 to 0 Militorrs. The load is then heated within a range of 0.6 to 0.8 of the melting temperature of the largest volume mix metal. A typical furnace cycle is shown in FIG. 12. Once the furnace cycle is completed and the mold/container is cooled, the hardened bisque formed powders can be removed for further HPHT processing. A bisque form of feedstock 1003 is the net product.

Figures 3, 3A, 4, 5, 6, 7, 8, 9, 10, 11:
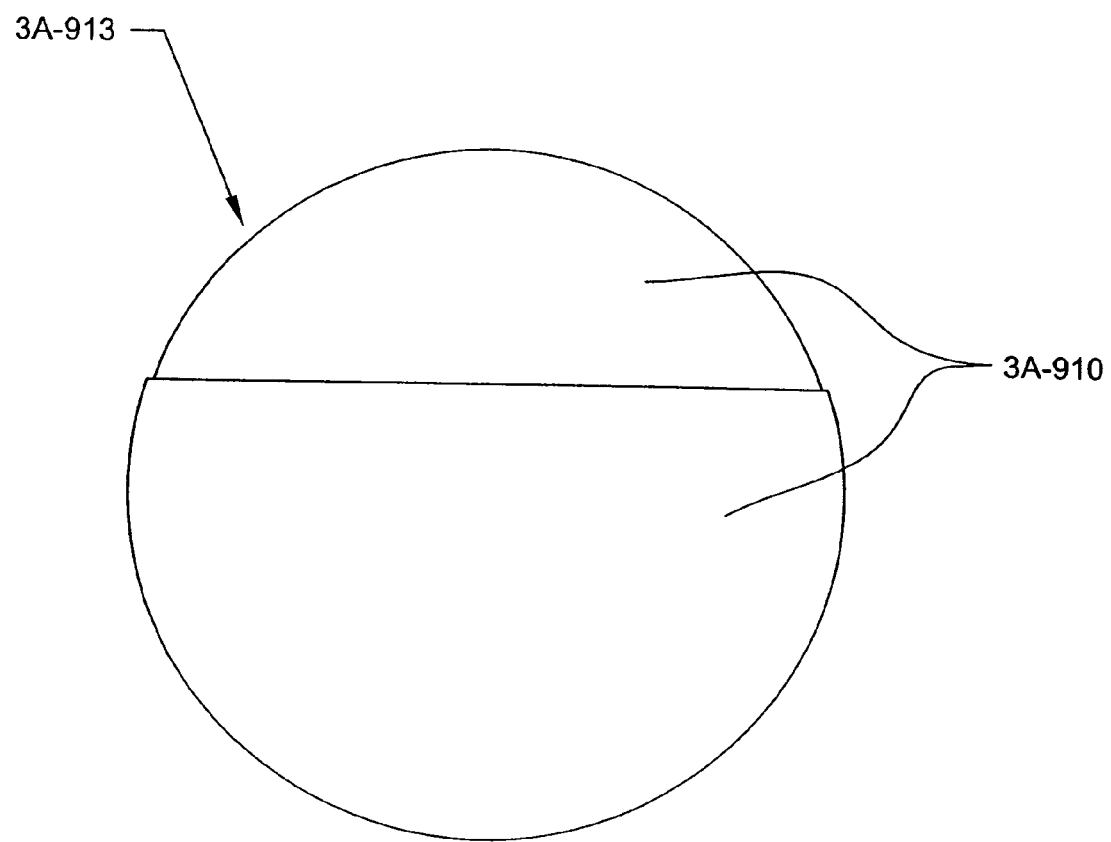

FIG. 11 shows fabrication 1110 of a bisque form for a full hemispherical part 1109 that has multiple powder layers 1107a and 1107b. Pre-mixed powders of PDC, PCBN, ceramic, or cermet materials that contain enough metal to undergo solid phase sintering are loaded into the bisquing molds or containers 1108. A release agent may be required between the mold/container to ensure that the final bisque form can be removed following furnace firing. The bisque mold/container assembly may then be placed in a vacuum furnace that is drawn to a vacuum ranging from 200 to 0 Militorrs. The load is then heated within a range of 0.6 to 0.8 of the melting temperature of the largest volume mix metal. Once the furnace cycle is completed and the mold/container is cooled, the hardened bisque 1109 formed powders can be removed for further HPHT processing. An example of a bisque binder burn-out cycle that may be used to remove the unwanted materials before sintering is as follows:

| Time (hours) | Temperature (degrees Centigrade) |
| --- | --- |
| 0 | 21 |
| 0.25 | 21 |
| 5.19 | 800 |
| 6.19 | 800 |
| 10.19 | 21 |

Reduction of Free Volume in Diamond Feedstock

As mentioned earlier, it may be desirable to remove free volume in the diamond feedstock before sintering is attempted. The inventors have found this is a useful procedure when producing non-planar concave and convex parts. If a press with sufficient anvil travel is used for high pressure and high temperature sintering, however, this step may not be necessary. Free volume in the diamond feedstock will be reduced so that the resulting diamond feedstock is at least about 95% theoretical density and closer to about 97% of theoretical density.

Referring to FIGS. 1GA and 1G, an assembly used for precompressing diamond to eliminate free volume is depicted. In the drawing, the diamond feedstock is intended to be used to make a convex non-planar polycrystalline diamond part. The assembly may be adapted for precompressing diamond feedstock for making PDCs of other complex shapes.

The assembly depicted includes a cube 161 of a pressure transfer medium. A cube is made from pyrophillite or other appropriate pressure transfer material such as a synthetic pressure medium and is intended to undergo pressure from a cubic press with anvils simultaneously pressing the six faces of the cube. A cylindrical cell rather than a cube may be used if a belt press is utilized for this step.

The cube 161 has a cylindrical cavity 162 or passage through it. The center of the cavity 162 will receive a non-planar refractory metal can 170 loaded with diamond feedstock 166 that is to be precompressed. The diamond feedstock 166 may have a substrate with it.

The can 170 consists of two non-planar can halves 170a and 170b, one of which overlaps the other to form a slight lip 172. The can may be an appropriate refractory metal such as niobium, tantalum, molybdenum, etc. The can is typically two hemispheres, one that is slightly larger to accept the other being slid inside of it to fully enclosed the diamond feedstock. A rebated area or lip is provided in the larger can so that the smaller can will satisfactorily fit therein. The seam of the can is sealed with an appropriate sealant such as dry hexagonal boronitride or a synthetic compression medium. The sealant forms a barrier that prevents the salt pressure medium from penetrating the can. The can seam may also be welded by plasma, laser, or electron beam processes.

An appropriately shaped pair of salt domes 164 and 167 surround the can 170 containing the diamond feedstock 166. In the example shown, the salt domes each have a non-planar cavity 165 and 168 for receiving the can 170 containing the non-planar diamond feedstock 166. The salt domes and the can and diamond feedstock are assembled together so that the salt domes encase the diamond feedstock. A pair of cylindrical salt disks 163 and 169 are assembled on the exterior of the salt domes 164 and 167. All of the aforementioned components fit within the bore 162 of the pressure medium cube 161.

The entire pyrocube assembly is placed into a press and pressurized under appropriate pressure (such as about 40-68 Kbar) and for an appropriate although brief duration to precompress the diamond and prepare it for sintering. No heat is necessary for this step.

Mold Releases

When making non-planar shapes, it may be desirable to use a mold in the sintering process to produce the desired net shape. CoCr metal may used as a mold release in forming shaped diamond or other superhard products. Sintering the superhard powder feed stocks to a substrate, the object of which is to lend support to the resulting superhard table, may be utilized to produce standard PDC and PCBN parts. However, in some applications, it is desired to remove the diamond table from the substrate.

Figure 14:
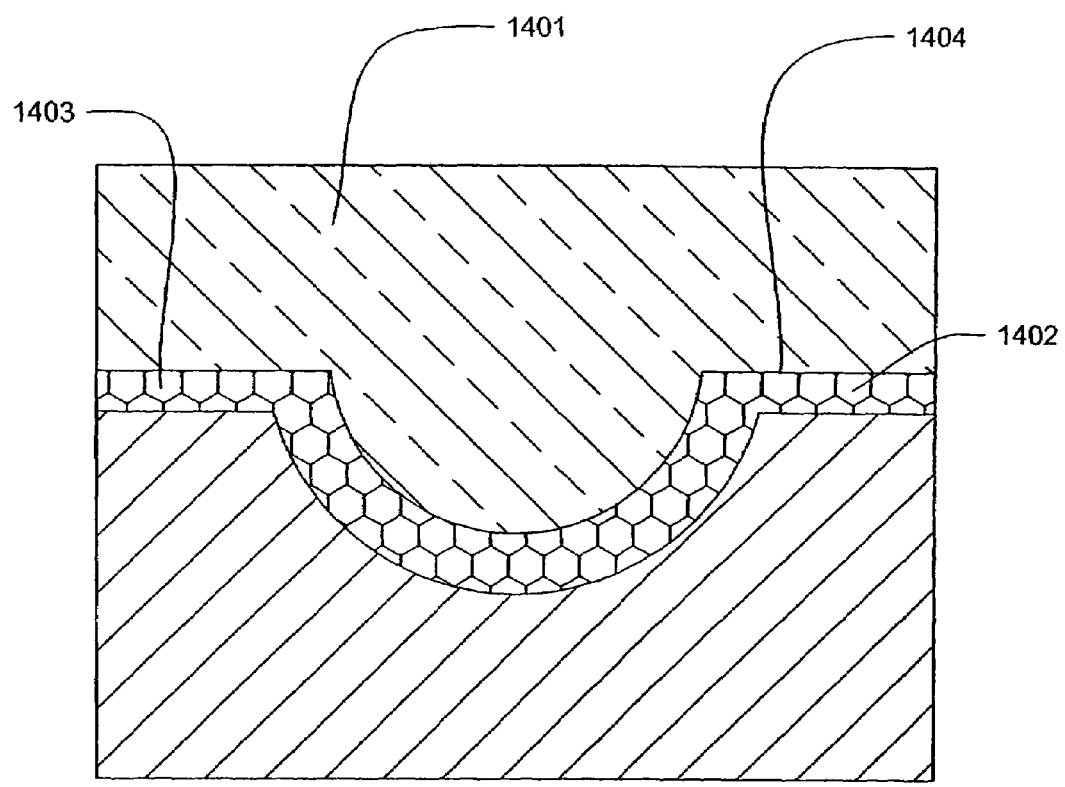
FIGS. 14-36 depict superhard material preparation before sintering and removal after sintering.
Figure 15:
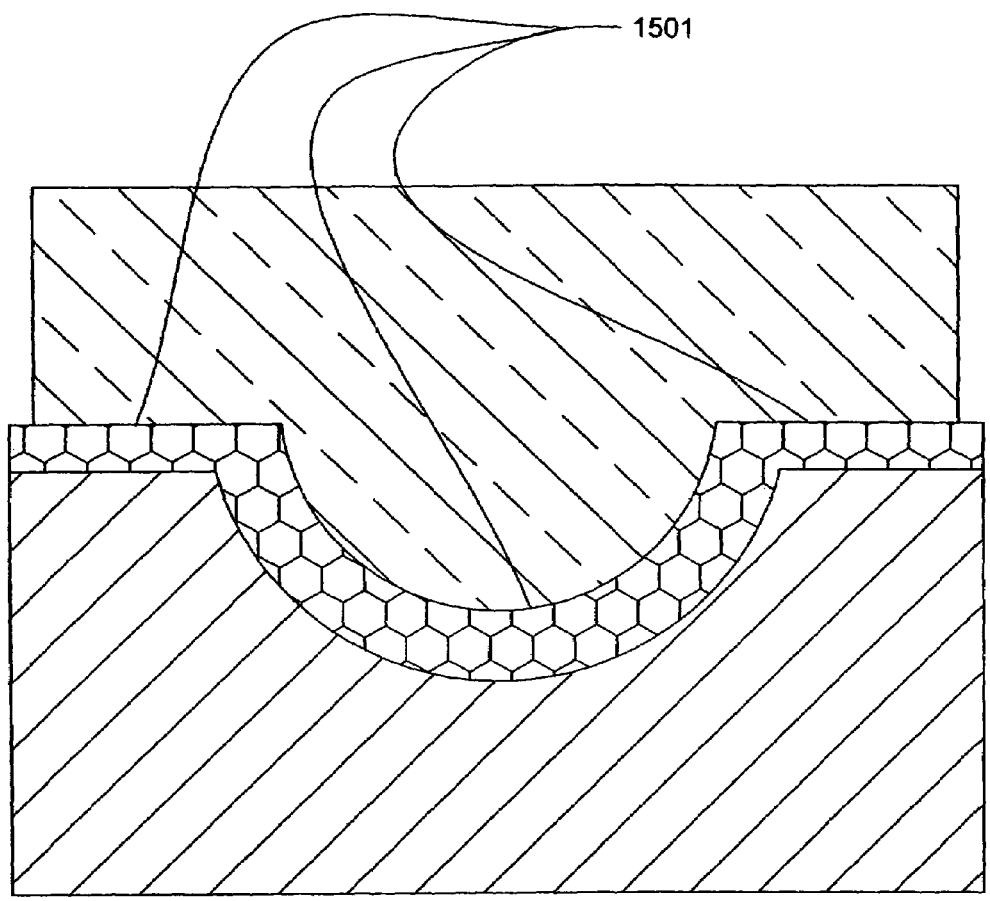
Figure 16:
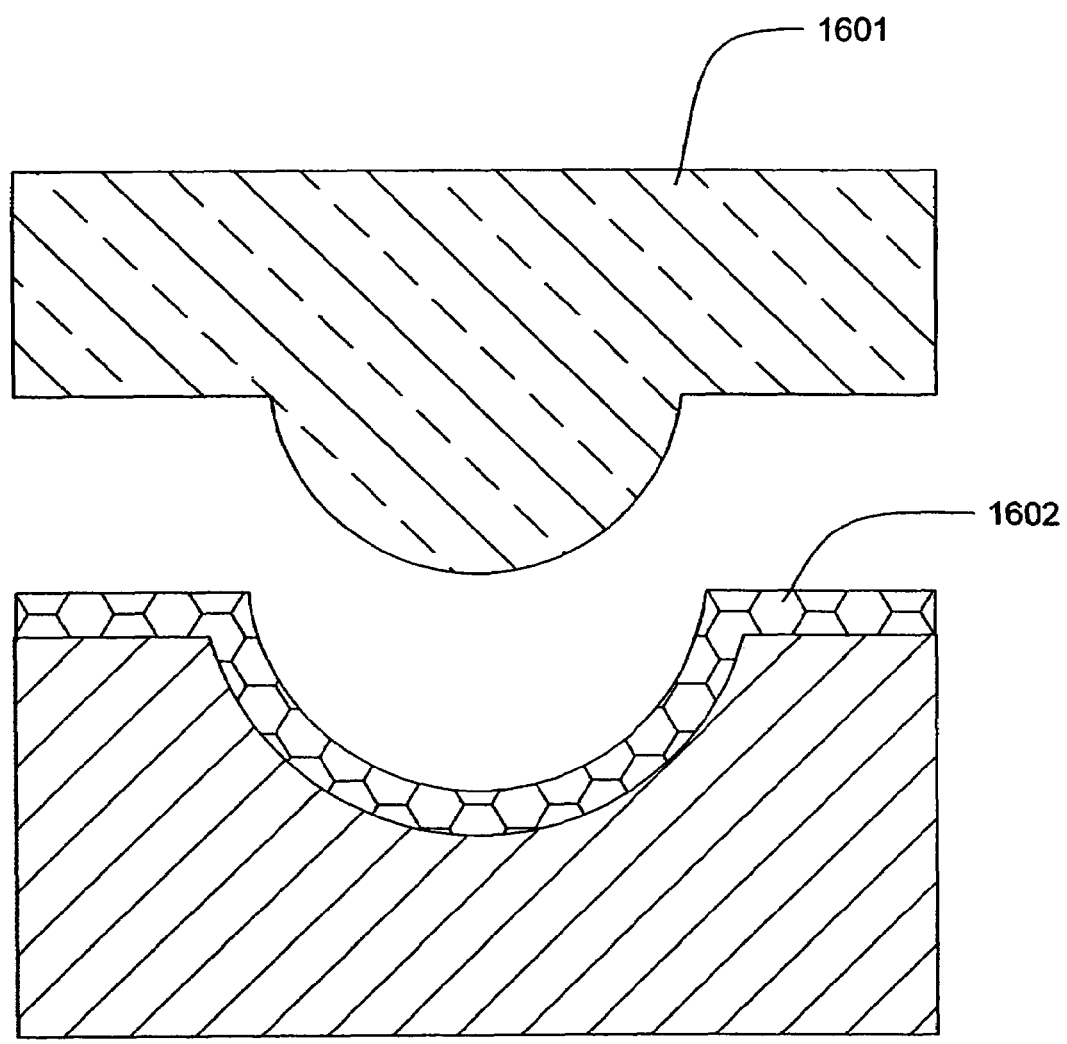

Referring to FIG. 14, a diamond layer 1402 and 1403 has been sintered to a substrate 1401 at an interface 1404. The interface 1404 must be broken to result in free standing diamond if the substrate is not required in the final product. A mold release may be used to remove the substrate from the diamond table. If CoCr alloy is used for the substrate, then the CoCr itself serves as a mold release, as well as serving as a solvent-catalyst metal. CoCr works well as a mold release because its CTE is dramatically different than that of sintered PDC or PCBN. Because of the large disparity in the CTEs between PDC and PCBN and CoCr, high stress is formed at the interface 1501 between these two materials as shown in FIG. 15. The stress that is formed is greater than the bond energy between the two materials. When the stress is greater than the bond energy, a crack is formed at the point of highest stress. The crack then propagates following the narrow region of high stress concentrated at the interface. Referring to FIG. 16, in this way, the CoCr substrate 1601 will separate from the PCD or PCBN 1602 that was sintered around it, regardless of the shape of the interface.

Materials other than CoCr can be used as a mold release. These materials include those metals with high CTEs and, in particular, those that are not good carbide formers. These are, for example, Co, Ni, CoCr, CoFe, CoNi, Fe, steel, etc.

Gradient Layers and Stress Modifiers

Gradient layers and stress modifiers may be used in the making of superhard constructs. Gradient layers may be used to achieve any of the following objectives:

A. Improve the "sweep" of solvent metal into the outer layer of superhard material and to control the amount of solvent metal introduced for sintering into the outer layer.

B. Provide a "sweep" source to flush out impurities for deposit on the surface of the outer layer of superhard material and/or chemical attachment/combination with the refractory containment cans.

C. Control the Bulk Modulus of the various gradient layers and thereby control the overall dilatation of the construct during the sintering process.

D. Affect the CTE of each of the various layers by changing the ratio of metal or carbides to diamond, PCBN or other Superhard materials to reduce the CTE of an individual gradient layer.

E. Allow for the control of structural stress fields through the various levels of gradient layers to optimize the overall construct.

F. Change the direction of stress tensors to improve the outer Superhard layer, e.g., direct the tensor vectors toward the center of a spherical construct to place the outer layer diamond into compression, or conversely, direct the tensor vectors from the center of the construct to reduce interface stresses between the various gradient layers.

G. Improve the overall structural stress compliance to external or internal loads by providing a construct that has substantially reduced brittleness and increased toughness wherein loads are transferred through the construct without crack initiation and propagation.

Figure 17:
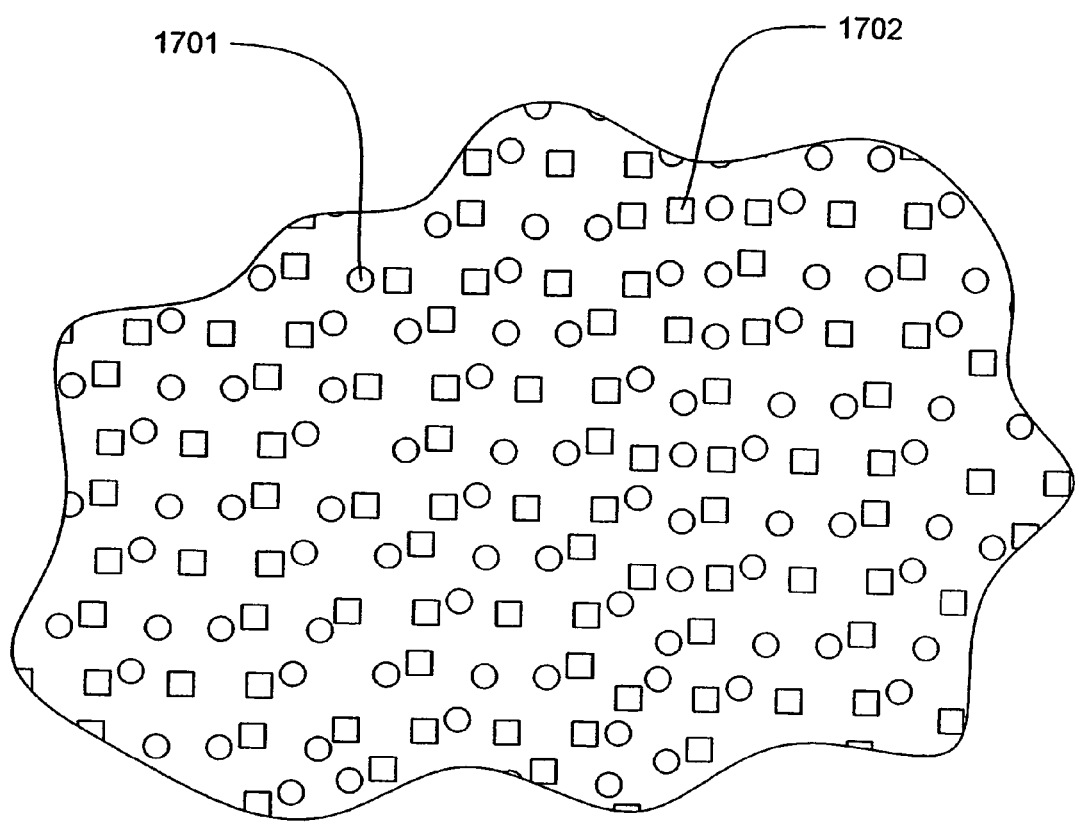
Figure 18:
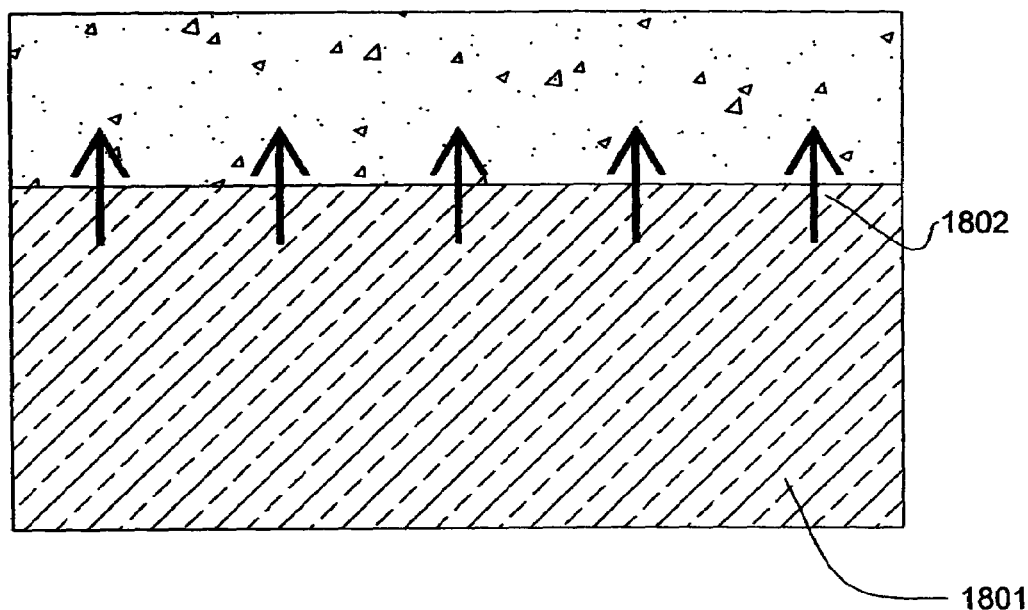

Referring to FIG. 17, the liquid sintering phase of PDC and PCBN is typically accomplished by mixing the solvent sintering metal 1701 directly with the diamond or PCBN powders 1702 prior to the HPHT pressing, or (referring to FIG. 18) "sweeping" the solvent metal 1802 from a substrate 1801 into feedstock powders from the adjacent substrate during HPHT. High quality PDC or PCBN is created using the "sweep" process.

There are several theories related to the increased PDC and PCBN quality when using the sweep method. However, most of those familiar with the field agree that allowing the sintering metal to "sweep" from the substrate material provides a "wave front" of sintering metal that quickly "wets" and dissolves the diamond or CBN and uses only as much metal as required to precipitate diamond or PCBN particle-to-particle bonding. Whereas in a "premixed" environment the metal "blinds off" the particle-to particle reaction because too much metal is present, or conversely, not enough metal is present to ensure the optimal reaction.

Figure 19:
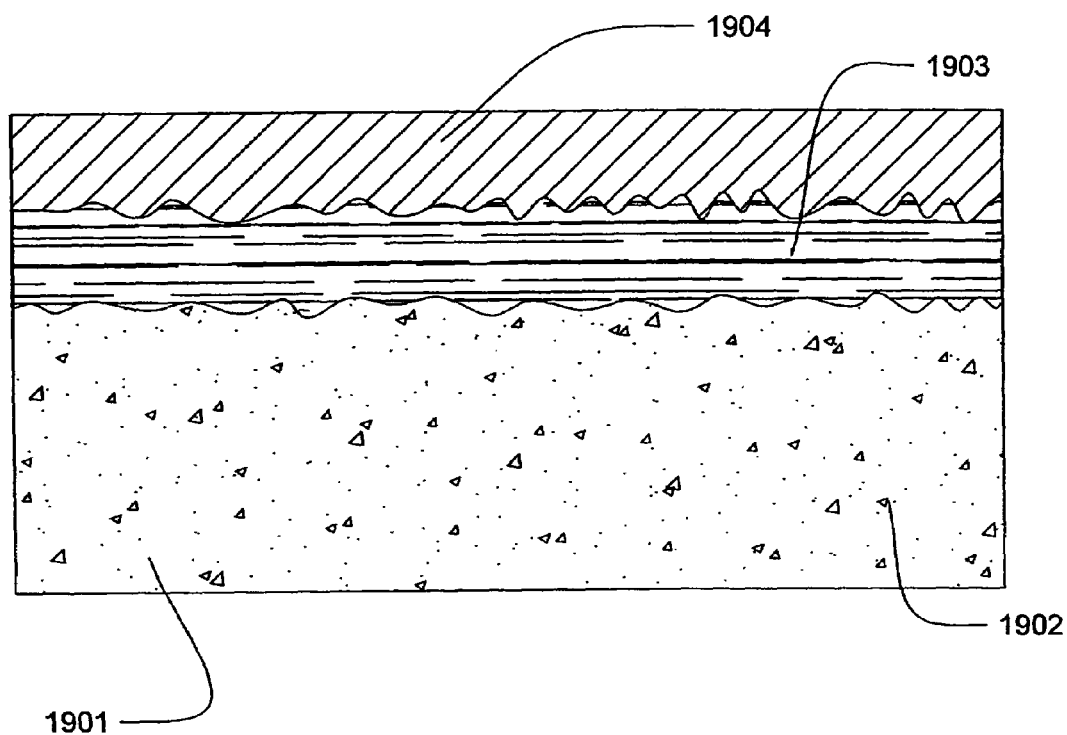

Furthermore, it is felt that the "wave front" of metal sweeping through the powder matrix also carries away impurities that would otherwise impede the formation of high quality PDC of PCBN. These impurities are normally "pushed" ahead of the sintering metal "wave front" and are deposited in pools adjacent to the refractory containment cans. FIG. 19 depicts the substrate 1904, the wavefront 1903, and the feedstock crystals or powder 1902 that the wavefront will sweep through 1901. Certain refractory material such as Niobium, Molybdenum, and Zirconium can act as "getters" that combine with the impurities as they immerge from the matrix giving additional assistance in the creation of high quality end products.

While there are compelling reasons to use the "sweep" process in sintering PDC and PCBN there are also problems that arise out of its use. For example, not all substrate metals are as controllable as others as to the quantity of material that is delivered and ultimately utilized by the powder matrix during sintering. Cobalt metal (6 to 13% by volume) sweeping from cemented tungsten carbide is very controllable when used against diamond or PCBN powders ranging from 1 to 40 microns particle sized. On the other hand, cobalt chrome molybdenum (CoCrMo) that is useful as a solvent metal to make PDC for some applications overwhelms the same PDC matrix with CoCrMo metal in a pure sweep process sometimes producing inferior quality PDC. The fact that the CoCrMo has a lower melting point than cobalt, and further that there is an inexhaustible supply when using a solid CoCrMo substrate adjacent to the PDC matrix, creates a non-controllable processing condition.

In some applications where it is necessary to use sintering metals such a CoCrMo that can not be "swept" from a cemented carbide product, it is necessary to provide a simulated substrate against the PDC powders that provides a controlled release and limited supply of CoCrMo for the process.

These "simulated" substrates have been developed in the forms of "gradient" layers of mixtures of diamond, carbides, and metals to produce the desired "sweep" affect for sintering the outer layer of PDC. The first "gradient layer" (just adjacent to the outer or primary diamond layer which will act as the bearing or wear surface) can be prepared using a mixture of diamond, $Cr_3C_2$, and CoCrMo. Depending on the size fraction of the diamond powder used in the outer layer, the first gradient layers diamond size fraction and metal content is adjusted for the optimal sintering conditions.

Where a "simulated" substrate is used, it has been discovered that often a small amount of solvent metal, in this case CoCrMo must be added to the outside diamond layer as catalyst to "kick-off" the sintering reaction.

Figure 20:
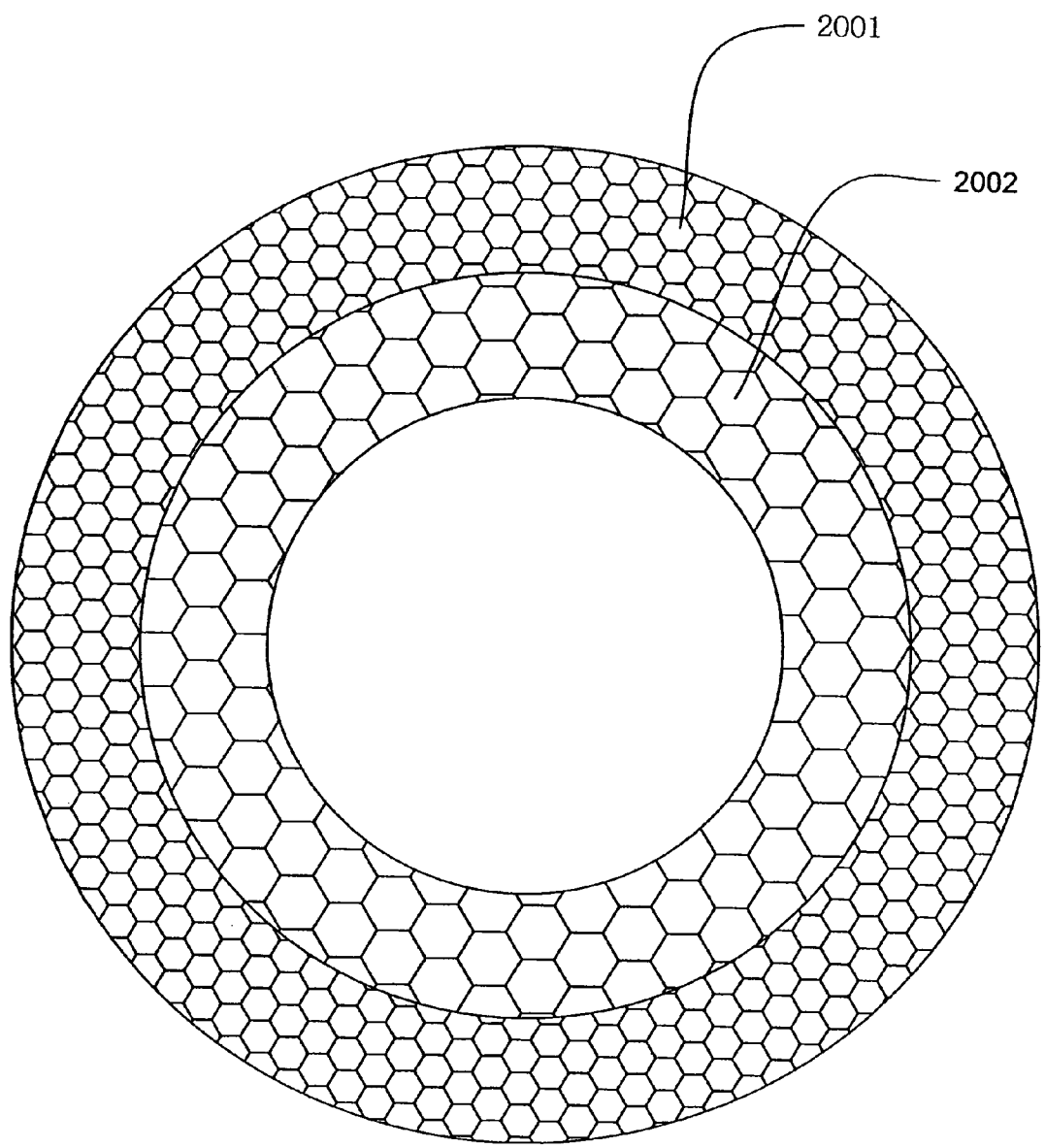

One embodiment utilizes the mix ranges for the outer 2001 and inner 2002 gradient layers of FIG. 20 that are listed in Table 9.

TABLE 9

| GRADIENT LAYERS | DIAMOND (Vol. Percent) | DIAMOND (Size Fraction-μm) | $Cr_3C_2$ (Vol. Percent) | CoCrMo (Vol. Percent) |
| --- | --- | --- | --- | --- |
| Outer | 92 | 25 | 0 | 8 |
| Inner | 70 | 40 | 10 | 20 |

The use of gradient layers with solid layers of metal allows the designer to match the bulk modulus to the CTE of various features of the construct to counteract dilatory forces encountered during the HTHP phase of the sintering process. For example, in a spherical construct as the pressure increases the metals in the construct are compressed or dilated radially toward the center of the sphere. Conversely, as the sintering temperature increases the metal expands radially away from the center of the sphere. Unless these forces are balanced in some way, the compressive dilatory forces will initiate cracks in the outer diamond layer and cause the construct to be unusable.

Typically, changes in bulk modulus of solid metal features in the construct are controlled by selecting metals with a compatible modulus of elasticity. The thickness and other sizing features are also important. CTE, on the other hand, is changed by the addition of diamond or other carbides to the gradient layers.

Figure 21:
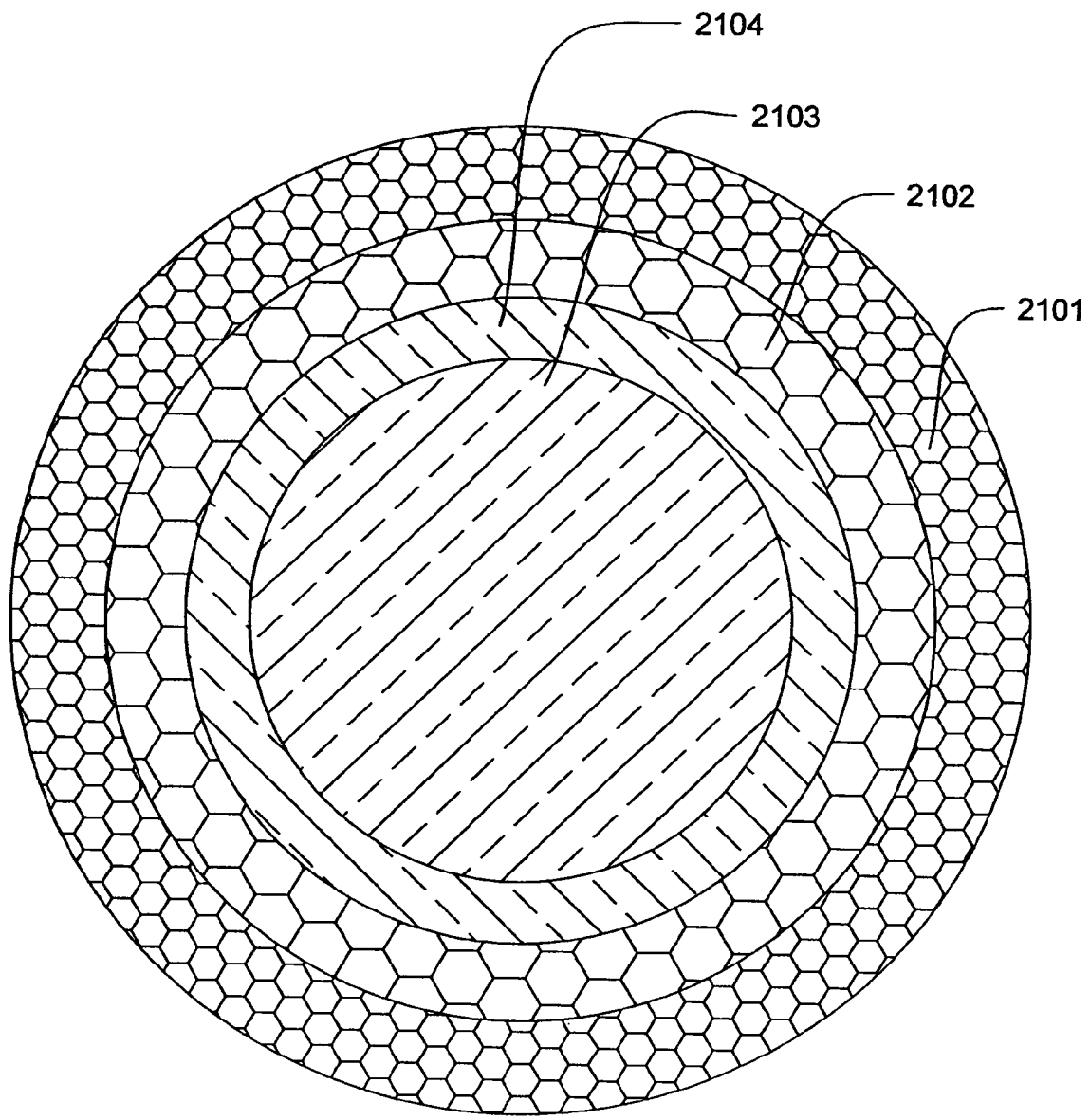

One embodiment, depicted in FIG. 21, involves the use of two gradient outer layers 2101 and 2102, a solid titanium layer 2104 and an inner CoCrMo sphere 2103. In this embodiment the first gradient layer provides a "sweep source" of biocompatible CoCrMo solvent metal to the outer diamond layer. The solid titanium layer provides a dilatory source that offsets the CTE from the solid CoCrMo center ball and keeps it from "pulling away" from the titanium/CoCrMo interface as the sintering pressure and temperature go from the 65 Kbar and 1400° C. sintering range to 1 bar and room temperature.

Where two or more powder based gradient layers are to be used in the construct it becomes increasingly important to control the CTE of each layer to ensure structural integrity following sintering. During the sintering process stresses are induced along the interface between each of the gradient layers. These high stresses are a direct result of the differences in the CTE between any two adjacent layers. To reduce these stresses the CTE of one or both of the layer materials must be modified.

The CTE of the a substrate can be modified by either changing to a substrate with a CTE close to that of diamond (an example is the use of cemented tungsten carbide, where the CTE of diamond is approximately 1.8 μm/m-° C. and cemented tungsten carbide is approximately 4.4 μm/m-° C.), or in the case of powdered layers, by adding a low CTE material to the substrate layer itself. That is, making a mixture of two or more materials, one or more of which will alter the CTE of the substrate layer.

Metal powders can be mixed with diamond or other superhard materials to produce a material with a CTE close to that of diamond and thus produce stresses low enough following sintering to prevent delamination of the layers at their interfaces. Experimental data shows that the CTE altering materials will not generally react with each other, which allows the investigator to predict the outcome of the intermediate CTE for each gradient level.

The desired CTE is obtained by mixing specific quantities of two materials according to the rule of mixtures. Table 10 shows the change in CTE between two materials, A and B as a function of composition (volume percent). In this example, materials A and B have CTEs of 150 and 600 μIn./In.-° F. respectively. By adding 50 mol % of A to 50 mol % of B the resulting CTE is 375 μin/in-° F.

One or more of the following component processes is incorporated into the mold release system:

1. An intermediate layer of material between the PDC part and the mold that prevents bonding of the polycrystalline diamond compact to the mold surface.

2. A mold material that does not bond to the PDC under the conditions of synthesis.

3. A mold material that, in the final stages of, or at the conclusion of, the PDC synthesis cycle either contracts away from the PDC in the case of a net concave PDC geometry, or expands away from the PDC in the case of a net convex PDC geometry.

4. The mold shape can also act simultaneously as a source of sweep metal useful in the PDC synthesis process.

As an example, a mold release system may be utilized in manufacturing a PDC by employing a negative shape of the desired geometry to produce non-planar parts. The mold surface contracts away from the final net concave geometry, the mold surface acts as a source of solvent-catalyst metal for the PDC synthesis process, and the mold surface has poor bonding properties to PDCs.

TABLE 10

PREDICTED DIMENSIONAL CHANGES IN
AN EIGHT INCH LAYERED CONSTRUCT

| A % | B % | CTE (μ In./In.-°F.) | Total Length Change (In.) | Final Dimension (In.) |
|---|---|---|---|---|
| 100 | 0 | 150 | .0012 | 7.9988 |
| 90 | 10 | 195 | .0016 | 7.9984 |
| 80 | 20 | 240 | .0019 | 7.9981 |
| 70 | 30 | 285 | .0023 | 7.9977 |
| 60 | 40 | 330 | .0026 | 7.9974 |
| 50 | 50 | 375 | .0030 | 7.9970 |
| 40 | 60 | 420 | .0034 | 7.9966 |
| 30 | 70 | 465 | .0037 | 7.9963 |
| 20 | 80 | 510 | .0041 | 7.9959 |
| 10 | 90 | 555 | .0044 | 7.9956 |
| 0 | 100 | 600 | .0048 | 7.9952 |

Figure 22:
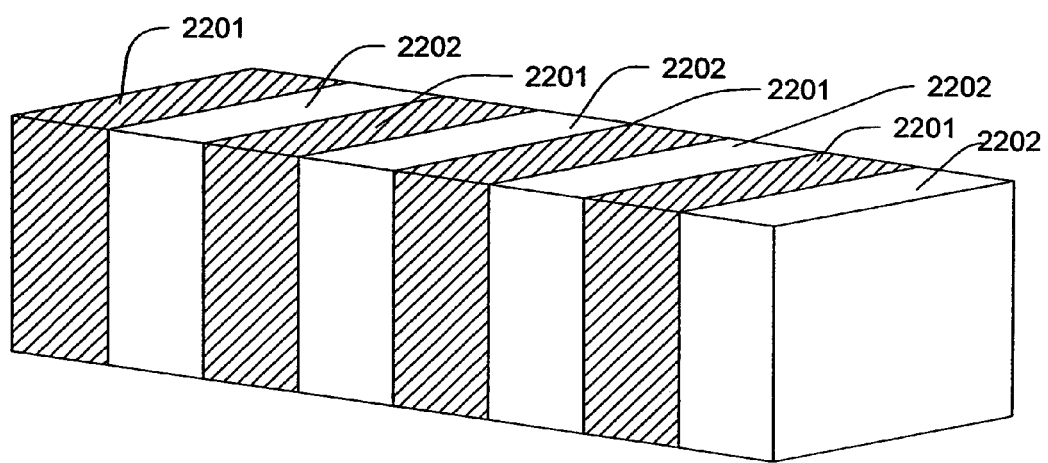

FIG. 22 is an illustration of how the above CTE modification works in a one-dimensional example. The one-dimensional example works as well in a three-dimensional construct. If the above materials A and B are packed in alternating layers 2201 and 2202 as shown in FIG. 22, separately in their pure forms, with their CTEs of 150 and 600 μln./ln.-° F. respectively, they will contract exactly 150 μln./ln.-° F. and 600 μln./ln.-° F. for every degree decrease in temperature. For an eight inch block of one inch thick stacked layers the total change in dimension for a one degree decrease in temperature will be:

Material A: (4×1 ln.)×(0.00015 ln./ln.-° F.)×1° F.=0.0006 ln.

Material B: (4×1 ln.)×(0.00060 ln./ln.-° F.)×1)° F.=0.0024 ln.

Total overall length decrease in eight inches=0.0030 in.

By comparison, each of the layers is modified by using a mixture of 50% of A and 50% of B, and all eight layers are stacked into the eight-inch block configuration. Re-calculation of the overall length decrease using the new composite CTE of 375 μln./ln.-° F. from Table II shows:

Material A+B: (8×1 ln.)×(0.000375 ln./ln.-° F.)×1° F.=0.0030 ln.

Total overall length decrease in eight inches=0.0030 ln.

The length decrease in this case was accurately predicted for the one-dimensional construct using one-inch thick layers by using the rule of mixtures.

Metals have very high CTE values as compared to diamond, which has one of the lowest CTEs of any known material. When metals are used as substrates for PDC and PCBN sintering considerable stress is developed at the interface. Therefore, mixing low CTE material with the biocompatible metal for medical implants can be used to reduce interfacial stresses. One of the best candidate materials is diamond itself. Other materials include refractory metal carbides and nitrides, and some oxides. Borides and silicides would also be good materials from a theoretical standpoint, but may not be biocompatible. The following is a list of candidate materials:

| Carbides | Silicides | Oxynitrides |
|---|---|---|
| Nitrides | Oxides | Oxyborides |
| Borides | Oxycarbides | Carbonitrides |

There are other materials and combinations of materials that could be utilized as CTE modifiers.

There are also other factors that apply to the reduction of interface stresses for a particular geometrical construct. The thickness of the gradient layer, its position in the construct, and the general shape of the final construct all contribute in interfacial stress tensor reduction. Geometries that are more spherical tend to promote interface circumferential failures from positive or negative radial tensors while geometries of a cylindrical configuration tend to fail at the layer interfaces precipitated by bending stress couples.

The design of the gradient layers respecting CTE and the amount of contraction that each individual layer will experience during cooling form the HTHP sintering process will largely dictate the direction of stress tensors in the construct. Generally, the designer will always desire to have the outer wear layer of superhard material in compression to prevent delamination and crack propagation. In spherical geometries the stress tensors would be directed radially toward the center of the spherical shape giving special attention to the interfacial stresses at each layer interface to prevent failures at these interfaces as well. In cylindrical geometries the stress tensors would be adjusted to prevent stress couples from initiating cracks in either end of the cylinder, especially at the end where the wear surface is present.

Figure 23:
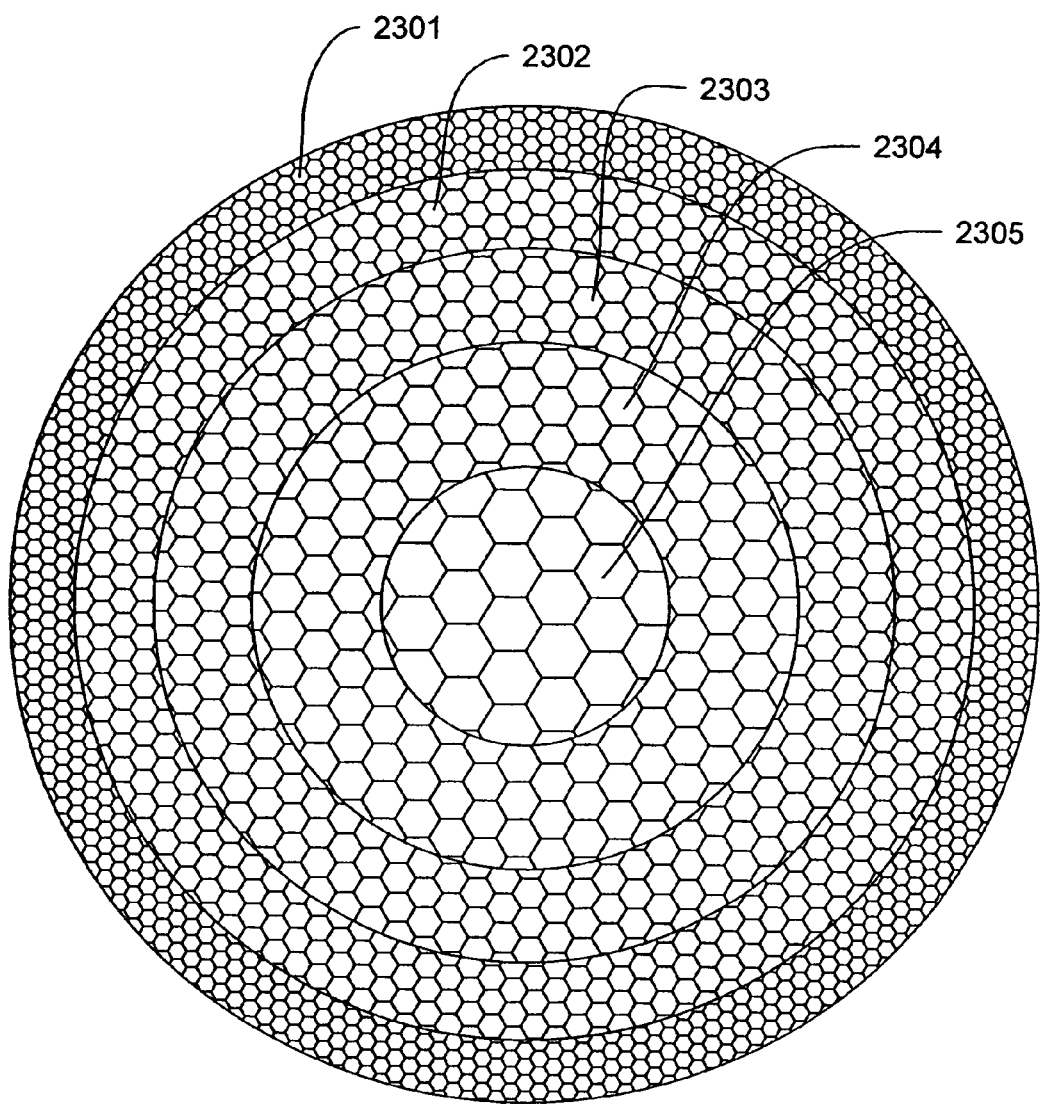

The following are embodiments that relate to a spherical geometry wherein combinations of gradient layers and/or solid metal balls are used to control the final outcomes of the constructs. FIG. 23 is an embodiment that shows a spherical construct, which utilizes five gradient layers wherein the composition of each layer is described in Tables 11 and 12:

TABLE 11

| LAYER | DIAMOND Size (μm) | DIAMOND Volume % | Cr3C2 Volume % | CoCrMo Volume % | LAYER THICKNESS (In.) |
|---|---|---|---|---|---|
| First (Outer Layer) 2301 | 20 | 92 | 8 | 0 | .090 |
| Second 2302 | 40 | 70 | 20 | 20 | .104 |
| Third 2303 | 70 | 60 | 20 | 20 | .120 |
| Forth 2304 | 70 | 60 | 26 | 26 | .138 |
| Fifth 2305 | 70 | 25 | 37.5 | 37.5 | .154 |

TABLE 12

| LAYER | DIAMOND Size (μm) | DIAMOND Volume % | Cr3C2 Volume % | CoCrMo Volume % | LAYER THICKNESS (In.) |
|---|---|---|---|---|---|
| First (Outer Layer) 2301 | 20 | 100 | 0 | 0 | .090 |
| Second 2302 | 40 | 70 | 20 | 20 | .104 |
| Third 2304 | 70 | 60 | 20 | 20 | .120 |
| Forth 2304 | 70 | 60 | 26 | 26 | .138 |
| Fifth 2305 | 70 | 25 | 37.5 | 37.5 | .154 |

Figure 24:
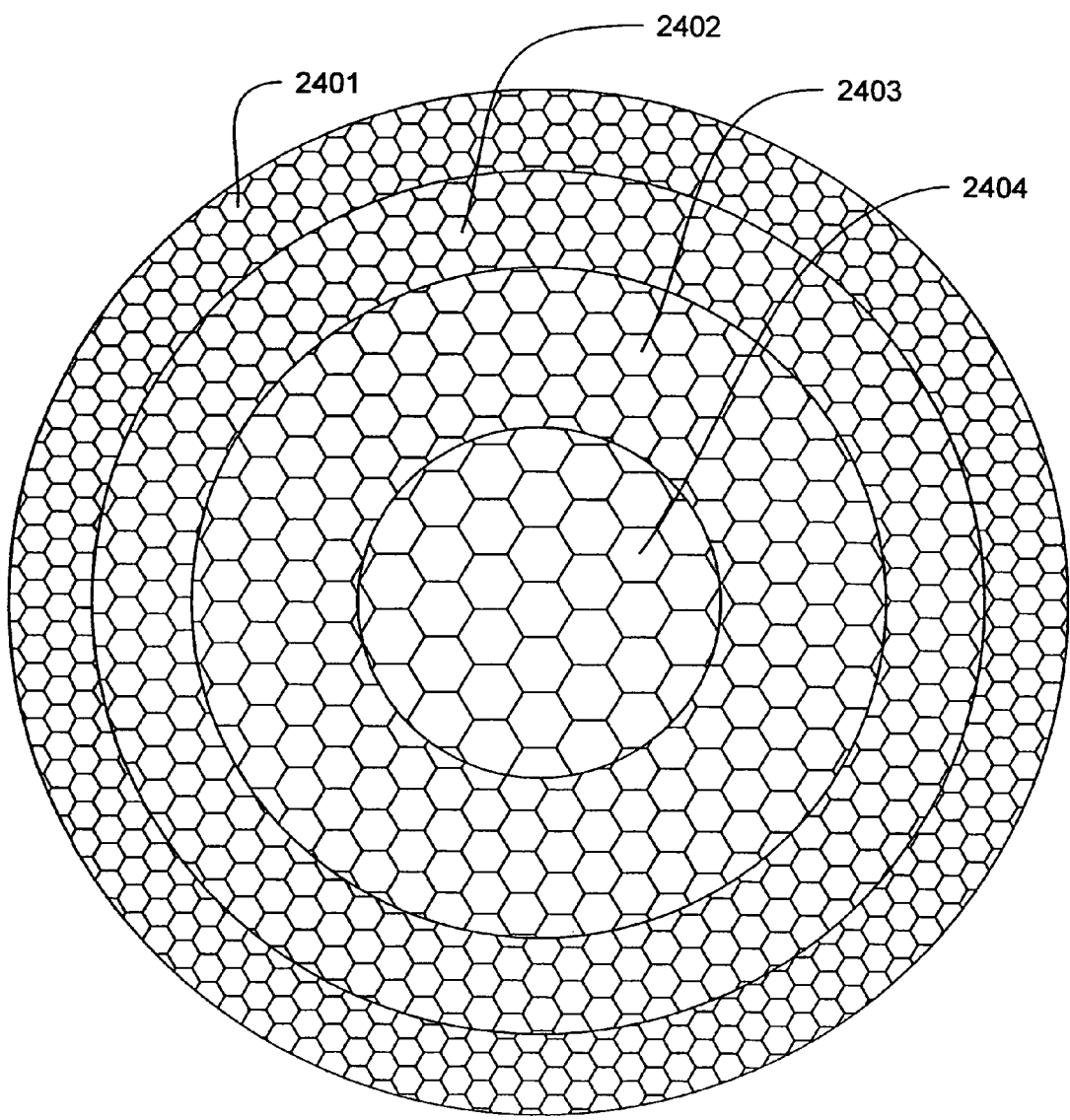

FIG. 24 is an embodiment that shows a spherical construct, which utilizes four gradient layers wherein the composition of each layer is described in Tables 13 and 14.

TABLE 13

| LAYER | DIAMOND Size (μm) | Cr3C2 Volume % | CoCrMo Volume % | LAYER Volume % | THICKNESS (In.) |
|---|---|---|---|---|---|
| First (Outer Layer) 2401 | 20 | 92 | 0 | 8 | .097 |
| Second 2402 | 40 | 70 | 10 | 20 | .125 |
| Third 2403 | 70 | 60 | 20 | 20 | .144 |
| Forth 2404 | 70 | 50 | 25 | 25 | .240 |

TABLE 14

| LAYER | DIAMOND Size (μm) | Cr3C2 Volume % | CoCrMo Volume % | LAYER Volume % | THICKNESS (In.) |
|---|---|---|---|---|---|
| First (Outer Layer) 2401 | 20 | 100 | 0 | 0 | .097 |
| Second 2402 | 40 | 70 | 10 | 20 | .125 |
| Third 2403 | 70 | 60 | 20 | 20 | .144 |
| Forth 2404 | 70 | 50 | 25 | 25 | .240 |

TABLE 15

| LAYER | DIAMOND Size (μm) | Cr3C2 Volume % | CoCrMo Volume % | LAYER Volume % | THICKNESS (In.) |
|---|---|---|---|---|---|
| First (Outer Layer) 2501 | 20 | 92 | 0 | 8 | .097 |
| Second 2502 | 40 | 70 | 10 | 20 | .125 |
| Third 2503 | 70 | 60 | 20 | 20 | .144 |
| CoCrMo Ball 2505 | N/A | N/A | N/A | N/A | N/A |

TABLE 16

| LAYER | DIAMOND Size (μm) | Cr3C2 Volume % | CoCrMo Volume % | LAYER Volume % | THICKNESS (In.) |
|---|---|---|---|---|---|
| First (Outer Layer) 2501 | 20 | 100 | 0 | 0 | .097 |
| Second 2502 | 40 | 70 | 10 | 20 | .125 |
| Third 2503 | 70 | 60 | 20 | 20 | .144 |
| CoCrMo Ball 2505 | N/A | N/A | N/A | N/A | N/A |

Figure 25:
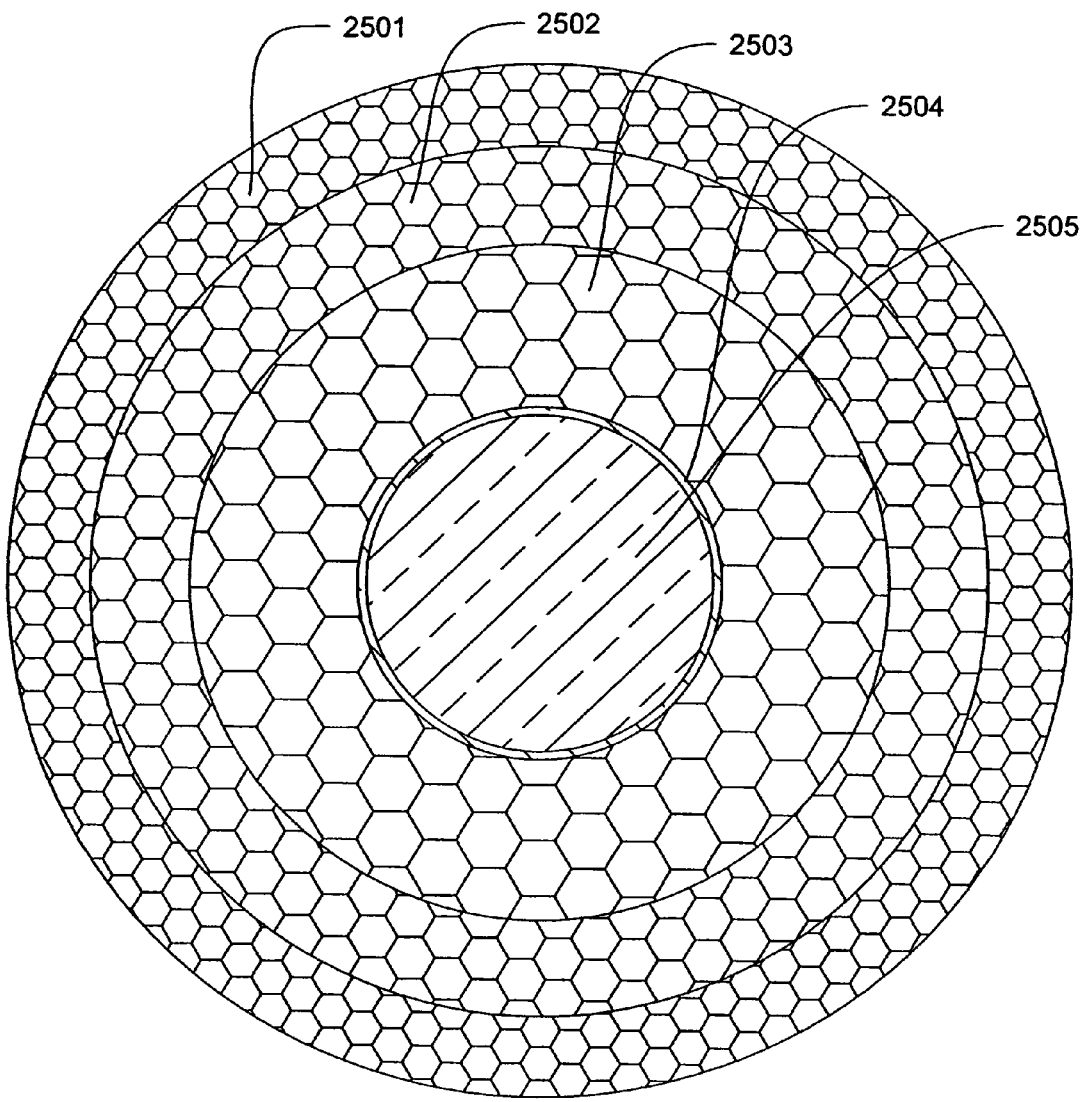

FIG. 25 shows an embodiment construct that utilizes a center support ball with gradient layers laid up on the ball and each other to form the complete construct. The inner ball of solid metal CoCrMo is encapsulated with a 0.003 to 0.010 inch thick refractory barrier can 2504 to prevent the over saturation of the system with the ball metal during the HTHP phase of sintering. The composition of each layer is described in Tables 15 and 16.

Predicated on the end use function of the sphere above, the inner ball may be made of cemented tungsten carbide, niobium, nickel, stainless steel, steel, or one of several other metal or ceramic materials to suit the designers needs.

Figure 26:
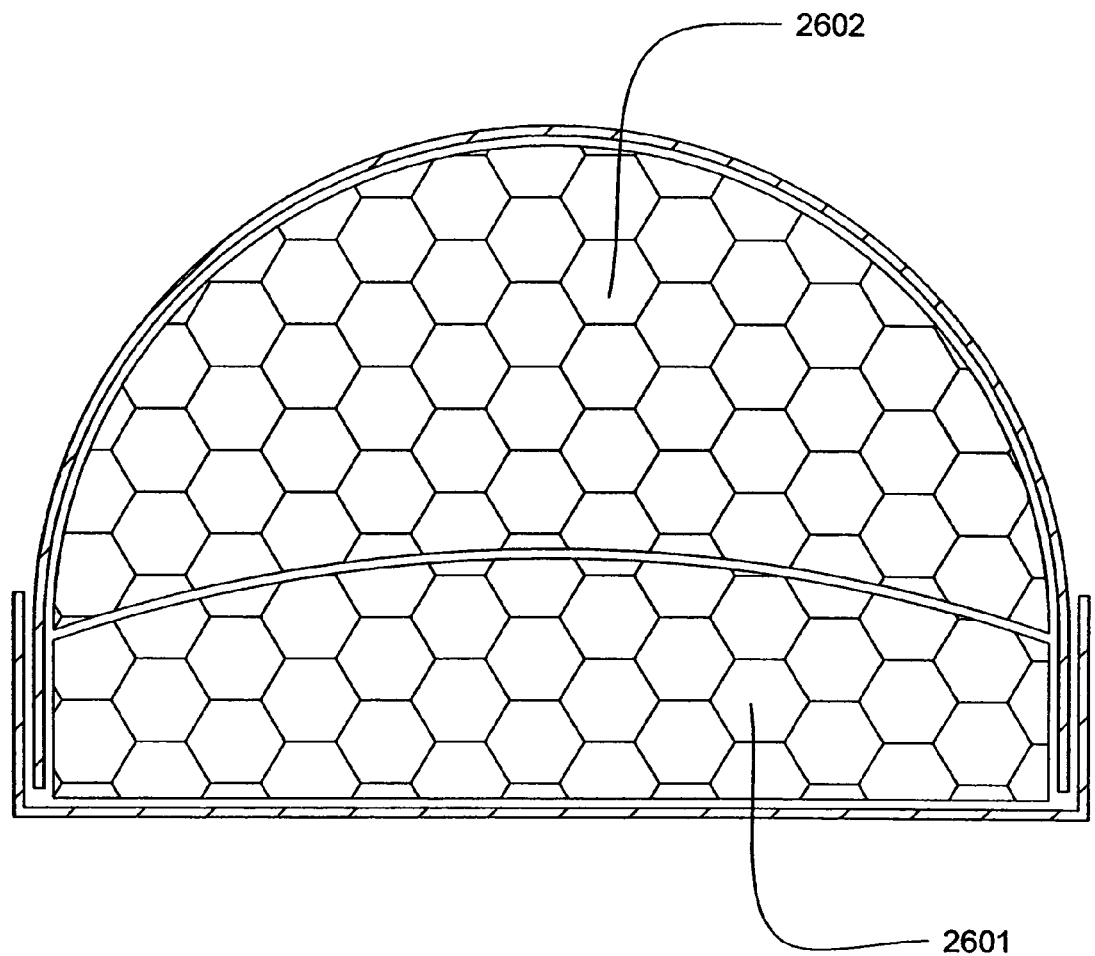

Embodiments relating to dome shapes are described as follow:

FIG. 26 shows a dome embodiment construct that utilizes two gradient layers 2601 and 2602 wherein the composition of each layer is described in Tables 17 and 18.

TABLE 17

| LAYER | DIAMOND Size (μm) | Cr3C2 Volume % | CoCrMo Volume % | TiCTiN Volume % | LAYER THICKNESS (In.) |
|---|---|---|---|---|---|
| First (Outer Layer) 2602 | 20 | 94 | 0 | 6 | 0.05 .200 |
| Second 2601 | 70 | 60 | 20 | 20 | 0.05 .125 |

TABLE 18

| LAYER | DIAMOND Size (μm) | Cr3C2 Volume % | CoCrMo Volume % | TiCTiN Volume % | LAYER THICKNESS (In.) |
|---|---|---|---|---|---|
| First (Outer Layer) 2602 | 20 | 100 | 0 | 0 | 0.05 .200 |
| Second 2601 | 70 | 60 | 20 | 20 | 0.05 .125 |

Figure 27:
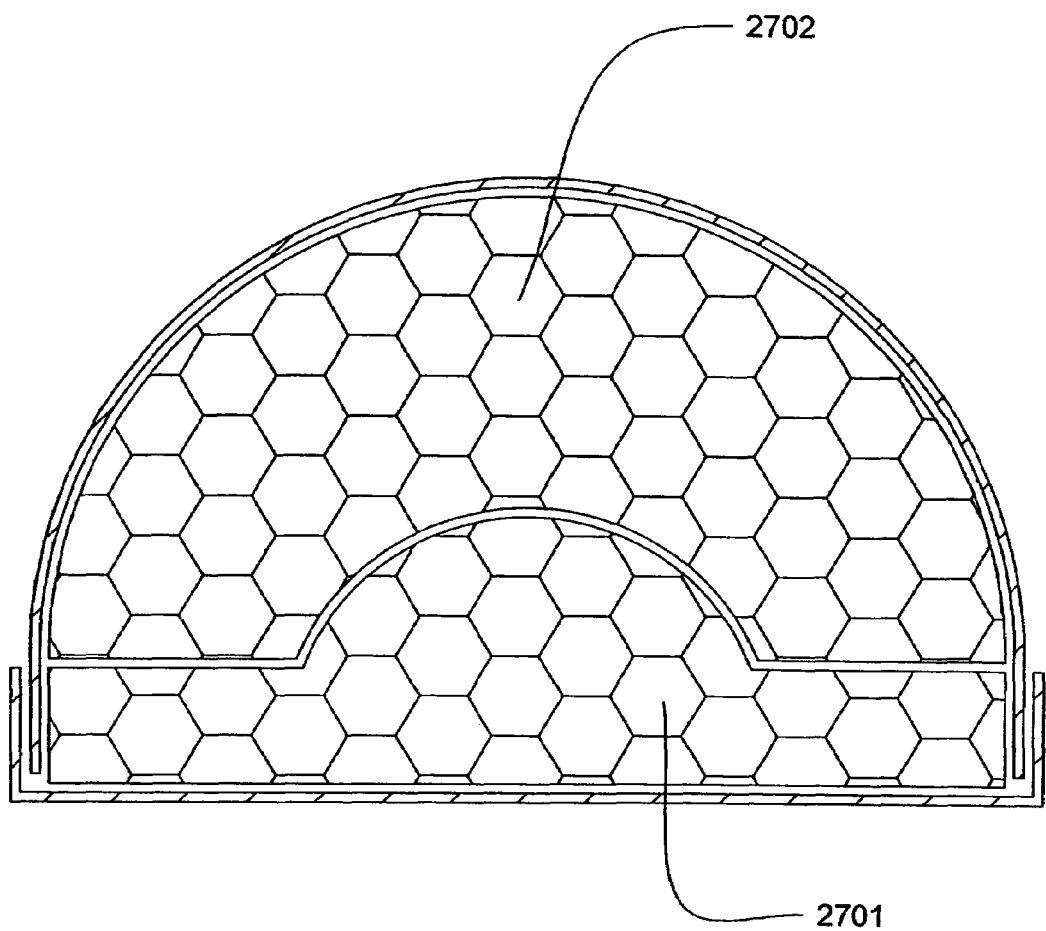

FIG. 27 shows a dome embodiment construct that utilizes two gradient layers 2701 and 2702 wherein the composition of each layer is described in Tables 19 and 20:

TABLE 19

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 2702 | 20 | 94 | 0 | 6 | 0.05 | .128 |
| Second 2701 | 70 | 60 | 20 | 20 | 0.05 | .230 |

TABLE 20

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 2702 | 20 | 100 | 0 | 0 | 0.05 | .128 |
| Second 2701 | 70 | 60 | 20 | 20 | 0.05 | .230 |

Figure 28:
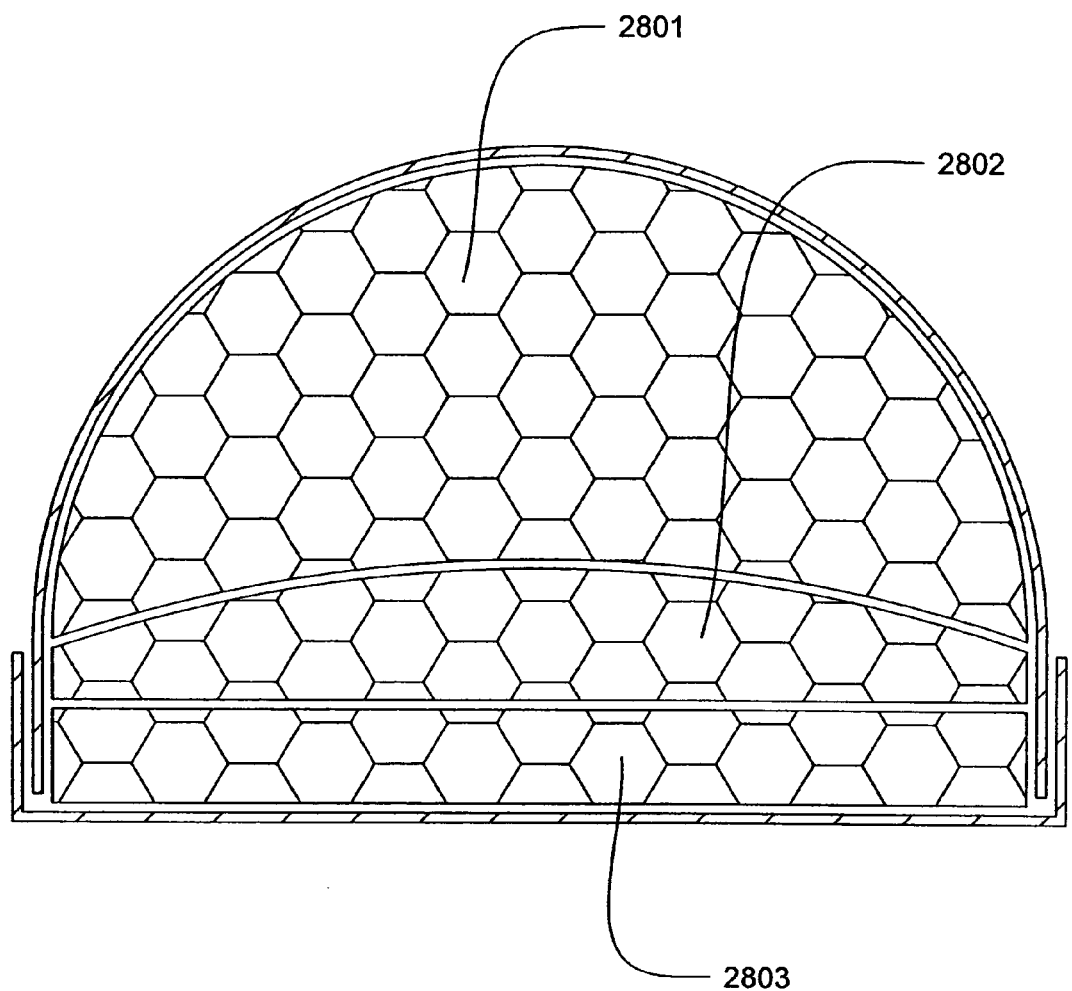

FIG. 28 shows a dome embodiment construct that utilizes three gradient layers 2801, 2802 and 2803 where the composition of each layer is described in Tables 21 and 22:

TABLE 21

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 2801 | 20 | 96 | 0 | 4 | 0.05 | .168 |
| Second 2802 | 40 | 80 | 10 | 10 | 0.05 | .060 |
| Third 2803 | 70 | 60 | 20 | 20 | 0.05 | .130 |

TABLE 22

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 2801 | 20 | 100 | 0 | 0 | 0.05 | .168 |
| Second 2802 | 40 | 80 | 10 | 10 | 0.05 | .060 |
| Third 2803 | 70 | 60 | 20 | 20 | 0.05 | .130 |

Figure 29:
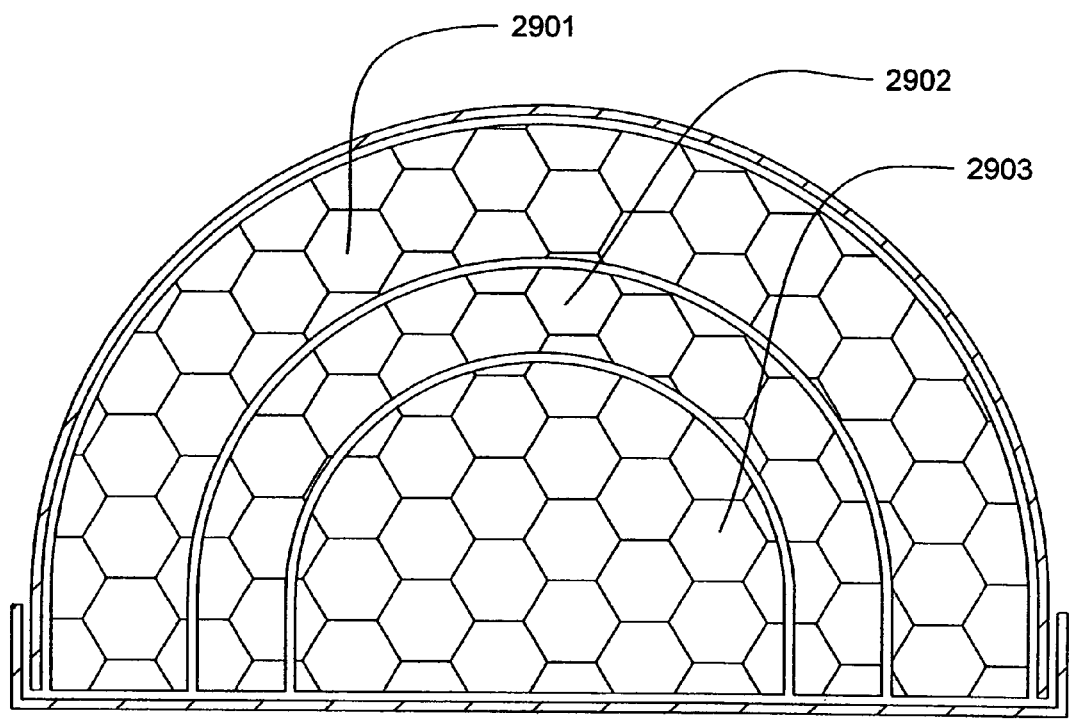

FIG. 29 shows a dome embodiment construct that utilizes three gradient layers 2901, 2902 and 9803 wherein the composition of each layer is described in Tables 23 and 24.

TABLE 23

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 2901 | 20 | 96 | 0 | 4 | 0.05 | .065 |
| Second 2902 | 40 | 80 | 10 | 10 | 0.05 | .050 |
| Third 2903 | 70 | 60 | 20 | 20 | 0.05 | .243 |

TABLE 24

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 2901 | 20 | 100 | 0 | 0 | 0.05 | .065 |
| Second 2902 | 40 | 80 | 10 | 10 | 0.05 | .050 |
| Third 2903 | 70 | 60 | 20 | 20 | 0.05 | .243 |

Figure 30:
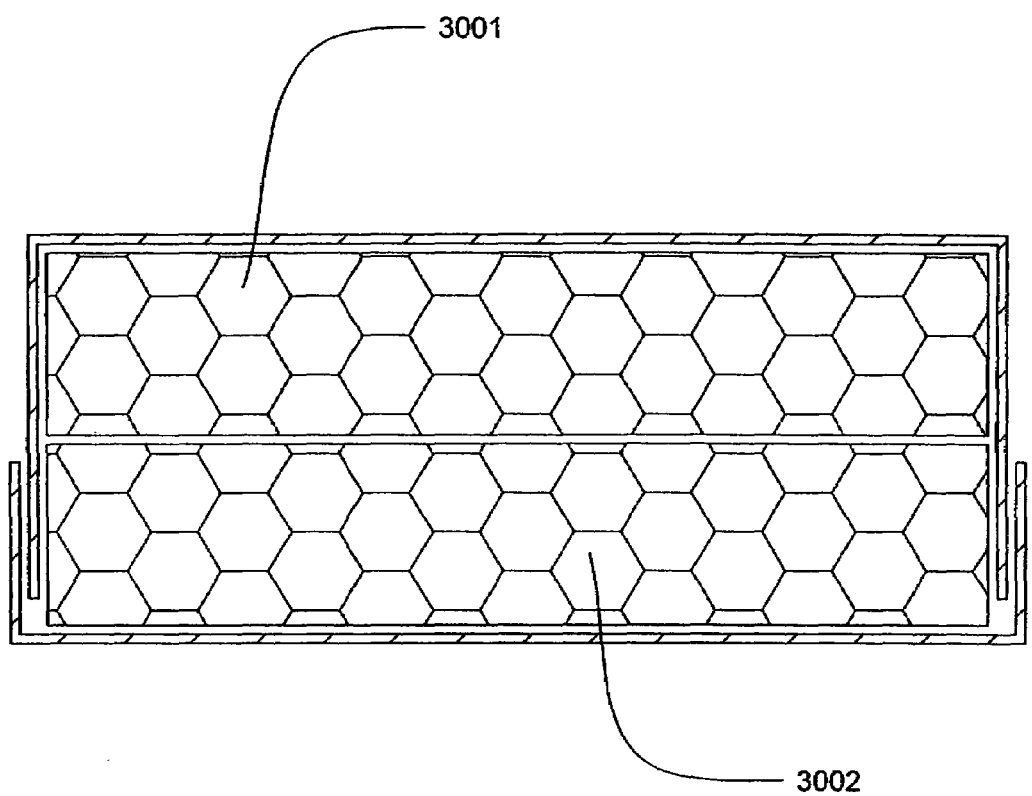

Embodiments relating to Flat Cylindrical shapes are described as follows:

FIG. 30 shows a flat cylindrical embodiment construct that utilizes two gradient layers 3001 and 3002 wherein the composition of each layer is described in Tables 25 and 26.

TABLE 25

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 3001 | 20 | 94 | 0 | 6 | 0.05 | |
| Second 3002 | 70 | 60 | 20 | 20 | 0.05 | |

TABLE 26

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 3001 | 20 | 100 | 0 | 0 | 0.05 | |
| Second 3002 | 70 | 60 | 20 | 20 | 0.05 | |

Figure 31:
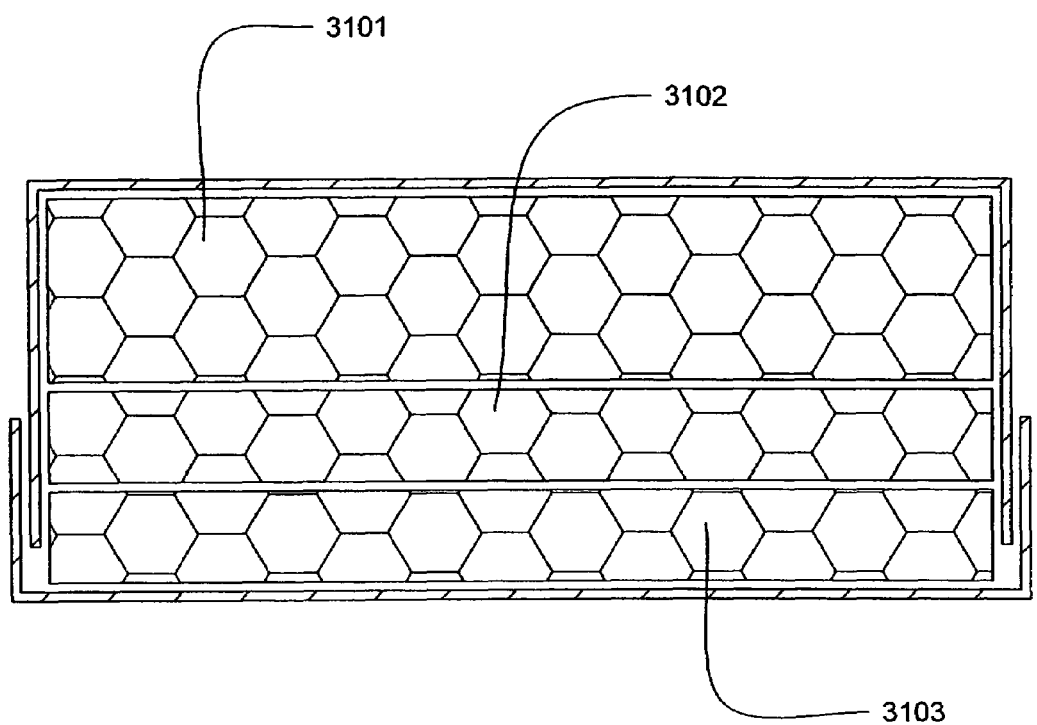

FIG. 31 shows a flat cylindrical embodiment construct that utilizes three gradient layers 3101, 3102, 3103 wherein the composition of each layer is described in Tables 27 and 28:

TABLE 27

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 3101 | 20 | 96 | 0 | 4 | 0.05 | |
| Second 3102 | 40 | 80 | 10 | 10 | 0.05 | |
| Third 3103 | 70 | 60 | 20 | 20 | 0.05 | |

TABLE 28

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 3101 | 20 | 100 | 0 | 0 | 0.05 | |
| Second 3102 | 40 | 80 | 10 | 10 | 0.05 | |
| Third 3103 | 70 | 60 | 20 | 20 | 0.05 | |

Figure 32:
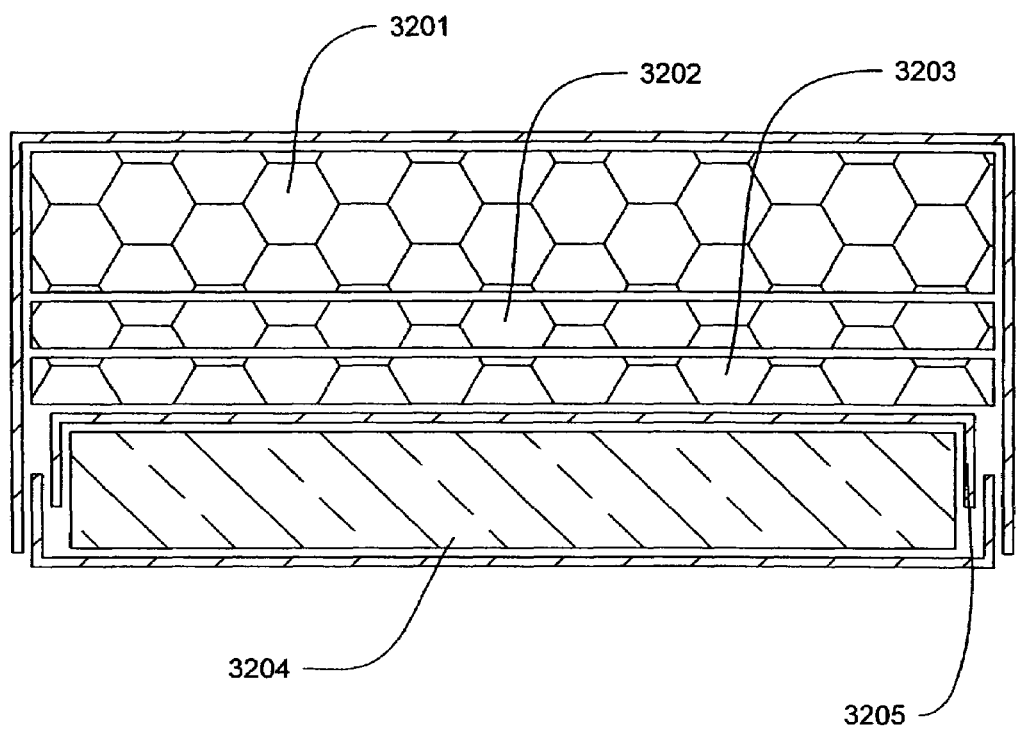

FIG. 32 shows a flat cylindrical embodiment construct that utilizes three gradient layers 3201, 3202, 3203 laid up on a CoCrMo substrate 3204. The cylindrical substrate of solid metal CoCrMo 3204 is encapsulated with a 0.003 to 0.010 inch thick refractory barrier can 3205 to prevent the over saturation of the system with the substrate metal during the HTHP phase of sintering. The composition of each layer is described in Tables 29 and 30:

TABLE 29

| LAYER | DIAMOND Size (μm) | Cr3C2 Volume % | CoCrMo Volume % | TiCTiN Volume % | LAYER THICKNESS (In.) |
|---|---|---|---|---|---|
| | Volume % | | | | |
| First (Outer Layer) 3201 | 20 | 96 | 0 | 4 | 0.05 |
| Second 3202 | 40 | 80 | 10 | 10 | 0.05 |
| Third 3203 | 70 | 60 | 20 | 20 | 0.05 |
| CoCrMo Substrate 3204 | N/A | N/A | N/A | N/A | N/A |

TABLE 30

| LAYER | DIAMOND Size (μm) | Cr3C2 Volume % | CoCrMo Volume % | TiCTiN Volume % | LAYER THICKNESS (In.) |
|---|---|---|---|---|---|
| | Volume % | | | | |
| First (Outer Layer) 3201 | 20 | 100 | 0 | 0 | 0.05 |
| Second 3202 | 40 | 80 | 10 | 10 | 0.05 |
| Third 3203 | 70 | 60 | 20 | 20 | 0.05 |
| CoCrMo Substrate 3204 | N/A | N/A | N/A | N/A | N/A |

Predicated on the end use function of the cylinder shape of FIG. 32 the inner substrate could be made of cemented tungsten carbide, niobium, nickel, stainless steel, steel, or one of several other metal or ceramic materials to suite the designers needs.

Figure 33:
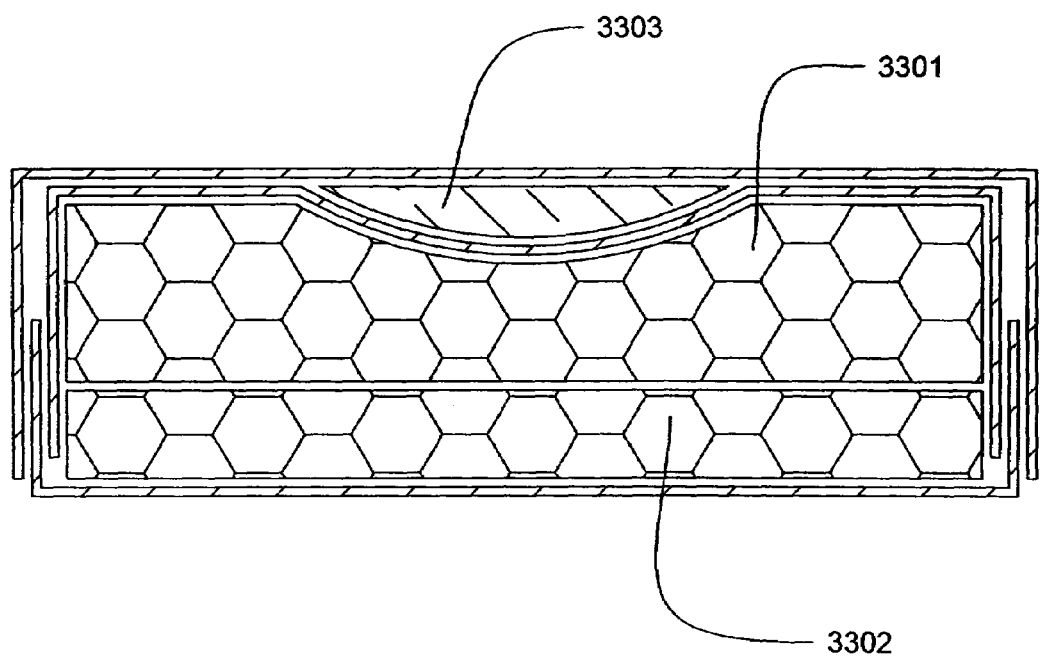

Embodiments relating to flat cylindrical shapes with formed-in-place concave features are described as follow:

FIG. 33 shows an embodiment of a flat cylindrical shape with a formed in place concave trough or filler support 3303 that utilizes two gradient layers 3301 and 3302 wherein the composition of each layer is described in Tables 31 and 32:

TABLE 31

| LAYER | DIAMOND Size (μm) | Cr3C2 Volume % | CoCrMo Volume % | TiCTiN Volume % | LAYER THICK-NESS (In.) |
|---|---|---|---|---|---|
| First (Outer Layer) 3301 | 20 | 94 | 0 | 6 | 0.05 | .156 |
| Second 3302 | 70 | 60 | 20 | 20 | 0.05 | .060 |
| Filler Support 3303 | 70 | 60 | 20 | 20 | 0.05 | N/A |

TABLE 32

| LAYER | DIAMOND Size (μm) | Cr3C2 Volume % | CoCrMo Volume % | TiCTiN Volume % | LAYER THICK-NESS (In.) |
|---|---|---|---|---|---|
| First (Outer Layer) 3301 | 20 | 100 | 0 | 0 | 0.05 | .156 |
| Second 3302 | 70 | 60 | 20 | 20 | 0.05 | .060 |
| Filler Support 3303 | 70 | 60 | 20 | 20 | 0.05 | N/A |

Figure 34:
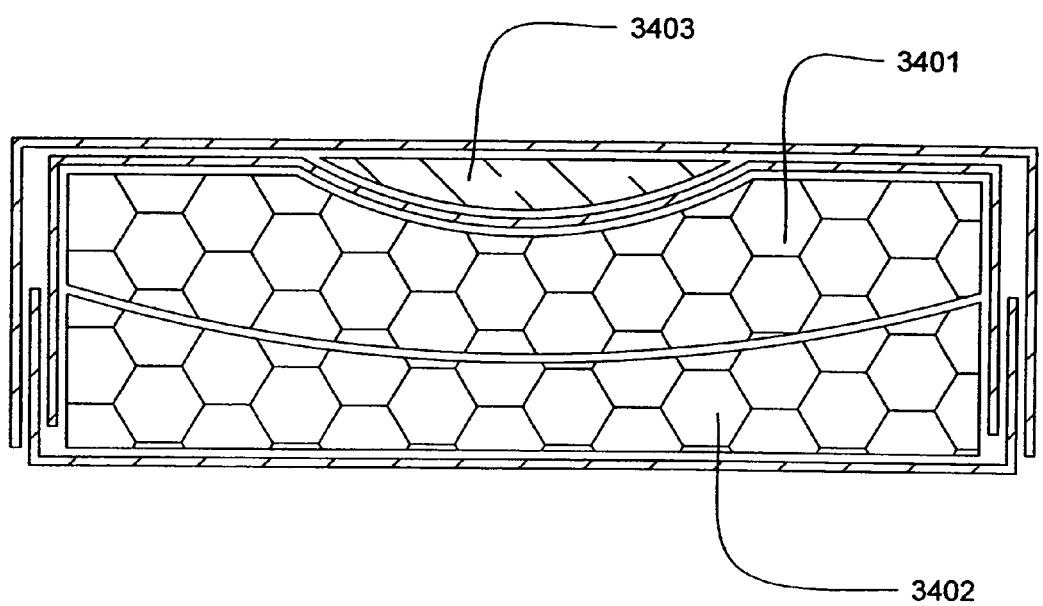

FIG. 34 shows an embodiment of a flat cylindrical shape with a formed in place concave trough or filler support 3403 that utilizes two gradient layers 3401 and 3402 wherein the composition of each layer is described in Tables 33 and 34:

TABLE 33

| LAYER | DIAMOND Size (μm) | Cr3C2 Volume % | CoCrMo Volume % | TiCTiN Volume % | LAYER THICK-NESS (In.) |
|---|---|---|---|---|---|
| First (Outer Layer) 3401 | 20 | 94 | 0 | 6 | 0.05 | .156 |
| Second 3402 | 70 | 60 | 20 | 20 | 0.05 | .060 |
| Filler Support 3403 | 70 | 60 | 20 | 20 | 0.05 | N/A |

TABLE 34

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 3401 | 20 | 100 | 0 | 0 | 0.05 | .156 |
| Second 3402 | 70 | 60 | 20 | 20 | 0.05 | .060 |
| Filler Support 3403 | 70 | 60 | 20 | 20 | 0.05 | N/A |

Figure 35:
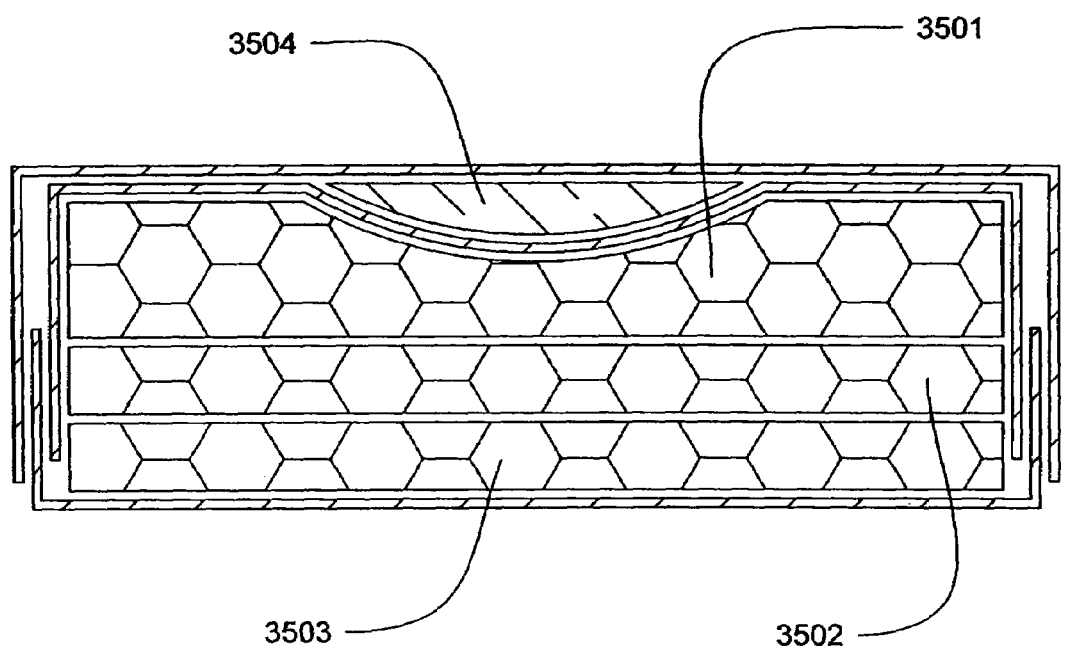

FIG. 35 shows an embodiment of a flat cylindrical shape with a formed in place concave trough or filler support 3504 that utilizes three gradient layers 3501, 3502, 3503 wherein the composition of each layer is described in Tables 35 and 36:

TABLE 35

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 3501 | 20 | 96 | 0 | 4 | 0.05 | .110 |
| Second 3502 | 40 | 80 | 10 | 10 | 0.05 | .040 |
| Third 3503 | 70 | 60 | 20 | 20 | 0.05 | .057 |
| Filler Support 3504 | 70 | 60 | 20 | 20 | 0.05 | N/A |

TABLE 36

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 3501 | 20 | 100 | 0 | 0 | 0.05 | .110 |
| Second 3502 | 40 | 80 | 10 | 10 | 0.05 | .040 |
| Third 3503 | 70 | 60 | 20 | 20 | 0.05 | .057 |
| Filler Support 3504 | 70 | 60 | 20 | 20 | 0.05 | N/A |

Figure 36:
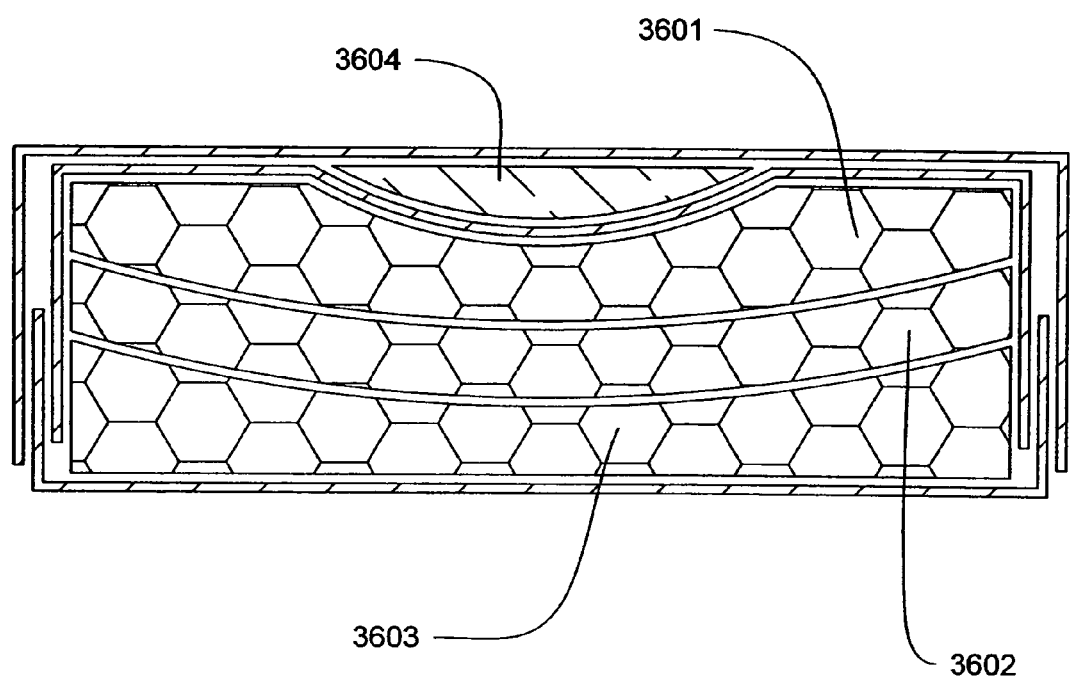

FIG. 36 shows an embodiment of a flat cylindrical shape with a formed in place concave trough or filler support 3604 that utilizes three gradient layers 3601, 3602, 3603 wherein the composition of each layer is described in Tables 37 and 38:

TABLE 37

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 3601 | 20 | 96 | 0 | 4 | 0.05 | .110 |
| Second 3602 | 40 | 80 | 10 | 10 | 0.05 | .040 |
| Third 3603 | 70 | 60 | 20 | 20 | 0.05 | .057 |
| Filler Support 3604 | 70 | 60 | 20 | 20 | 0.05 | N/A |

TABLE 38

| LAYER | DIAMOND Size (μm) | DIAMOND Volume % | Cr3C2 Volume % | CoCrMo Volume % | TiCTiN Volume % | LAYER THICKNESS (In.) |
|---|---|---|---|---|---|---|
| First (Outer Layer) 3601 | 20 | 100 | 0 | 0 | 0.05 | .110 |
| Second 3602 | 40 | 80 | 10 | 10 | 0.05 | .040 |
| Third 3603 | 70 | 60 | 20 | 20 | 0.05 | .057 |
| Filler Support 3604 | 70 | 60 | 20 | 20 | 0.05 | N/A |

Prepare Heater Assembly

In order to sinter the assembled and loaded diamond feedstock described above into PCD, both heat and pressure are required. Heat is provided electrically as the part undergoes pressure in a press. A heater assembly is used to provide the required heat.

A refractory metal can containing loaded and precompressed diamond feedstock is placed into a heater assembly. Salt domes are used to encase the can. The salt domes used may be white salt (NaCl) that is precompressed to at least about 90-95% of theoretical density. This density of the salt is desired to preserve high pressures of the sintering system and to maintain geometrical stability of the manufactured part. The salt domes and can are placed into a graphite heater tube assembly. The salt and graphite components of the heater assembly may be baked in a vacuum oven at greater than 100 degrees Celsius and at a vacuum of at least 23 torr for about 1 hour in order to eliminate absorbed water prior to loading in the heater assembly. Other materials that may be used in construction of a heater assembly include solid or foil graphite, amorphous carbon, pyrolitic carbon, refractory metals and high electrical resistant metals.

Once electrical power is supplied to the heater tube, it will generate heat required for polycrystalline diamond formation in the high pressure/high temperature pressing operation.

Preparation of Pressure Assembly for Sintering

Once a heater assembly has been prepared, it is placed into a pressure assembly for sintering in a press under high pressure and high temperature. A cubic press or a belt press may be used for this purpose, with the pressure assembly differing somewhat depending on the type of press used. The pressure assembly is intended to receive pressure from a press and transfer it to the diamond feedstock so that sintering of the diamond may occur under isostatic conditions.

If a cubic press is used, then a cube of suitable pressure transfer media such as pyrophillite will contain the heater assembly. Cell pressure medium may be used if sintering is to take place in a belt press. Salt may be used as a pressure transfer media between the cube and the heater assembly. Thermocouples may be used on the cube to monitor temperature during sintering. The cube with the heater assembly inside of it is considered a pressure assembly, and is place into a press a press for sintering.

Sintering of Feedstock into PCD

The pressure assembly described above containing a refractory metal can that has diamond feedstock loaded and precompressed within is placed into an appropriate press. An appropriate press is used to create high temperature and high pressure conditions for sintering.

To prepare for sintering, the entire pressure assembly is loaded into a cubic press and initially pressurized to about 40-68 Kbars. The pressure to be used depends on the product to be manufactured and must be determined empirically. Then electrical power is added to the pressure assembly in order to reach a temperature in the range of less than about 1145 or 1200 to more than about 1500 degrees Celsius. About 5800 watts of electrical power is available at two opposing anvil faces, creating the current flow required for the heater assembly to generate the desired level of heat. Once the desired temperature is reached, the pressure assembly is subjected to pressure of about 1 million pounds per square inch at the anvil face. The components of the pressure assembly transmit pressure to the diamond feedstock. These conditions are maintained for about 3-12 minutes, but could be from less than 1 minute to more than 30 minutes. The sintering of PDCs takes place in an isostatic environment where the pressure transfer components are permitted only to change in volume but are not permitted to otherwise deform. Once the sintering cycle is complete, about a 90 second cool down period is allowed, and then pressure is removed. The PDC is then removed for finishing.

Removal of a sintered PDC having a curved, compound or complex shape from a pressure assembly is simple due to the differences in material properties between diamond and the surrounding metals in some embodiments. This is generally referred to as the mold release system.

Removal of Solvent-Catalyst Metal from PCD

If desired, the solvent-catalyst metal remaining in interstitial spaces of the sintered PCD may be removed. Such removal is accomplished by chemical leaching as is known in the synthetic diamond field. After solvent-catalyst metal has been removed from the interstitial spaces in the diamond table, the diamond table will have greater stability at high temperatures. This is because there is no catalyst for the diamond to react with and break down.

After leaching solvent-catalyst metal from the diamond table, it may be replaced by another metal or metal compound to form thermally stable diamond that is stronger than leached PCD. If it is intended to weld synthetic diamond or a PDC to a substrate or to another surface such as by inertia welding, it may be desirable to use thermally stable diamond due to its resistance to heat generated by the welding process.

Manufacture of Concave Surfaces

An example substrate geometry for manufacturing a concave spherical, hemispherical or partially spherical polycrystalline diamond compact can be understood in conjunction with review of FIGS. 37A-37C. The substrate 601 (and 601a and 601b) may be in the form of a cylinder with a hemispherical receptacle 602 (and 602a and 602b) formed into one of its ends. Two substrate cylinders 601a and 601b are placed so that their hemispherical receptacles 602a and 602b are adjacent each other, thus forming a spherical cavity 604 between them. A sphere 603 of an appropriate substrate material is located in the cavity 604. Diamond feedstock 605 is located in the cavity 604 between the exterior of the sphere 603 and the concave surfaces of the receptacles 602a and 602b of the substrate cylinders 601a and 601b. The assembly is placed into a refractory metal can 610 for sintering. The can has a first cylinder 610a and a second cylinder 601b. The two cylinders join at a lip 611. After such an assembly is sintered, the assembly may be slit, cut or ground along the center line 606 in order to form a first cup assembly 607a and a second cup assembly 607b. Example substrate materials for the cylinders 602a and 602b are CoCrMo (ASTM F-799) and CoCrW (ASTM F-90), and an example substrate material for the sphere 603 is CoCrMo (ASTM F-799), although any appropriate substrate material may be used, including some of those listed elsewhere herein.

Manufacture of Convex Surfaces

Figure 13A:
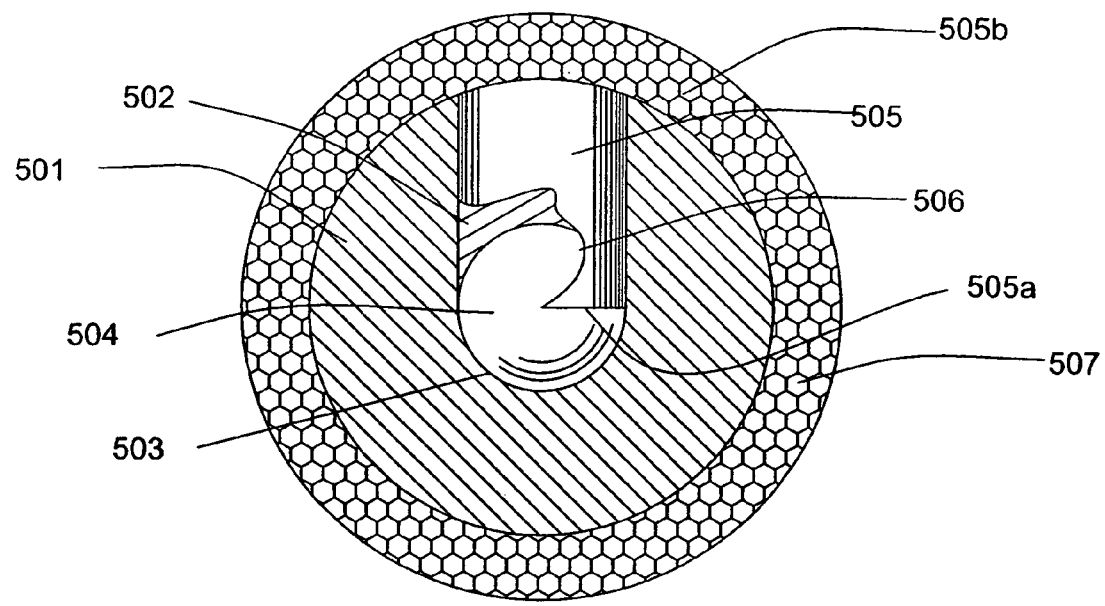
FIGS. 13A-13G depict some substrate and superhard material configurations.
Figure 13B:
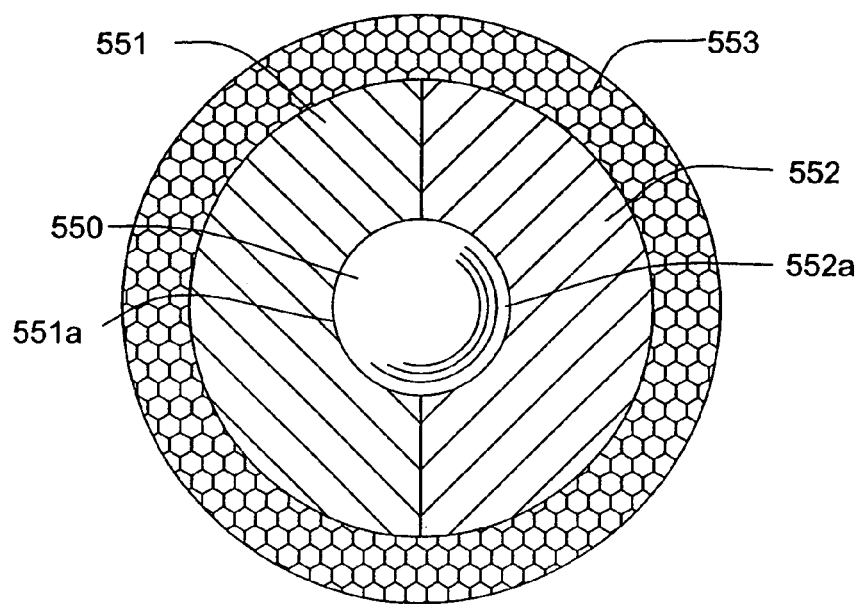

In this section, examples for manufactureing various convex superhard surfaces are provided. Referring to FIGS. 13A-13F, various substrate structures of the invention for making a generally spherical polycrystalline diamond or polycrystalline cubic boron nitride compact are depicted. FIGS. 13A and 13B depict two-layer substrates.

In FIG. 13A, a solid first sphere 501 of a substrate material intended to be used as the substrate shell or outer layer was obtained. The dimensions of the first sphere 501 are such that the dimension of the first sphere 501 with a diamond table on its exterior will approximate the intended dimension of the component prior to final finishing. Once the first sphere 501 of the substrate is obtained, a hole 502 is bored into its center. The hole 502 is preferably bored, drilled, cut, blasted or otherwise formed so that the terminus 503 of the hole 502 is hemispherical. This may be achieved by using a drill bit or end mill with a round or ball end having the desired radius and curvature. Then a second sphere 504 of a substrate material is obtained. The second sphere 504 is smaller than the first sphere 501 and is be placed in hole 502 in the first sphere 501. The substrates materials of spheres 501 and 504 may be selected form those listed in the tables above. They may also be of other appropriate materials. The second sphere 504 and the hole 502 and its terminus 503 should fit together closely without excessive tolerance or gap. A plug 505 which may be of the same substrate material as first sphere 501 is formed or obtained. The plug 505 has a first end 505a and a second end 505b and substrate material therebetween in order to fill the hole 502 except for that portion of the hole 502 occupied by the second sphere 504 adjacent the hole terminus 503. The plug 505 may have a concave hemispherical receptacle 506 at its first end 505a so that plug 505 will closely abut second sphere 504 across about half the spherical surface of second sphere 504. The plug 505 may be generally cylindrical in shape. The substrate assembly including one substrate sphere placed inside of another may then be loaded with diamond feedstock 507 or cubic boron nitride feedstock and sintered under high pressure at high temperature to form a spherical polycrystalline diamond compact.

Referring to FIG. 13B, another substrate geometry for manufacturing spherical polycrystalline diamond or cubic boron nitride compacts is depicted. An inner core sphere 550 of appropriate substrate material is selected. Then an outer substrate first hemisphere 551 and outer substrate second hemisphere 552 are selected. Each of the outer substrate first and second hemispheres 551 and 552 are formed so that they each have a hemispherical receptacle 551a and 552a shaped and sized to accommodate placement of the hemispheres about the exterior of the inner core sphere 550 and thereby enclose and encapsulate the inner core sphere 550. The substrates materials of inner core sphere 550 and hemispheres 551 and 552 are preferably selected form those listed in the tables above or other appropriate materials. With the hemispheres and inner core sphere assembled, diamond feedstock 553 may be loaded about the exterior of the hemispheres and high temperature and high pressure sintering may proceed in order to form a spherical compact.

Although FIGS. 13A and 13B depict two-layer substrates, it is possible to use multiple layer substrates (3 or more layers) for the manufacture of polycrystalline diamond or polycrystalline diamond compacts or polycrystalline cubic boron nitride compacts. The selection of a substrate material, substrate geometry, substrate surface topographical features, and substrates having a plurality of layers (2 or more layers) of the same or different materials depend at least in part on the thermo-mechanical properties of the substrate, the baro-mechanical properties of the substrate, and the baro-mechanical properties of the substrate.

Figure 13C:
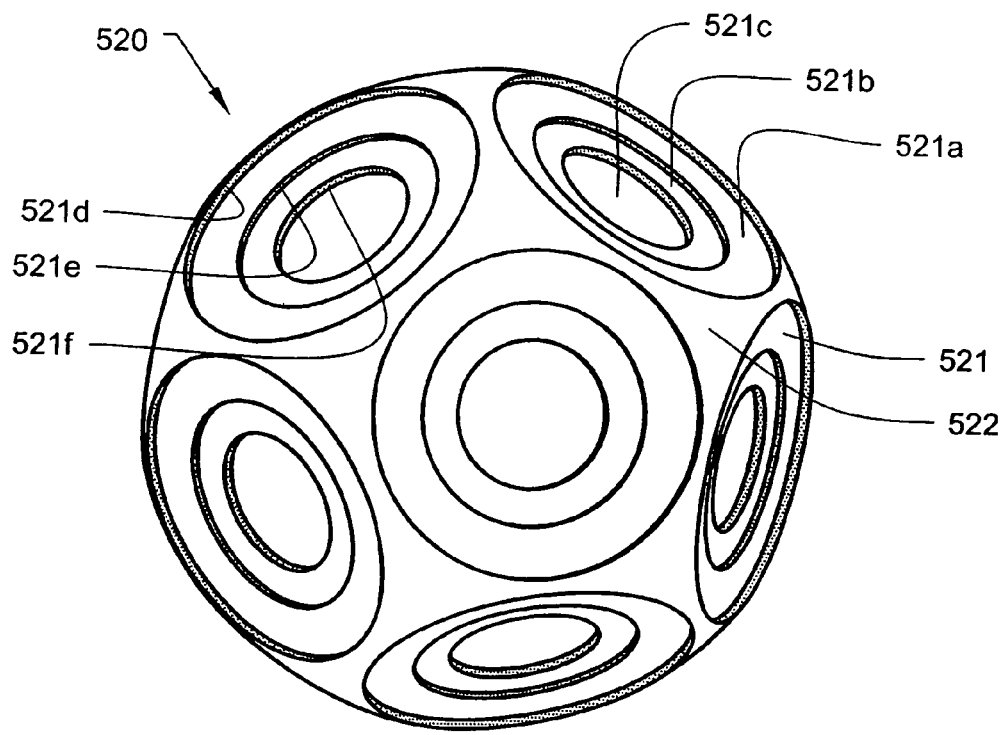

Referring to FIG. 13C, another substrate configuration for making generally spherical compacts is depicted. The substrate 520 is in the general form of a sphere. The surface of the sphere includes substrate surface topography intended to enhance fixation of a diamond table to the substrate. The substrate has a plurality of depressions 521 formed on its surface. Each depression 521 is formed as three different levels of depression 521a, 521b and 521c. The depressions are depicted as being concentric circles, each of approximately the same depth, but their depths could vary, the circles need not be concentric, and the shape of the depressions need not be circular. The depression walls 521d, 521e and 521f are depicted as being parallel to a radial axis of the depressions which axis is normal to a tangent to the theoretical spherical extremity of the sphere, but could have a different orientation if desired. As depicted, the surface of the substrate sphere 522 has no topographical features other than the depressions already mentioned, but could have protrusions, depressions or other modifications as desired. The width and depth dimensions of the depressions 521 may be varied according to the polycrystalline diamond compact that is being manufactured. Diamond feedstock may be loaded against the exterior of the substrate sphere 520 and the combination may be sintered at diamond stable pressures to produce a spherical polycrystalline diamond compact. Use of substrate surface topographical features on a generally spherical substrate provides a superior bond between the diamond table and the substrate as described above and permits a polycrystalline diamond compact to be manufactured using a single layer substrate. That is because of the gripping action between the substrate and the diamond table achieved by use of substrate surface topographical features.

Figure 13D:
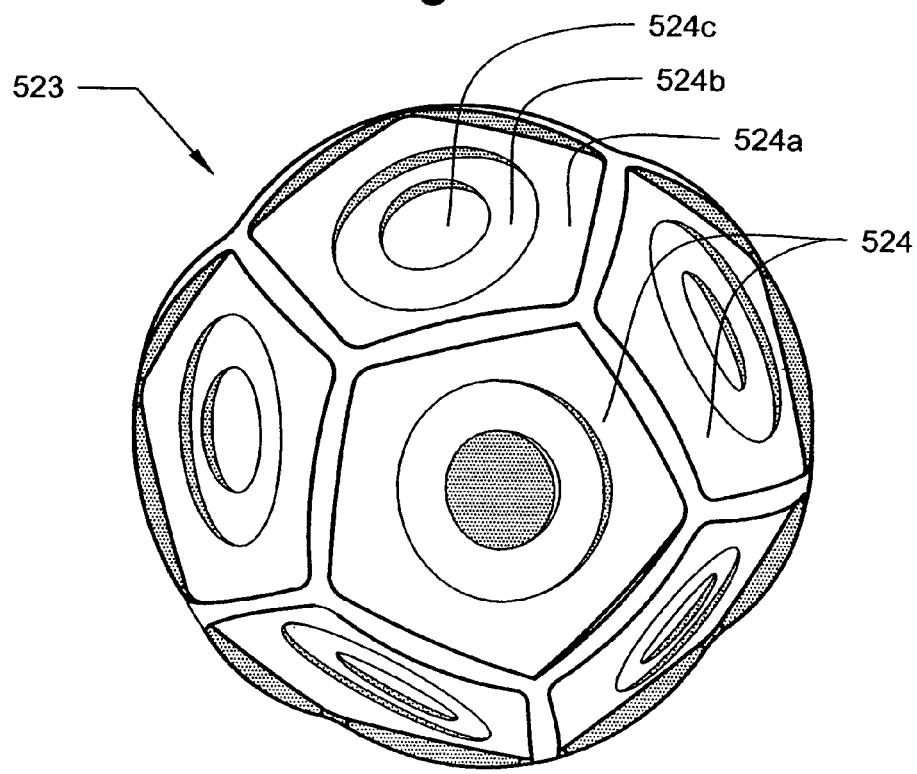

Referring to FIG. 13D, a segmented spherical substrate 523 is depicted. The substrate has a plurality of surface depressions 524 equally spaced about its exterior surface. These depressions as depicted are formed in levels of three different depths. The first level 524a is formed to a predetermined depth and is of pentagonal shape about its outer periphery. The second level 524b is round in shape and is formed to a predetermined depth which may be different from the predetermined depth of the pentagon. The third level 524c is round in shape in is formed to a predetermined depth which may be different from each of the other depths mentioned above. Alternatively, the depressions may be formed to only one depth, may all be pentagonal, or may be a mixture of shapes. The depressions may be formed by machining the substrate sphere.

Figure 13E:
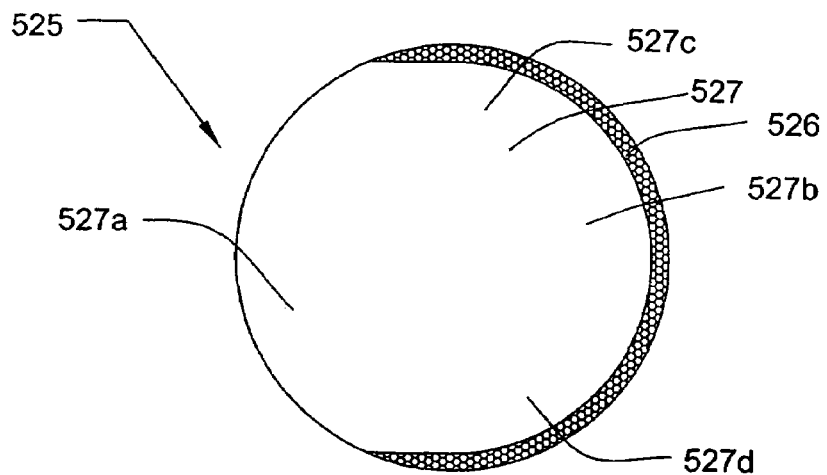

Referring to FIG. 13E, a cross section of an alternative substrate configuration for making a polycrystalline diamond or polycrystalline cubic boron nitride compact is shown. A compact 525 is shown. The compact 525 is spherical. The compact 525 includes a diamond table 526 sintered to a substrate 527. The substrate is partially spherical in shape at its distal side 527a and is dome-shaped on its proximal side 527b. Alternatively, the proximal side 527b of the substrate 527 may be described as being partially spherical, but the sphere on which it is based has a radius of smaller dimension than the radius of the sphere on which the distal side 527a of the substrate is based. Each of the top 527c and bottom 527d are formed in a shape convenient to transition from the proximal side 527b substrate partial sphere to the distal side 527a substrate partial sphere. This substrate configuration has advantages in that it leaves a portion of substrate exposed for drilling and attaching fixation components without disturbing residual stress fields of the polycrystalline diamond table. It also provides a portion of the substrate that does not have diamond sintered to it, allowing dilatation of the substrate during sintering without disruption of the diamond table. More than 180 degrees of the exterior of the substrate sphere has diamond on it, however, so the part is useful as a femoral head or other articulation surface.

Figure 13F:
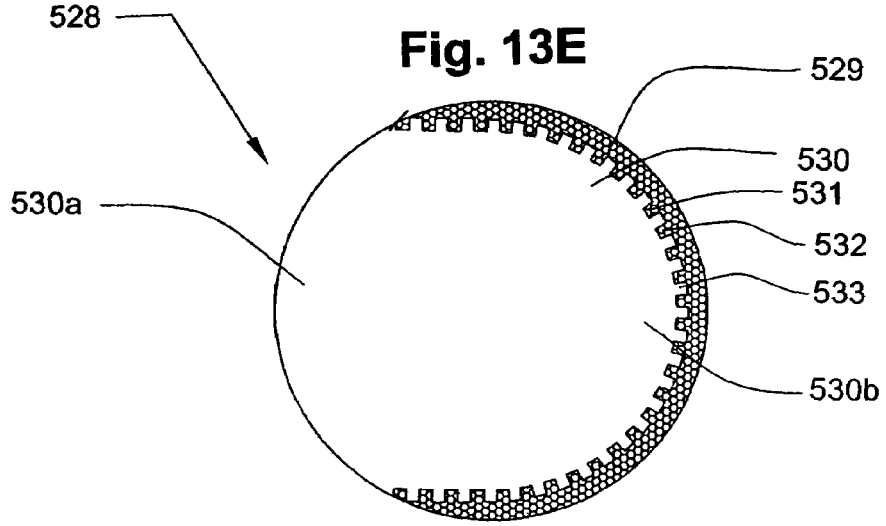

Referring to FIG. 13F, a cross section of an alternative substrate configuration for making a polycrystalline diamond compact is shown. A polycrystalline diamond compact 528 is depicted having a diamond table 529 and a substrate 530. The substrate has topographical features 531 for enhancing strength of the diamond to substrate interface. The topographical features may include rectangular protrusions 532 spaced apart by depressions 533 or corridors. The distal side of the substrate is formed based on a sphere of radius r. The proximal side of the substrate 530b is formed based on a sphere of radius r', where r>r'. Usually the surface modifications will be found beneath substantially all of the diamond table.

Figure 13G:
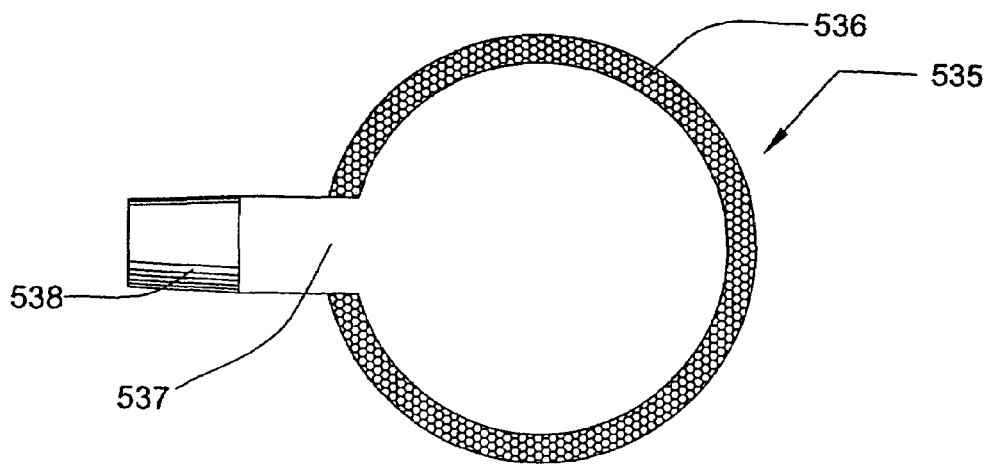

Referring to FIG. 13G, another generally spherical compact 535 is shown that includes a diamond table 536 sintered to a substrate 536. The substrate is configured as a sphere with a protruding cylindrical shape. The head 535 is formed so that a quantity of substrate protrudes from the spherical shape of the head to form a neck 538 which may be attached to an appropriate body by any known attachment method. The use of a neck 538 preformed on the substrate that is used to manufacture a polycrystalline diamond or cubic boron nitride compact 535 provides an attachment point on the polycrystalline diamond compact that may be utilized without disturbing the residual stress field of the compact. The neck 538 depicted is an integral component of a stem 540.

Any of the previously mentioned substrate configurations and substrate topographies and variations and derivatives of them may be used to manufacture a polycrystalline diamond or polycrystalline cubic boron nitrode compact for use in a variety of fields. In various embodiments, a single layer substrate may be utilized. In other embodiments, a two-layer substrate may be utilized, as discussed. Depending on the properties of the components being used, however, it may be desired to utilize a substrate that includes three, four or more layers.

Segmented and Continuous Superhard Structures

In this section, the concept of structures which use segments of hard or superhard materials is discussed. The segments (or inserts) may present a concave, convex or planar contact area, as desired, and can simplify construction of products with complex geometries. Structures with segmented superhard surfaces may be made by sintering the superhard segments in place on a substrate so that the segments of superhard material and the substrate form an integral superhard compact. Or structures with segmented superhard or hard surfaces may be made by manufacturing the superhard or hard material in advance, and then installing it in a separate substrate later by such techniques as friction fit, interference fit, mechanical interlock, brazing, welding, adhesion, etc. For comparison, superhard structures with continuous surfaces are also discussed below. Example segmented and continuous structures are now discussed.

Figure 4B:
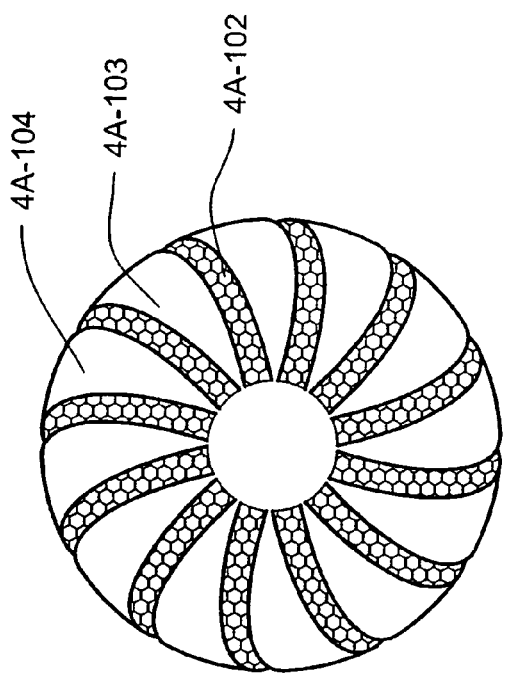
Figure 4A:
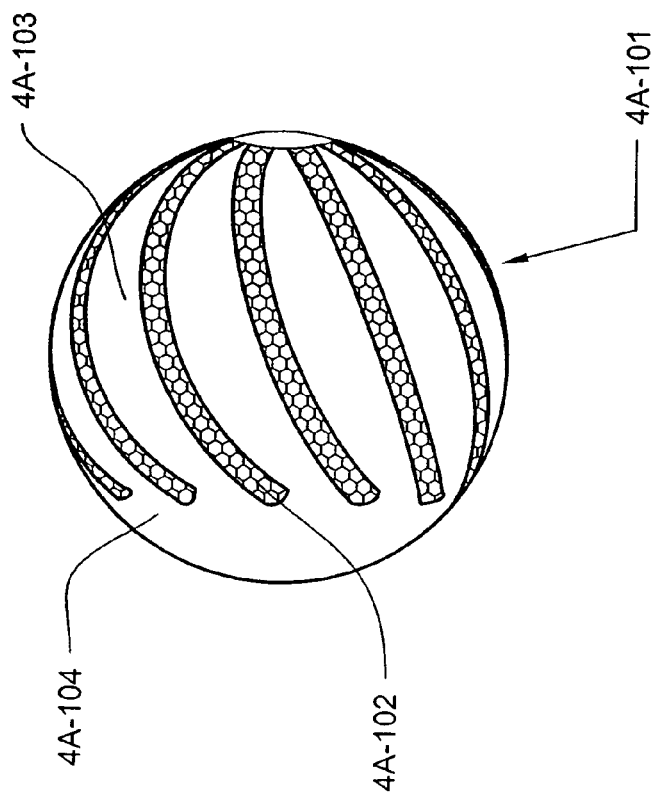

The geometry in FIGS. 4A-4B consists of veins or stripes of bearing material that start from a polar region and migrate outward with a slight angular propensity. FIG. 4A illustrates a side view of the head 4A-101. Specifically, the substrate material 4A-104 is marked by elevated ridges of diamond 4A-102 and recessed troughs 4A-103 between the diamond ridges 4A-102. FIG. 4B is a top view of FIG. 4A illustrating a pattern of arcuate ridges emanating from a central location or spherical point. A straight-line version of this pattern is also possible.

Figure 4D:
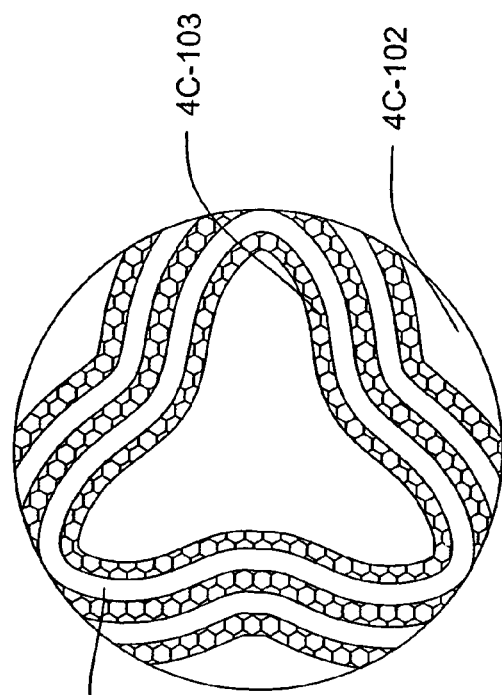
Figure 4C:
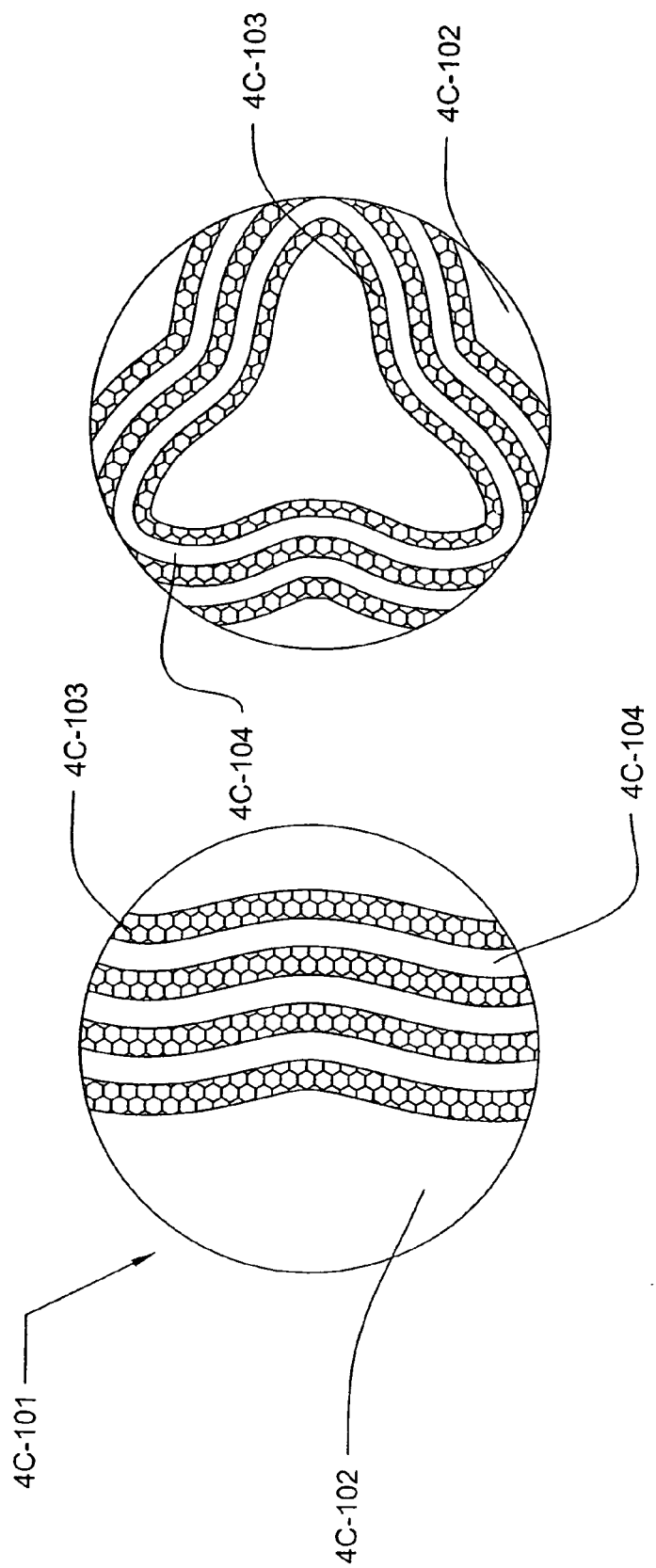

The geometry of FIGS. 4C-4D consists of undulating lines that are continuous around the surface of the sphere. FIG. 4C illustrates a side view of the head with a spherical point 4C-101 such that elevated non-linear ridges of diamond 4C-103 wrap around the substrate material 4C-102. Like FIGS. 4A and 4B, troughs 4C-104 exist between the diamond ridges 4C-103. FIG. 4D is a top view of FIG. 4C. A straight line version of this pattern is also possible.

Materials for the inserts include but are not limited to diamond, cubic boron nitride, corbonitride steels, steel, carbonitrides, borides, nitrides, silicides, carbides, ceramic matrix composites, fiber reinforced ceramic matrix composites, cast iron, carbon and alloy steels, stainless steel, roller bearing steel, tool steel, hard facing alloys, cobalt based alloys, Ni3Al alloys, surface treated titanium alloys, cemented carbides, cermets, ceramics, carbon-graphite based materials, fiber reinforced thermoplastics, metal matrix composites.

Materials for the substrate include but are not limited to corbonitride steels, steel, carbonitrides, borides, nitrides, silicides, carbides, ceramic matrix composites, fiber reinforced ceramic matrix composites, cast iron, carbon and alloy steels, stainless steel, roller bearing steel, tool steel, hard facing alloys, cobalt based alloys, Ni3Al alloys, surface treated titanium alloys, cemented carbides, cermets, ceramics, carbon-graphite based materials, fiber reinforced thermoplastics, metal matrix composites.

The substrate may be configured such as to place the insert material into a compressive state sufficient to impart structural stability to the insert material that heretofore was not present. The insert material is put into a compressive state by the use of an interference fit with the surrounding substrate material. By placing the insert material in this compressive condition the neutral stress axis in the insert material is displaced in such a fashion that the bearing material is now capable of sustaining higher loading while maintaining its structural integrity in combination with its superior wear properties. This allows for the use of materials that have very desirable wear properties but insufficient structural capacity to now be configured in such a manner as to make them candidates for wear bearings that heretofore not available for use. The substrate material may be machined or cast with the desired geometry for the bearing material. The substrate material is then heated to a pre-determined temperature and the wear bearing inserts are cooled to a pre-determined temperature and then the wear bearing insert is pressed into the substrate. The difference in size of the materials results in the wear bearing material being in a compressive state.

Figures 1, 4E:
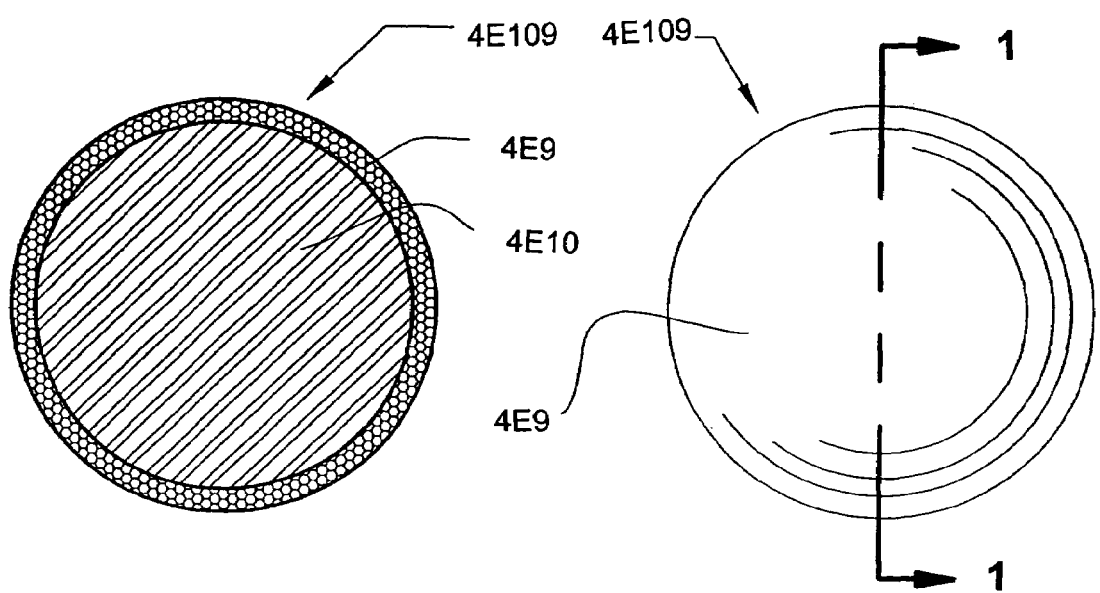
Figure 5:
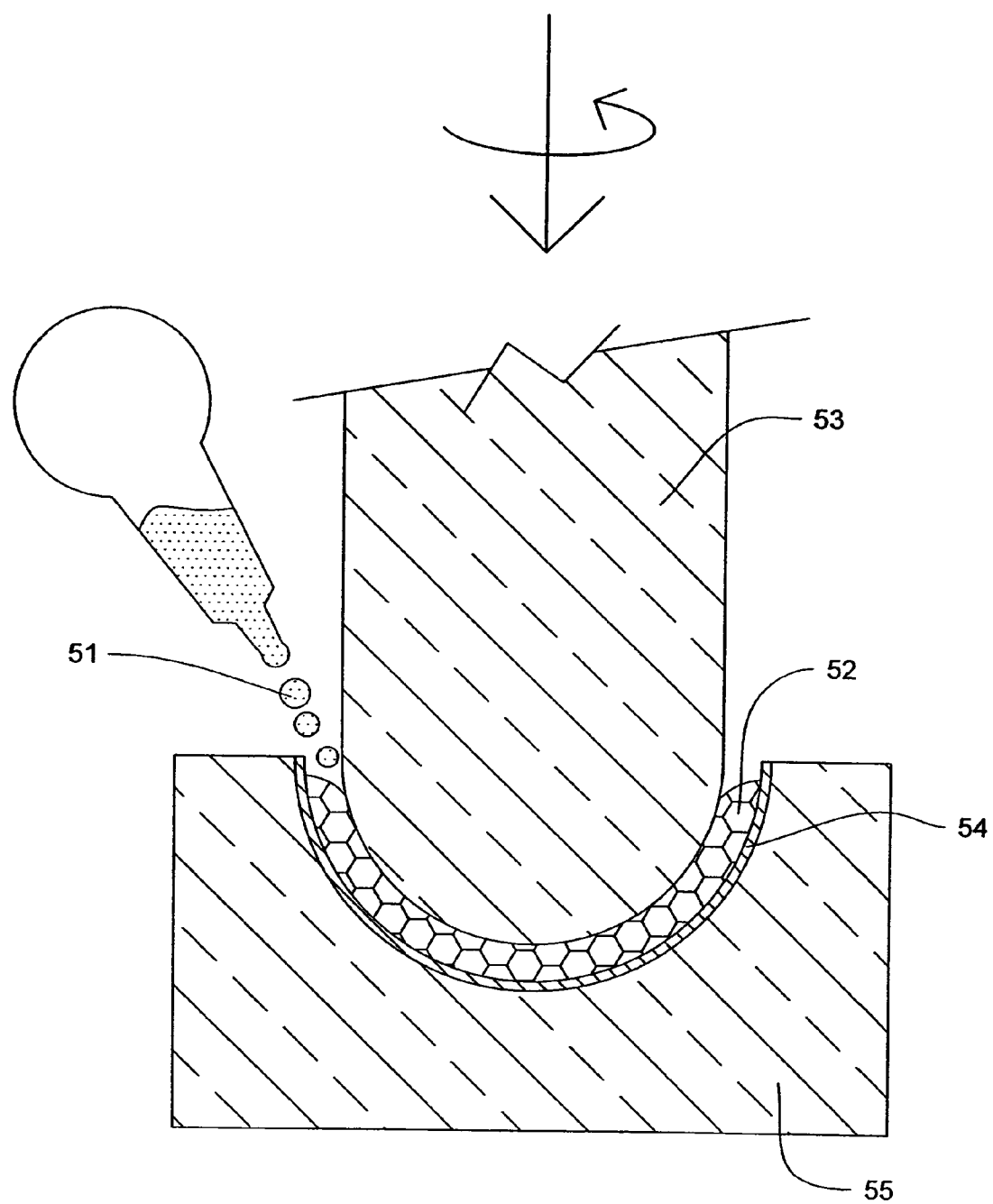
Figure 6:
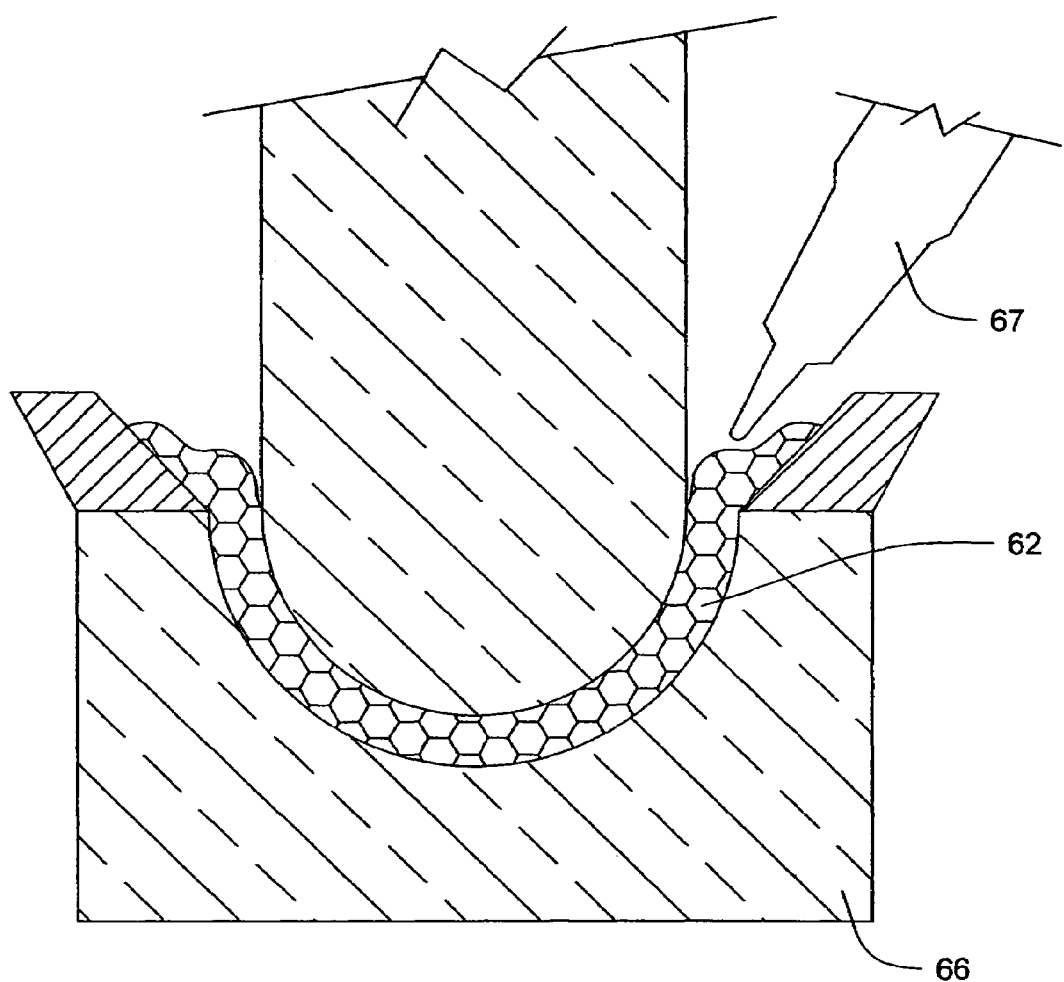
Figure 7:
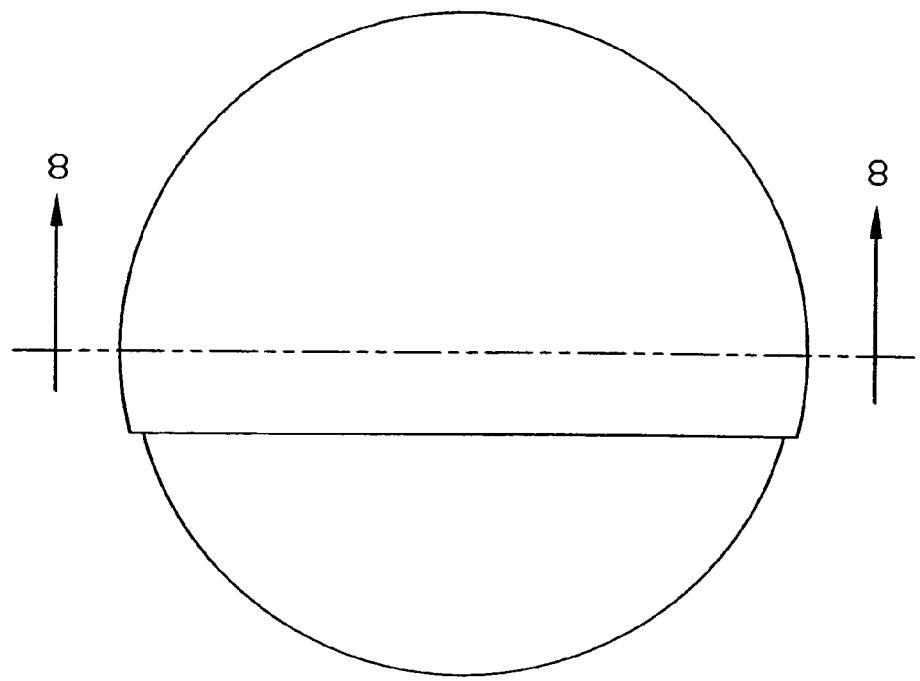
Figure 8:
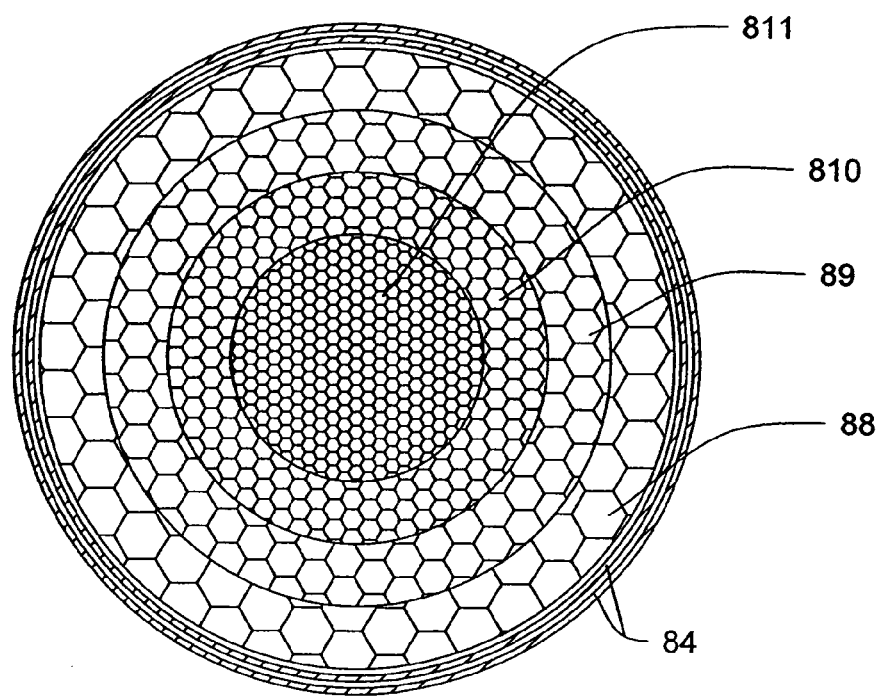
Figure 9:
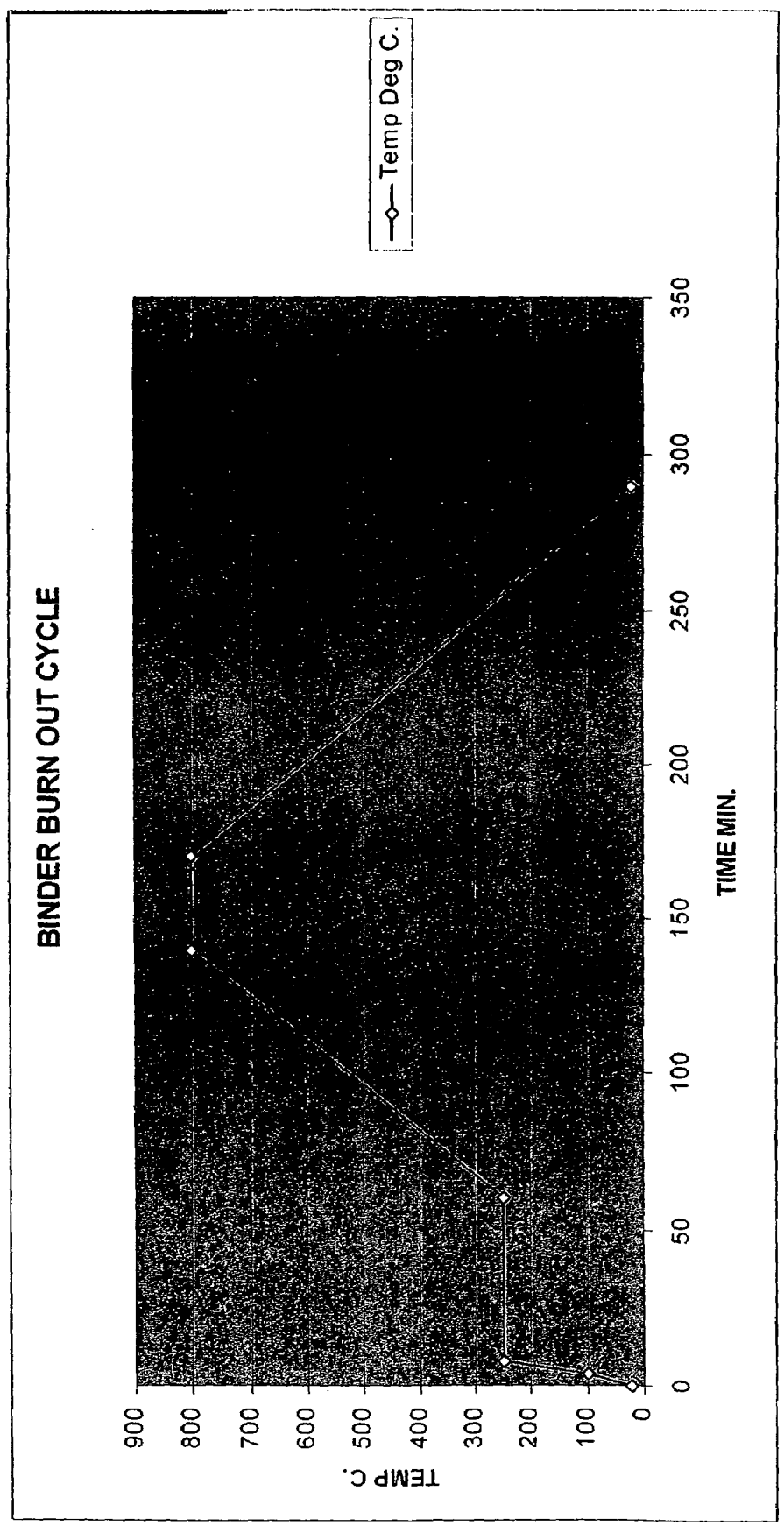
Figure 10:
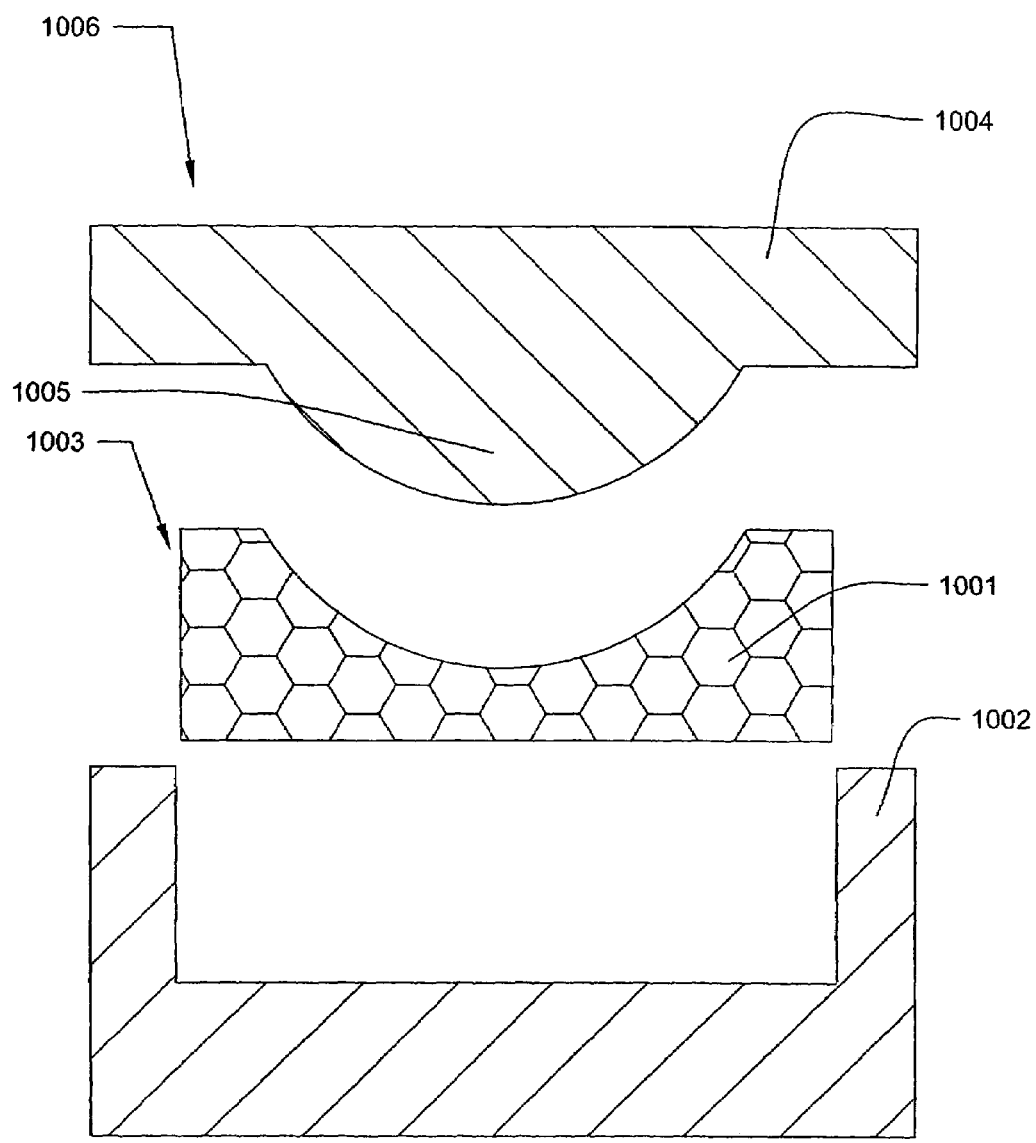
Figure 11:
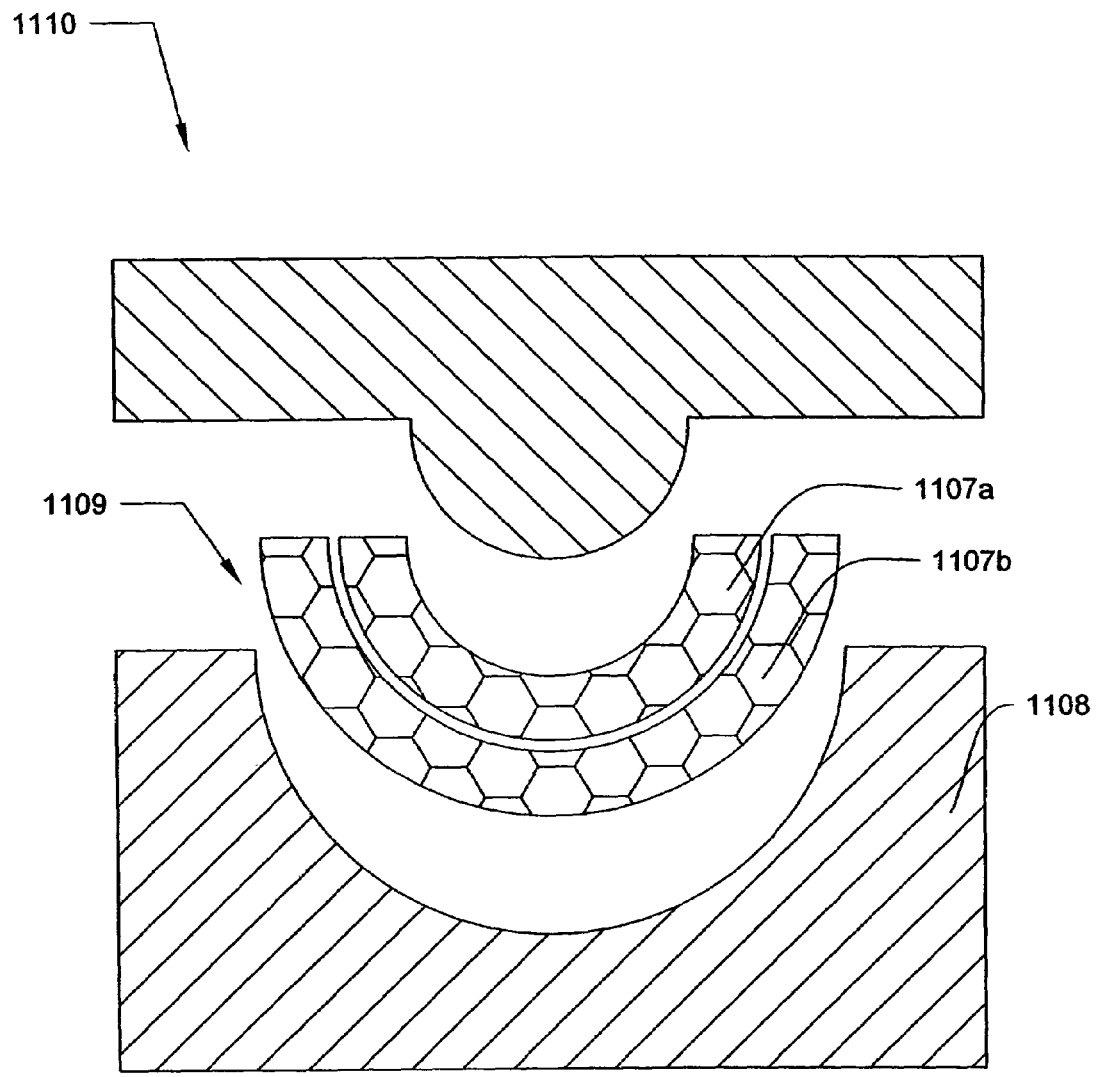

FIGS. 4E and 4E-1 depict a spherical structure 4E109 with a continuous superhard surface. The structure 4E109 depicted may be a polycrystalline diamond compact that includes a surface volume of diamond 4E9 on a substrate 4E10. This embodiment includes a continuous surface layer of diamond, although the diamond surface may be discontinuous as well.

FIGS. 4F and 4F1 depict a segmented ball 4F110 with superhard inserts 4F11 on the surface 4F12 to form a discontinuous superhard surface. The inserts 4F11 may be located on the substrate material with great precision and accuracy. The surface of the ball may be divided into areas of diamond or other superhard material separate by veins of substrate material. Fabrication of balls with this vein and patch structure (such as a polyhedral or round segmented surface) offer some advantages to the manufacturing process for certain substrate metals as well as provide some advantages in high impact situations. Each bearing segment of diamond or superhard material independently accomodate transient deformations under peak load without resulting in fracture of the segments of diamond or superhard material.

FIGS. 4G and 4G1 depict a cross-sectional view of a ball 4G111 with plugs 4G 14. The plugs 4G 14 may be a polycrystalline diamond compact having a surface of polycrystalline diamond or other superhard material. The plugs 4G14 may be fixed securely into receptacles on spherical substrate ball 4G 15 or other desired structure, or they may be formed as a compact with the substrate. The plugs or segments may be fashioned as polycrystalline diamond compacts or other superhard material. Each plug may be a continuous phase of superhard material, or a compact formed from a bearing surface of superhard material on a substrate, such as a polycrystalline diamond compact. The plugs may be bonded, welded, or mechanically fastened to the substrate structure, preferably in an appropriate receptacle, leaving a superhard bearing surface exposed. High quality curvilinear and spherical surface finishes that are obtained by terminal finishing processes described later in this document. This approach to segmented bearing surfaces permits the fabrication of extremely large spherical and or curvilinear bearing surfaces not possible with continuous bearing surfaces. Size limitations in the manufacturing of polycrystalline diamond compact elements might otherwise prevent manufacture of such large elements.

FIGS. 4H and 4H1 depict a ball 4H112 constructed of solid or continuous phase polycrystalline diamond or other superhard material. This ball 4H112 is made of solid diamond or superhard material without a separate substrate. The ball 4H112 has a continuous phase of diamond throughout its interior. Embodiments of such a continuous phase bearing element may be made from polycrystalline diamond, polycrystalline cubic boron nitride, or other superhard material. This structure has certain advantages from a chemical electromagnetic and structural standpoint.

FIGS. 4I and 4I1 depict a ball 4I113 with strips, veins or a discontinuous pattern of diamond 4I17 or another superhard material located on a substrate 4I18. The diamond on the ball 4I113 surface may be in a regular or irregular discontinuous pattern in any desired geometry, such a concentric circles, spirals, latitudinal or longitudinal lines or otherwise. This structure possesses some of the advantages common to the segmented bearing surface described above.

Finishing Methods and Apparatuses.

Once a PDC has been sintered, a mechanical finishing process may be employed to prepare the final product. The finishing steps explained below are described with respect to finishing a PDC, but they could be used to finish any other surface or any other type of component.

The synthetic diamond industry was faced with the problem of finishing flat surfaces and thin edges of diamond compacts. Methods for removal of large amounts of diamond from non-planar surfaces or finishing those surfaces to high degrees of accuracy for sphericity, size and surface finish had not been developed in the prior art.

Finishing of Superhard Cylindrical and Flat Forms.

In order to provide a greater perspective on finishing techniques for curved and non-planar superhard surfaces for modular bearing inserts and joints, a description of other finishing techniques is provided.

Lapping.

A wet slurry of diamond grit on cast iron or copper rotating plates are used to remove material on larger flat surfaces (e.g., up to about 70 mm. in diameter). End coated cylinders of size ranging from about 3 mm to about 70 mm may also be lapped to create flat surfaces. Lapping is generally slow and not dimensionally controllable for depth and layer thickness, although flatness and surface finishes can be held to very close tolerances.

Grinding.

Diamond impregnated grinding wheels are used to shape cylindrical and flat surfaces. Grinding wheels are usually resin bonded in a variety of different shapes depending on the type of material removal required (i.e., cylindrical centerless grinding or edge grinding). PDCs are difficult to grind, and large PDC surfaces are nearly impossible to grind. Consequently, it is desirable to keep grinding to a minimum, and grinding is usually confined to a narrow edge or perimeter or to the sharpening of a sized PDC end-coated cylinder or machine tool insert.

Electro Spark Discharge Grinding (EDG).

Rough machining of PDC may be accomplished with electro spark discharge grinding ("EDG") on large diameter (e.g., up to about 70 mm.) flat surfaces. This technology typically involves the use of a rotating carbon wheel with a positive electrical current running against a PDC flat surface with a negative electrical potential. The automatic controls of the EDG machine maintain proper electrical erosion of the PDC material by controlling variables such as spark frequency, voltage and others. EDG is typically a more efficient method for removing larger volumes of diamond than lapping or grinding. After EDG, the surface must be finish lapped or ground to remove what is referred to as the heat affected area or re-cast layer left by EDG.

Wire Electrical Discharge Machining (WEDM).

WEDM is used to cut superhard parts of various shapes and sizes from larger cylinders or flat pieces. Typically, cutting tips and inserts for machine tools and re-shaping cutters for oil well drilling bits represent the greatest use for WEDM in PDC finishing.

Polishing.

Polishing superhard surfaces for modular bearing inserts and joints to very high tolerances may be accomplished by diamond impregnated high speed polishing machines. The combination of high speed and high friction temperatures tends to burnish a PDC surface finished by this method, while maintaining high degrees of flatness, thereby producing a mirror-like appearance with precise dimensional accuracy.

Finishing a Non-planar Geometry.

Finishing a non-planar surface (concave non-planar or convex non-planar) presents a greater problem than finishing a flat surface or the rounded edge of a cylinder. The total surface area of a sphere to be finished compared to the total surface area of a round end of a cylinder of like radius is four (4) times greater, resulting in the need to remove four (4) times the amount of PDC material. The nature of a non-planar surface makes traditional processing techniques such as lapping, grinding and others unusable because they are adapted to flat and cylindrical surfaces. The contact point on a sphere should be a point contact that is tangential to the edge of the sphere, resulting in a smaller amount of material removed per unit of time, and a proportional increase in finishing time required. Also, the design and types of processing equipment and tooling required for finishing non-planar objects must be more accurate and must function to closer tolerances than those for other shapes. Non-planar finishing equipment also requires greater degrees of adjustment for positioning the work piece and tool ingress and egress.

The following are steps that may be performed in order to finish a non-planar, rounded or arcuate surface.

1.) Rough Machining.

Initially rough out the dimensions of the surface using a specialized electrical discharge machining apparatus may be performed. FIG. 38 depicts roughing a PDC sphere 3803. A rotator 3802 is provided that is continuously rotatable about its longitudinal axis (the z axis depicted). The sphere 3803 to be roughed is attached to a spindle of the rotator 3802. An electrode 3801 is provided with a contact end 3801a that is shaped to accommodate the part to be roughed. In this case the contact end 3801a has a partially non-planar shape. The electrode 3801 is rotated continuously about its longitudinal axis (the y axis depicted). Angular orientation of the longitudinal axis y of the electrode 3801 with respect to the longitudinal axis z of the rotator 3802 at a desired angle $\beta$ is adjusted to cause the electrode 3801 to remove material from the entire non-planar surface of the ball 3803 as desired.

Thus, the electrode 3801 and the sphere 3803 are rotating about different axes. Adjustment of the axes can be used to achieve near perfect non-planar movement of the part to be roughed. Consequently, a nearly perfect non-planar part results from this process. This method produces PDC non-planar surfaces with a high degree of sphericity and cut to very close tolerances. By controlling the amount of current introduced to the erosion process, the depth and amount of the heat affected zone can be minimized. In the case of a PDC, the heat affected zone can be kept to about 3 to 5 microns in depth and is easily removed by grinding and polishing with diamond impregnated grinding and polishing wheels.

Referring to FIG. 39, roughing a convex non-planar PDC 3903 such as an acetablular cup is depicted. A rotator 3902 is provided that is continuously rotatable about its longitudinal axis (the z axis depicted). The part 3903 to be roughed is attached to a spindle of the rotator. An electrode 3901 is provided with a contact end 3901a that is shaped to accommodate the part to be roughed. The electrode 3901 is continuously rotatable about its longitudinal axis (the y axis depicted). Angular orientation of the longitudinal axis y of the electrode 3901 with respect to the longitudinal axis z of the rotator 3902 at a desired angle $\beta$ is adjusted to cause the electrode 3901 to remove material from the entire non-planar surface of the cup 3903 as desired.

In some embodiments, multiple electro discharge machine electrodes will be used in succession in order to machine a part. A battery of electro discharge machines may be employed to carry this out in assembly line fashion. Further refinements to machining processes and apparatuses are described below.

Complex positive or negative relief (concave or convex) forms can be machined into PDC or PCBN parts. This is a standard Electrical Discharge Machining (EDM) CNC machining center and suitably machined electrodes accomplish the desired forms.

Figures 40, 40A:
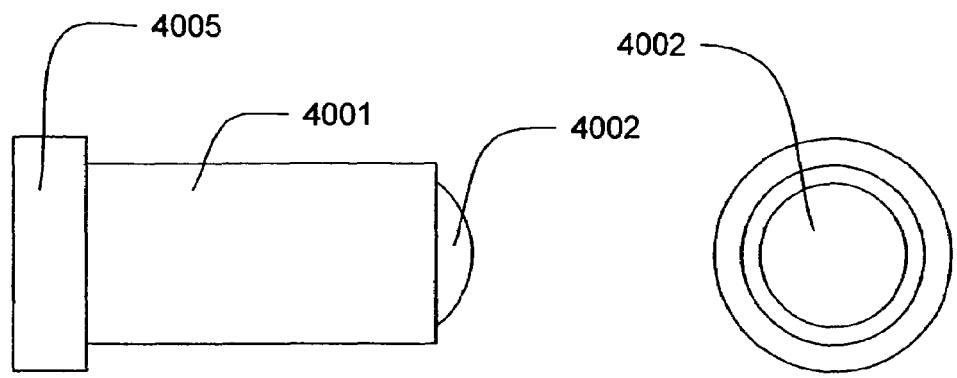
Figures 41, 41A:
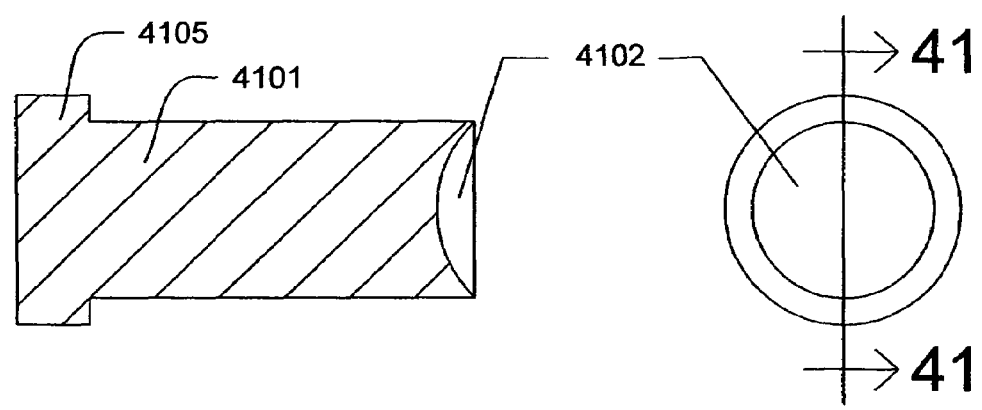

FIG. 40 (side view) and FIG. 40a (end view) show an electrode 4001 with a convex form 4002 machined on the active end of the electrode 4001, and the electrode base 4005. FIG. 41 (cross section at 41-41) and FIG. 41a show an electrode 4101 with a concave form 4102 and base 4105. The opposite ends of the electrodes are provided with an attachment mechanism at the base 4105 suitable for the particular EDM machine being utilized. There are a variety of electrode materials that can be utilized such a copper, copper tungsten, graphite, and combinations of graphite and metal mixes.

Materials best suited for machining PDC and PCBN are copper tungsten for roughing and pure graphite, or graphite copper tungsten mixes. Not all EDM machines are capable of machining PDC and PCBN. Only those equipped with capacitor discharge power supplies can generate spark intensities with enough power to efficiently erode these materials.

The actual size of the machined relief form is usually machined undersized to allow for a suitable spark gap for the burning/erosion process to take place. Each spark gap length dictates a set of machining parameters that must be set by the machine operator to ensure efficient electrical discharge erosion of the material to be removed. Normally, two to four electrodes are prepared with different spark gap allowances. For example, an electrode using a 0.006 ln. spark gap could be prepared for "roughing," and an "interim" electrode at 0.002 ln. spark gap, and "finishing" electrode at 0.0005 ln. spark gap. In each case the machining voltage (V), peak amperage (AP), pulse duration (P), reference frequency (RF), retract duration (R), under-the-cut duration (U), and servo voltage (SV) must be set up within the machines control system.

Figure 42:
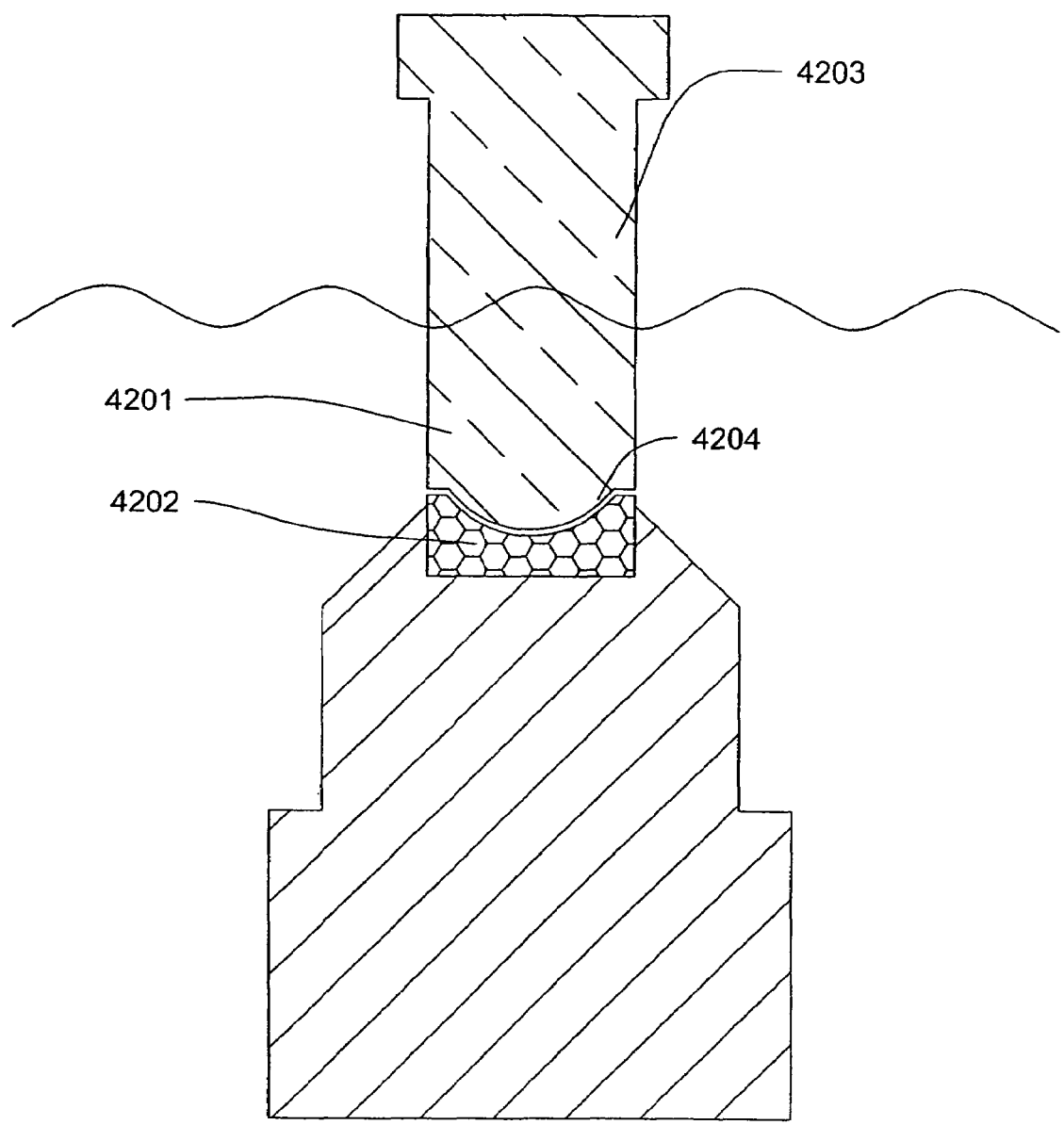

FIG. 42 shows an EDM relief form 4201 sinking operation in a PDC insert part 4202. Table 39 describes the settings for using a copper tungsten electrode 4203 for roughing and a graphite/copper tungsten electrode for finishing. The spark gap 4204 is also depicted.

TABLE 39

| Electrode 4203 | Spark Gap 4204 | V  | AP | P  | RF |
|---|---|---|---|---|---|
| Roughing  | .006 | −2 | 7 | 13 | 56 |
| Finishing | .001 | −5 | 4 | 2  | 60 |

Those familiar with the field of EDM will recognize that variations in the parameters shown will be required based on the electrode configuration, electrode wear rates desired, and surface finishes required. Generally, higher machining rates, i.e., higher values of "V" and "AP" produce higher rates of discharge erosion, but conversely rougher surface finishes.

Obtaining very smooth and accurate finishes also requires the use of a proper dielectric machining fluid. Synthetic hydrocarbons with satellite electrodes as disclosed in U.S. Pat. No. 5,773,782, which is hereby incorporated by reference, appear to assist in obtaining high quality surface finishes.

Figure 43:
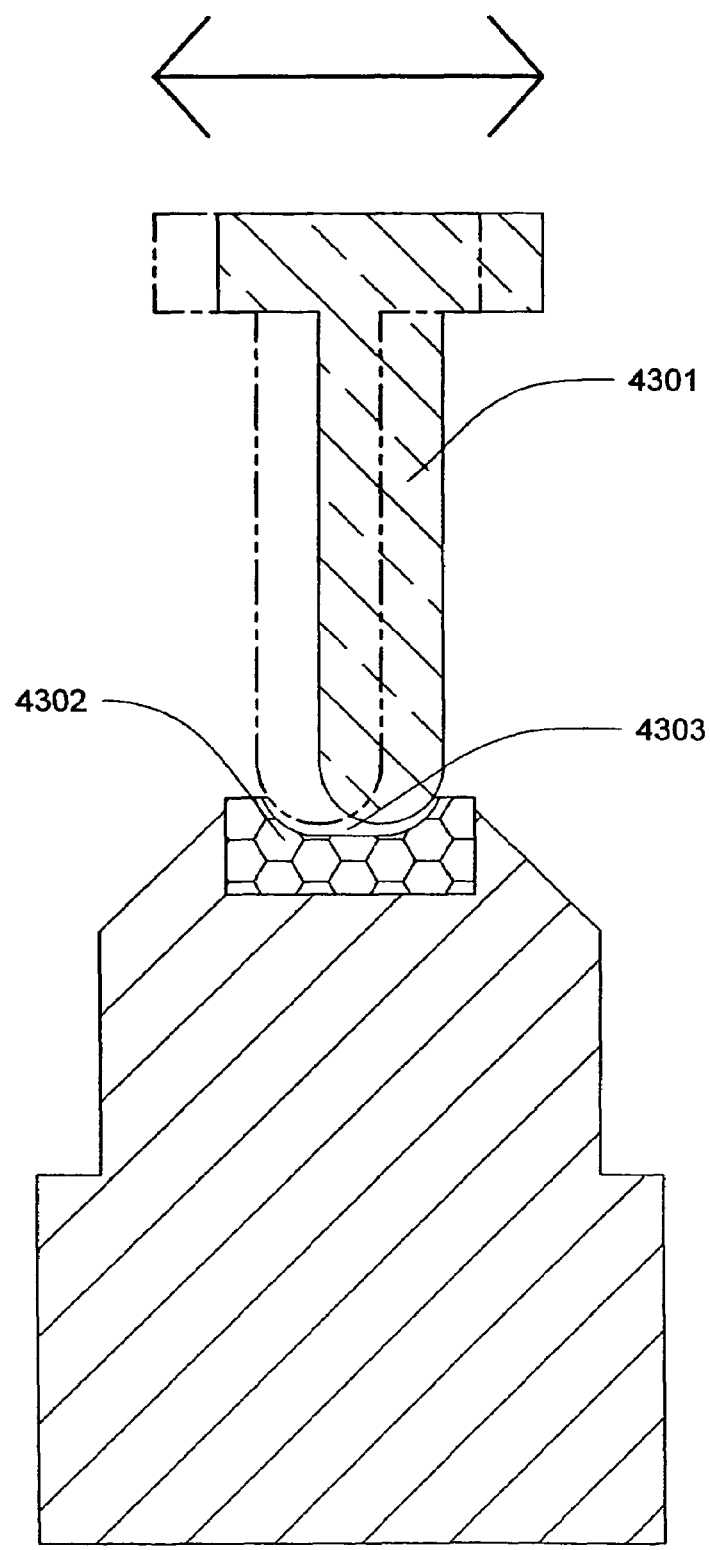

FIG. 43 shows an embodiment wherein a single ball-nosed (spherical radiused) EDM electrode 4301 is used to form a concave relief form 4303 in a PDC or PCBN part 4302. The electrode 4301 is plunged vertically into the part 4302 and then moved laterally to accomplish the rest of the desired shape. By programming a CNC system EDM electrode "cutting path" of the EDM machine, an infinite variety of concave or convex shapes can be machined. Controlling the rate of "down" plunging and "lateral" cross cutting, and using the correct EDM material will dictate the quality of the size dimensions and surface finishes obtained.

2.) Finish Grinding and Polishing.

Once the non-planar surface (whether concave or convex) has been rough machined as described above or by other methods, finish grinding and polishing of a part can take place. Grinding is intended to remove the heat affected zone in the PDC material left behind by electrodes.

In some embodiments of the devices, grinding utilizes a grit size ranging from 100 to 150 according to standard ANSI B74.16-1971 and polishing utilizes a grit size ranging from 240 to 1500, although grit size may be selected according to the user's preference. Wheel speed for grinding should be adjusted by the user to achieve a favorable material removal rate, depending on grit size and the material being ground. A small amount of experimentation can be used to determine appropriate wheel speed for grinding. Once the spherical surface (whether concave or convex) has been rough machined as described above or by other methods, finish grinding and polishing of a part can take place. Grinding is intended to remove the heat affected zone in the PDC material left behind by electrodes. Use of the same rotational geometry as depicted in FIGS. 38 and 39 allows sphericity of the part to be maintained while improving its surface finish characteristics.

Figure 44:
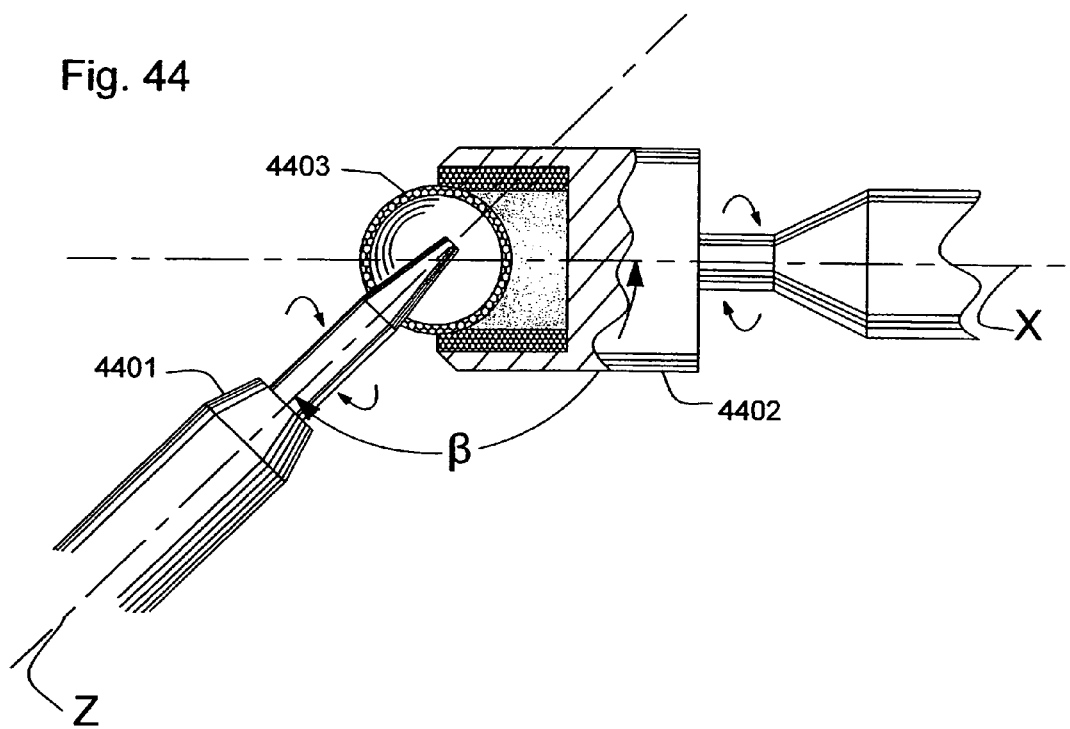

Referring to FIG. 44, it can be seen that a rotator 4401 holds a part to be finished 4403, in this case a convex sphere, by use of a spindle. The rotator 4401 is rotated continuously about its longitudinal axis (the z axis). A grinding or polishing wheel 4402 is rotated continuously about its longitudinal axis (the x axis). The moving part 4403 is contacted with the moving grinding or polishing wheel 4402. The angular orientation β of the rotator 4401 with respect to the grinding or polishing wheel 4402 may be adjusted and oscillated to effect grinding or polishing of the part (ball or socket) across its entire surface and to maintain sphericity.

Figure 45:
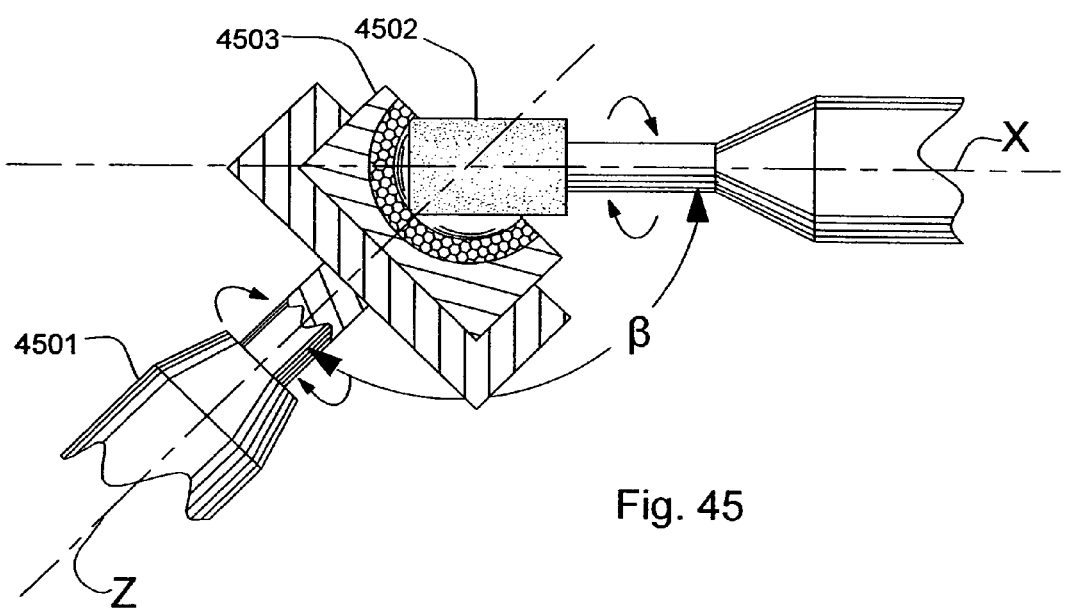

Referring to FIG. 45, it can be seen that a rotator 4501 holds a part to be finished 4503, in this case a convex non-planar cup, by use of a spindle. The rotator 4501 is rotated continuously about its longitudinal axis (the z axis). A grinding or polishing wheel 4502 is provided that is continuously rotatable about its longitudinal axis (the x axis). The moving part 4503 is contacted with the moving grinding or polishing wheel 4502. The angular orientation β of the rotator 4501 with respect to the grinding or polishing wheel 4502 may be adjusted and oscillated if required to effect grinding or polishing of the part across the non-planar portion of it surface.

In one embodiment, grinding utilizes a grit size ranging from 100 to 150 according to standard ANSI B74.16-1971 and polishing utilizes a grit size ranging from 240 to 1500, although grit size may be selected according to the user's preference. Wheel speed for grinding should be adjusted by the user to achieve a favorable material removal rate, depending on grit size and the material being ground. A small amount of experimentation can be used to determine appropriate wheel speed for grinding.

As desired, a diamond abrasive hollow grill may be used for polishing diamond or superhard surfaces. A diamond abrasive hollow grill includes a hollow tube with a diamond matrix of metal, ceramic and resin (polymer).

If a diamond surface is being polished, then the wheel speed for polishing will be adjusted to cause a temperature increase or heat buildup on the diamond surface. This heat buildup will cause burnishing of the diamond crystals to create a very smooth and mirror-like low friction surface. Actual material removal during polishing of diamond is not as important as removal of sub-micron sized asperities in the surface by a high temperature burnishing action of diamond particles rubbing against each other. A surface speed of 6000 feet per minute minimum is generally required together with a high degree of pressure to carry out burnishing. Surface speeds of 4000 to 10,000 feet per minute are believed to be the most desirable range. Depending on pressure applied to the diamond being polished, polishing may be carried out at from about 500 linear feet per minute and 20,000 linear feet per minute.

Pressure must be applied to the work piece to raise the temperature of the part being polished and thus to achieve the most desired mirror-like polish, but temperature should not be increased to the point that it causes complete degradation of the resin bond that holds the diamond polishing wheel matrix together, or resin will be deposited on the diamond. Excessive heat will also unnecessarily degrade the surface of the diamond.

Maintaining a constant flow of coolant (such as water) across the diamond surface being polished, maintaining an appropriate wheel speed such as 6000 linear feet per minute, applying sufficient pressure against the diamond to cause heat buildup but not so much as to degrade the wheel or damage the diamond, and timing the polishing appropriately are all important and must all be determined and adjusted according to the particular equipment being used and the particular part being polished. Generally the surface temperature of the diamond being polished should not be permitted to rise above 800 degrees Celsius or excessive degradation of the diamond will occur. Desirable surface finishing of the diamond, called burnishing, generally occurs between 650 and 750 degrees Celsius.

During polishing it is important to achieve a surface finish that has the lowest possible coefficient of friction, thereby providing a low friction and long-lasting surface. Once a diamond or other superhard surface is formed in modular bearing inserts and joints, the surface may then be polished to an Ra value of 0.3 to 0.005 microns. Acceptable polishing will include an Ra value in the range of 0.5 to 0.005 microns or less. The parts of the modular bearing inserts and joints may be polished individually before assembly or as a unit after assembly. Other methods of polishing PDCs and other superhard materials may be adapted to work with the invented modular bearing inserts and joints, with the objective being to achieve a smooth surface, with an Ra value of 0.01-0.005 microns. Further grinding and polishing details are provided below.

Figure 46:
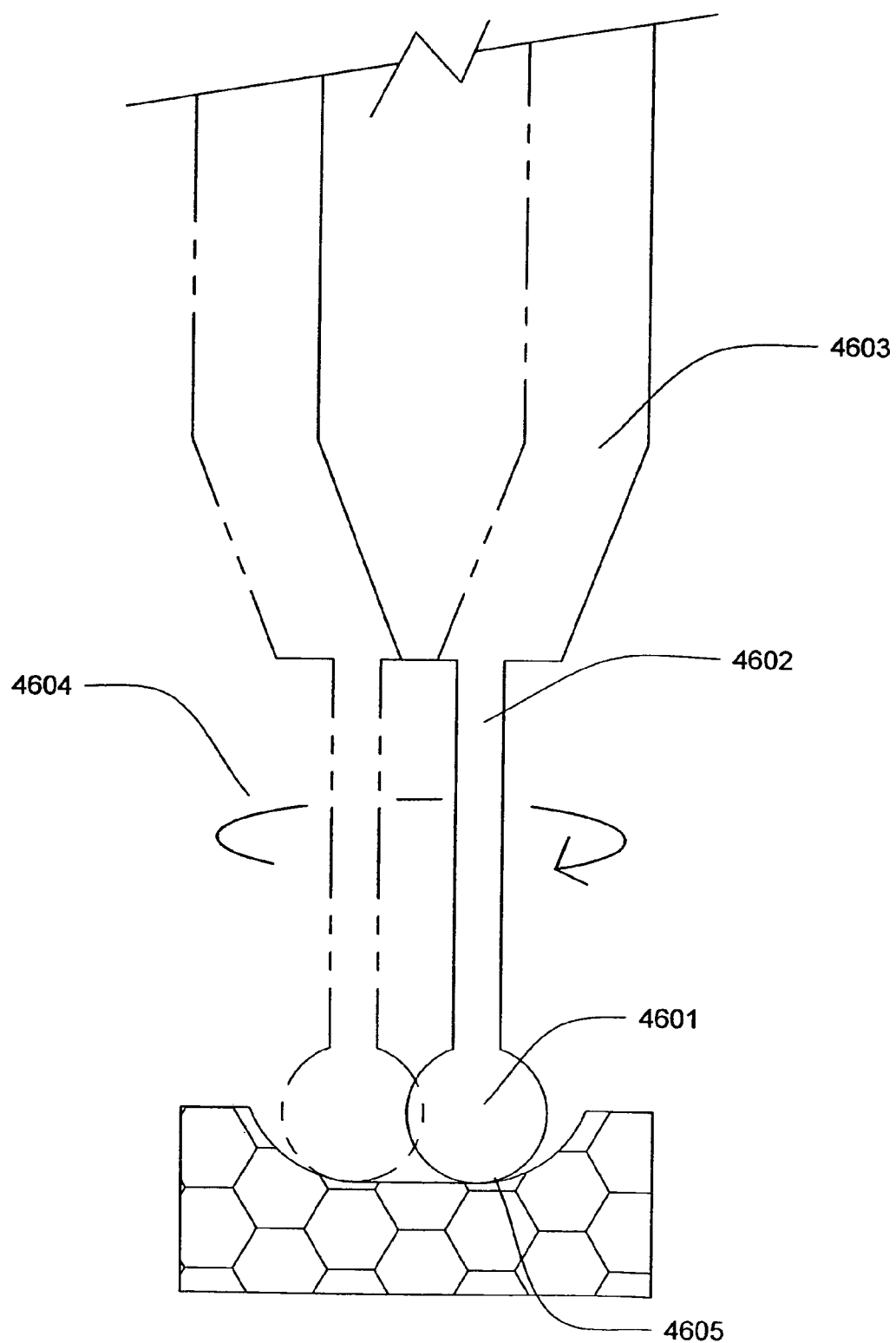

FIG. 46 shows a diamond grinding form 4601 mounted to an arbor 4602, which is in turn mounted into the high-speed spindle 4603 of a CNC grinding machine. The cutting path motion 4604 of the grinding form 4601 is controlled by the CNC program allowing the necessary surface coverage requiring grinding or polishing. The spindle speed is generally related to the diameter of the grinding form and the surface speed desired at the interface with the material 4605 to be removed. The surface speed should range between 4,000 and 17,000 feet per minute for both grinding and polishing. For grinding, the basic grinding media for the grinding form should be as "free cutting" as practical with diamond grit sizes in the range of 80 to 120 microns and concentrations ranging from 75 to 125. For polishing the grinding media should not be as "free cutting," i.e., the grinding form should generally be harder and denser with grit sizes ranging from 120 to 300 microns and concentrations ranging from 100 to 150.

Superhard materials can be more readily removed by grinding if the actual area of the material being removed is kept as small as possible. Ideally the bruiting form 4601 should be rotated to create conditions in the range from 20,000 to 40,000 surface feet per minute between the part 4605 and the bruiting form 4601. Spindle pressure between the part 4605 and the bruiting form 4601 operating in a range of 10 to 100 Lbs—force producing an interface temperature between 650 and 750 degrees Celsius is required. Cooling water is needed to take away excess heat to keep the part from possibly failing. The simplest way to keep the grind area small is to utilize a small cylindrical contact point (usually a ball form, although a radiused end of a cylinder accomplishes the same purpose), operating against a larger surface area.

Figure 47:
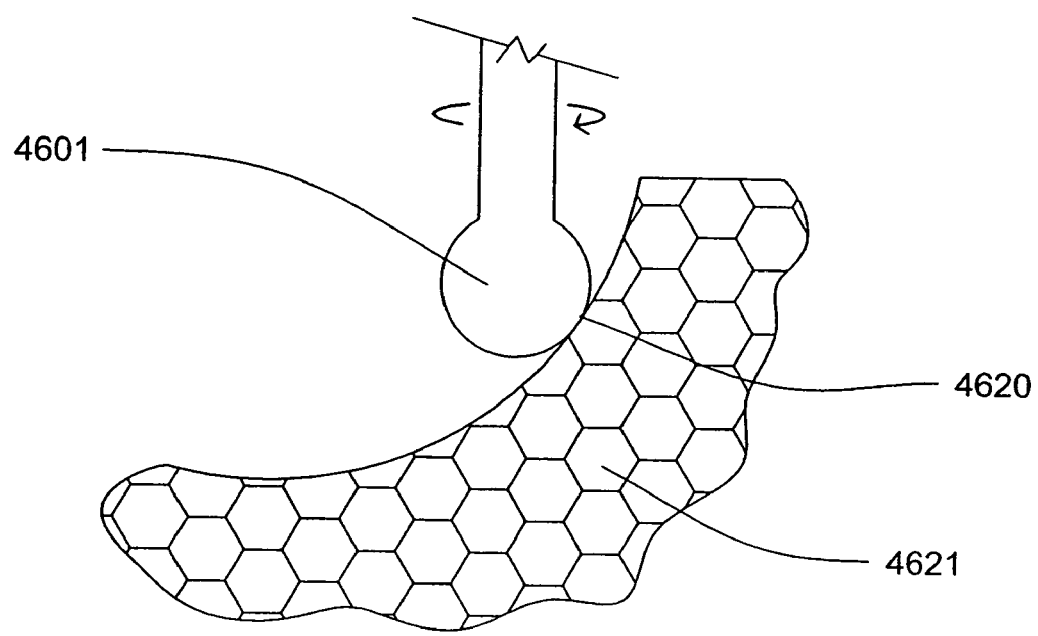
Figure 48:
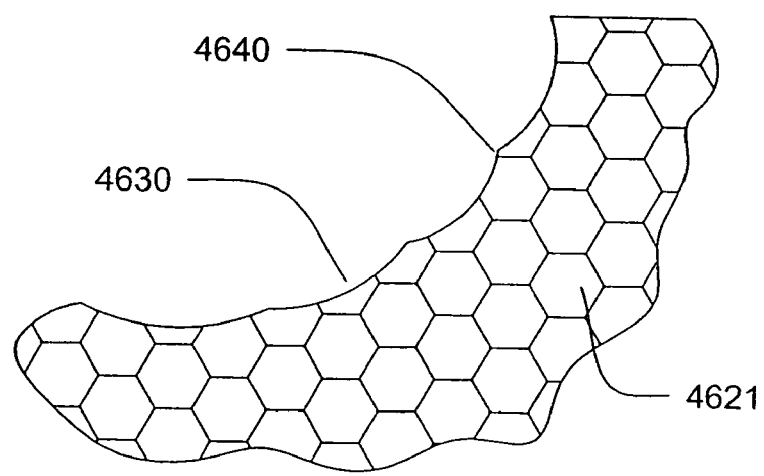

FIG. 47 shows the tangential area of contact 4620 between the grinding form 4601 and the substantially larger superhard material 4621. By controlling the path of the grinding form cutter, small grooves 4630 (FIG. 48) can be ground into the surface of the superhard material 4621 removing the material and leaving small "cusps" 4640 between the adjacent grooves. As the grooves are cut shallower and closer together the "cusps" 4640 become imperceptible to the naked eye and are easily removed by subsequent polishing operations. The cutter line path of the grinding form cutter should be controlled by programming the CNC system of the grinding machine to optimize the cusp size, grinding form cutter wear, and material removal rates.

Bruiting.

Obtaining highly polished surface finishes on PDC, PBCN, and other superhard materials in the range of 0.05 to 0.005 µm can be obtained by running a PDC form against the surface to be polished. "Bruiting" or rubbing a diamond surface under high pressure and temperature against another superhard material degredates or burns away any positive asperities remaining from previous grinding and polishing operations producing a surface finish not obtainable in any other way.

Figure 49:
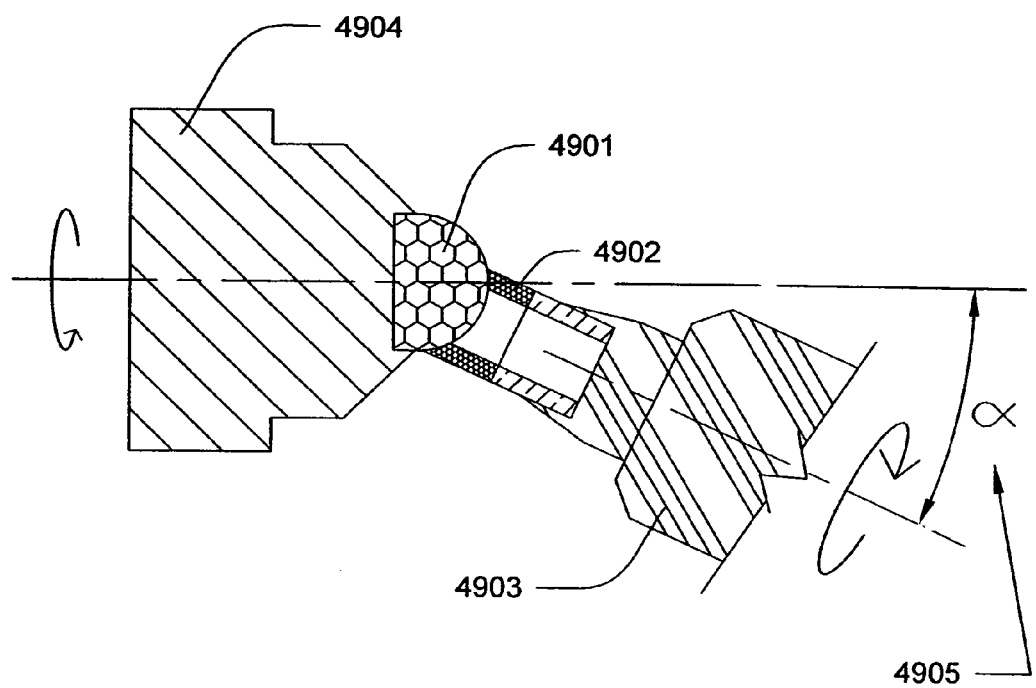

FIG. 49 shows a PDC dome part 4901 on a holder 4904 and being "Bruit Polished" using a PDC bruiting form 4902 being rotated in a high-speed spindle 4903. Ideally the bruiting form should be rotated in a range from 20,000 to 40,000 surface feet per minute with the spindle pressure operating in a range of 10 to 100 Lbs—force producing an interface temperature between 650 and 750 degrees Celsius. Angle α 4905 represents the angular orientation of the longitudinal axis of the spindle 4903 with respect to the central axis of the part 4901. Cooling water is generally required to take away excess heat to keep the part from failing.

Figure 50:
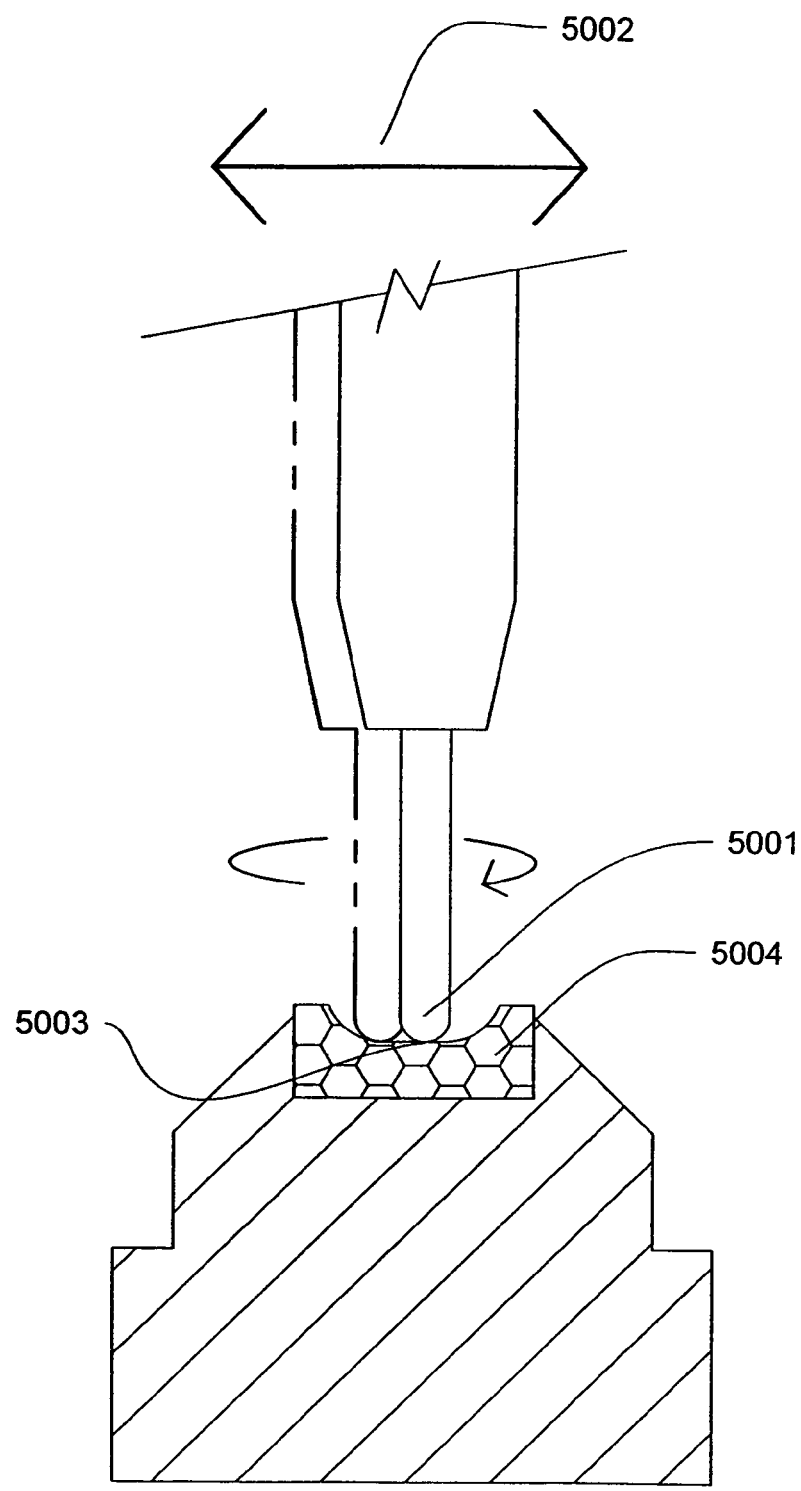

FIG. 50 shows another embodiment of the bruiting polishing technique wherein the PDC bruiting form 5001 is controlled through a complex surface path 5002 by a CNC system of a grinding machine or a CNC Mill equipped with a high-speed spindle to control the point of contact 5003 of the form 5001 with a superhard component 5004.

Use of Cobalt Chrome Molybdenum (CoCrMo) Alloys to Augment Biocompatibility in PDCS.

Cobalt and Nickel may be used as catalyst metals for sintering diamond powder to produce sintered PDCs. The toxicity of both Co and Ni is well documented; however, use of CoCr alloys which contain Co and Ni have outstanding corrosion resistance and avoid passing on the toxic effects of Co or Ni alone. Use of CoCrMo alloy as a solvent-catalyst metal in the making of sintered PDCs yields a biocompatible and corrosion resistant material. Such alloys may be defined as any suitable biocompatible combination of the following metals: Co, Cr, Ni, Mo, Ti and W. Examples include ASTM F-75, F-799 and F-90. Each of these will serve as a solvent-catalyst metal when sintering diamond. Elemental analysis of the interstitial metal in PDC made with these alloys has shown that the composition is substantially more corrosion resistant than PDC made with Co or Ni alone. Interstitial metal in PDC made with these metals is substantially more corrosion resistant than PDC made with Co or Ni is and is therefore well suited for medical applications.

Carbides as Substrate Materials

Following known procedures for the production of carbides, both Ti/TiC (Ti cemented TiC) and Nb/TiC (Nb cemented TiC) can be manufactured for use as substrate materials in prosthetic joints (such as femoral heads of prosthetic hip joints) and components thereof. Ti (or Nb) is mixed with TiC powder and formed into a ball enclosed by an Nb can. The materials are then formed into a solid hipping (hot isostatic pressing) in a high pressure press. The result is either Ti cemented TiC or Nb cemented TiC, producing a biocompatabile product. The same result could also be achieved by sintering the Ti (or Nb)+TiC using known sintering procedures such as those used in the carbide industry. Ti, Nb and TiC have biocompatible materials and therefore can be used for biomedical applications such as spinal and hip implants among others.

Carbide and metal micron powders are added together in a container with wax and acetone or other appropriate solvent along with carbide mixing balls. The materials are then milled in an attritor mill for examples for an appropriate period of time to thoroughly mix all components and to reduce the material to the target grain size (the process is controlled to obtain a specific grain size). After milling the solvent is evaporated off and the resulting powder is then pressed in a compaction press to the desired shape. The individual parts are then placed in a furnace and slowly heated to burn off the wax. Too rapid a wax removal will cause the parts to have excessive porosity or cause them to catastrophically fall apart. After removal of the wax, the parts are then taken up to the sintering temperature and held until sintering is complete. To minimize or completely eliminate open porosity, the parts may be hipped in a standard hipping furnace in which the parts are pressurized to ~30,000 psi. A more extreme hipping process is also available called rapid omnidirectional compaction (ROC). In this process the parts are rapped in grafoil or graphite paper and placed in a pressure container with glass powder. The contents are then taken to 125,000 psi and the target temperature where the glass powder melts at which time it uniformly applies pressure to the part, thus essentially reducing the porosity to zero.

The actual temperature for sintering carbides is determined by the system that one is working in. For tungsten carbide the temperature is approximately 1200° C. A typical hipping pressure is 30,000 psi whereas in the ROC process it is –125,000 psi. The target temperature and pressure are approached slowly over several hours. When the target conditions are attained they are held for only minutes before the pressure and temperature are slowly decreased to room temperature and pressure.

Material formulations for carbides is determined by the ultimate use of the material. If toughness is the desired property then the metal content of the carbide will range upwards of 13 to >20 weight %. If wear resistance or a low thermal expansion are the desired properties then the metal content of the carbide will be <13 weight %.

Use of Ti and Nb Cemented TiC for Use in Prosthetic Joints

A sintering and/or hipping process can be used to create Ti or Nb cemented TiC balls. The balls are then placed in an Nb can with diamond between the can and the ball. The filled can is then placed in a high pressure/high temperature press and the diamond is sintered to the ball. Ti and Nb are useful in this ball production process because diamond will chemically bond with TiC grains during the sintering process in a structure that is similar to the crystalline structure of diamond. The diamond will also chemically bond to the Ti and Nb because both are good carbide forming elements. The chemical bonding will increase the adhesion of the diamond to the substrate (ball core) and prevent the diamond from delaminating during use. Ti and Nb are used in conjunction with TiC because their dilatation during the sintering process exceeds that of their coefficient of thermal expansion (CTE), consequently a strong ball that does not suffer fracture from residual stress is produced. The balance between the material properties of the diamond layer and the core ball or substrate is accomplished by calculating the volumetric thermal expansion of all components (=3*CTE*ΔT, where ΔT is the temperature difference between room temperature and the sintering temperature). Similarly the volumetric dilatation must be calculated for all components using the following equation, (–3*p*(1–v))/E; where p is the sintering pressure, v is Poisson's ratio and E is the elastic modulus. The CTE and the dilatation are then added together for each component. The resulting values for each of the components in the diamond layer are then multiplied by their respective volumetric ratio in the diamond layer (the volumetric ratio of diamond to metal is fixed). These two numbers, one for the diamond and one for the metal, when added together is the total volumetric change that will occur on coming down from high pressure/temperature to room temperature for the diamond table. The is the volumetric change that must be matched by the core. To find this volume, multiply the combined CTE/dilatation for each of the two components in the core, Ti and TiC, for example by various ratios (must add to 1) until the result equals the volumetric change of the diamond layer. Only the change occurring from high temperature/pressure to room temperature/pressure is considered because at the sintering conditions the diamond will sinter around the once it has fully expanded and dilitated. Thus there will be no residual stress between them at the sintering conditions. By balancing the volumetric changes between the core and the diamond layer, they will both undergo the same volumetric changes on cooling and depressurization resulting in little or no residual stress at room temperature/pressure conditions.

While the present prosthetic joints, components thereof, materials therefore, and manufacturing methods lights have been described and illustrated in conjunction with a number of specific configurations, those skilled in the art will appreciate that variations and modifications may be made without departing from the principles herein illustrated, described, and claimed. The present invention, as defined by the appended claims, may be embodied in other specific forms without departing from its spirit or essential characteristics. The configurations described herein are to be considered in all respects as only illustrative, and not restrictive. All changes which come within the meaning and range of equivalency of the claims are to be embraced within their scope.

We claim:

1. A method for improving the biocompatibility of polycrystalline diamond compacts comprising:
   selecting a diamond feedstock comprising diamond particles,
   selecting a solvent-catalyst metal,
   said solvent-catalyst metal including CoCrMo alloy,
   said CoCrMo alloy including Ni,
   sintering said diamond into a sintered polycrystalline diamond compact in the presence of said solvent-catalyst metal such that said solvent-catalyst metal is present between the diamond particles in said compact;
   wherein said sintered polycrystalline diamond compact has enhanced biocompatibility compared to a sintered polycrystalline diamond compact that lacks use of Co and Ni as a solvent-catalyst metal.

2. A method as recited in claim 1 wherein said polycrystalline diamond compact is substantially free of unbonded Co and Ni.

3. A method as recited in claim 1 wherein said compact includes interstitial carbides in said diamond table, said carbides being formed from said solvent-catalyst metal.

4. A method as recited in claim 1 wherein said solvent-catalyst metal includes a quantity of one or more of the following: Ti and W.

5. A method as recited in claim 1 wherein said compact includes interstitial metal between the diamond particles in the compact, said interstitial metal including at least one of Co and Ni.

6. A method for improving the biocompatibility of polycrystalline diamond compacts comprising:

selecting a diamond feedstock comprising diamond particles, selecting a substrate that includes a solvent-catalyst metal, said solvent-catalyst metal including CoCrMo and Ni, sintering said diamond and said substrate into a sintered polycrystalline diamond compact, said compact comprising a diamond table formed on the surface of said substrate, said sintering causing a sweep of solvent-catalyst metal from said susbtrate to pass into said diamond feedstock, such that said diamond table comprises interstitial spaces between said diamond particles with solvent-catalyst metal therein, and such that said diamond table comprises both diamond to diamond and diamond to metal bonds;

wherein said sintered polycrystalline diamond compact has enhanced biocompatibility compared to a sintered polycrystalline diamond compact that does not utilize CoCrMo as a solvent-catalyst metal.

7. A method as recited in claim 6 wherein said polycrystalline diamond compact is substantially free of unbonded Co and Ni.

8. A method as recited in claim 6 wherein said diamond table comprises carbides formed from said solvent-catalyst metal.

9. A method as recited in claim 6 wherein said solvent-catalyst metal includes a quantity of one or more of the following: Ti and W.

* * * * *